US012570646B2

(12) United States Patent
Lee et al.

(10) Patent No.: US 12,570,646 B2
(45) Date of Patent: Mar. 10, 2026

(54) COMPOUNDS AS HISTONE DEACETYLASE 6 INHIBITOR, AND PHARMACEUTICAL COMPOSITION COMPRISING THE SAME

(71) Applicant: CHONG KUN DANG PHARMACEUTICAL CORP., Seoul (KR)

(72) Inventors: Chang Sik Lee, Gyeonggi-do (KR); Jung Taek Oh, Gyeonggi-do (KR); Hokeun Yun, Gyeonggi-do (KR); Hyeseung Song, Gyeonggi-do (KR); Hyunjin Michael Kim, Gyeonggi-do (KR)

(73) Assignee: Chong Kun Dang Pharmaceutical Corp. (KR)

( * ) Notice: Subject to any disclaimer, the term of this patent is extended or adjusted under 35 U.S.C. 154(b) by 501 days.

(21) Appl. No.: 18/024,081

(22) PCT Filed: Sep. 1, 2021

(86) PCT No.: PCT/IB2021/057975
§ 371 (c)(1),
(2) Date: Mar. 1, 2023

(87) PCT Pub. No.: WO2022/049496
PCT Pub. Date: Mar. 10, 2022

(65) Prior Publication Data

US 2023/0295142 A1 Sep. 21, 2023

(30) Foreign Application Priority Data

Sep. 2, 2020 (KR) ........................ 10-2020-0111966

(51) Int. Cl.
*C07D 413/14* (2006.01)
*C07D 413/10* (2006.01)
*C07D 487/10* (2006.01)

(52) U.S. Cl.
CPC ......... *C07D 413/14* (2013.01); *C07D 413/10* (2013.01); *C07D 487/10* (2013.01)

(58) Field of Classification Search
CPC ... C07D 413/14; C07D 413/10; C07D 487/10
USPC .......................................................... 514/374
See application file for complete search history.

(56) References Cited

U.S. PATENT DOCUMENTS

| | | | |
|---|---|---|---|
| 2009/0192171 A1 | 7/2009 | Hutchinson et al. | |
| 2017/0145012 A1 | 5/2017 | Buckmelter et al. | |
| 2023/0257372 A1 | 8/2023 | Lee et al. | |

FOREIGN PATENT DOCUMENTS

| | | | |
|---|---|---|---|
| CA | 3137054 | A1 | 10/2020 |
| CN | 107980040 | A | 5/2018 |
| CN | 114269739 | A | 4/2022 |
| EP | 2411009 | | 3/2013 |
| JP | 2012-521974 | A | 9/2012 |
| JP | 2018-521092 | A | 8/2018 |
| JP | 2018-523663 | A | 8/2018 |
| JP | 2019-504821 | A | 2/2019 |
| JP | 2019-528975 | A | 10/2019 |
| JP | 2022-529695 | A | 6/2022 |
| KR | 1020170013186 | A | 2/2017 |
| KR | 1020170013187 | A | 2/2017 |
| KR | 1020220012243 | A | 2/2022 |
| RU | 2695227 | C1 | 7/2019 |
| RU | 2709207 | C2 | 12/2019 |
| RU | 2018121499 | | 12/2019 |
| WO | WO 2007012661 | A1 | 2/2007 |
| WO | WO 2009119880 | A1 | 10/2009 |
| WO | WO 2010089303 | | 8/2010 |
| WO | WO 2010109148 | | 9/2010 |
| WO | WO 2011011186 | | 1/2011 |
| WO | WO 2011091213 | | 7/2011 |
| WO | WO 2013008162 | | 1/2013 |
| WO | WO 2013041407 | | 3/2013 |
| WO | WO 2013052110 | | 4/2013 |
| WO | WO 2013066833 | | 5/2013 |
| WO | WO 2013066835 | | 5/2013 |
| WO | WO 2013066838 | | 5/2013 |

(Continued)

OTHER PUBLICATIONS

Extended European Search Report in European Appln. No. 21863810.4, mailed on Sep. 19, 2024, 8 pages.

(Continued)

*Primary Examiner* — Kahsay Habte

(74) *Attorney, Agent, or Firm* — Fish & Richardson P.C.

(57) ABSTRACT

The present invention relates to a novel compound having a selective HDAC6 inhibitory activity, stereoisomers thereof, pharmaceutically acceptable salts thereof, a use thereof in preparation of a therapeutic medicament, a pharmaceutical composition containing the same, a therapeutic method using the composition, and a method for preparing the same, wherein the novel compound having the selective HDAC6 inhibitory activity is represented by chemical formula (I) below.

(I)

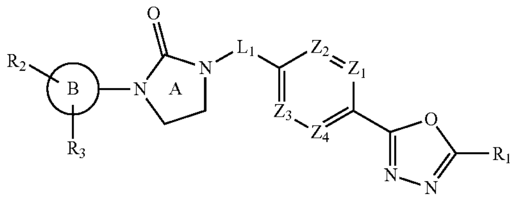

7 Claims, No Drawings

(56) References Cited

FOREIGN PATENT DOCUMENTS

| | | |
|---|---|---|
| WO | WO 2013066839 | 5/2013 |
| WO | WO 2013080120 | 6/2013 |
| WO | WO 2013134467 | 9/2013 |
| WO | WO 2017018804 A1 | 2/2017 |
| WO | WO 2017018805 A1 | 2/2017 |
| WO | WO 2017023133 | 2/2017 |
| WO | WO 2017087837 | 5/2017 |
| WO | WO 2017222950 A1 | 12/2017 |
| WO | WO 2017222951 | 12/2017 |
| WO | WO 2017222952 A1 | 12/2017 |
| WO | WO 2018065254 A1 | 4/2018 |
| WO | WO 2019011928 A1 | 1/2019 |
| WO | WO 2019110663 | 6/2019 |
| WO | WO 2020127974 A1 | 6/2020 |
| WO | WO 2020212479 A1 | 10/2020 |
| WO | WO 2020240492 | 12/2020 |
| WO | WO 2022029041 A1 | 2/2022 |

OTHER PUBLICATIONS

Office Action in Canadian Appln. No. 3191319, mailed on Apr. 29, 2024, 4 pages.
Office Action in Japanese Appln. No. 2023-514400, mailed on Mar. 7, 2024, 4 pages (with English translation).
Bonacorso et al., "Synthesis, Structure Elucidation, Antioxidant and Antimicrobial Activity of Novel 2-(5-Trifluoromethyl-1H-pyrazol-1-yl)-5-(5-trihalomethyl-1H-pyrazol-l-yl-l-carbonyl) pyridines," Journal of the Brazilian Chemical Society, 2015 26:2346-2361.
Extended European Search Report in European Appln. No. 21841400.1, mailed on Jun. 20, 2024, 7 pages.
International Search Report and Written Opinion in International Appln. No. PCT/IB2021/056282, dated Oct. 26, 2021, 12 pages.
Kümmererer, "Pharmaceuticals in the environment," Annual Review of Environment and Resources, 2010, 35:57-75 (see abstract, p. 60).
Office Action in Australian Appln. No. 2021308344, mailed on Aug. 30, 2023, 9 pages.
Office Action in Canadian Appln. No. 3185923, mailed on May 2, 2024, 5 pages.
Office Action in Chinese Appln. No. 202180061215.2, mailed on Oct. 8, 2024, 19 pages (with English translation).
Office Action in India Appln. No. 202337009277, mailed on Sep. 26, 2023, 6 pages (with English translation).
Office Action in Japanese Appln. No. 2023-501800, mailed on Mar. 11, 2024, 5 pages (with English translation).
Office Action in Korean Appln. No. 10-2021-0091902, dated Oct. 4, 2022, 10 pages (with Machine Translation).
Office Action in Russia Appln. No. 2023103092, mailed on Aug. 31, 2023, 24 pages (with English translation).
Office Action in Taiwanese Appln. No. 110125754, dated May 4, 2022, 7 pages (with English Translation).
Bolden et al., "Anticancer activities of histone deacetylase inhibitors," Nat. Rev. Drug Discov., 2006, 5(9):769-784.
Chen et al., "Computational Exploration of Zinc Binding Groups for HDAC Inhibition," Manuscript, J. Org. Chem., 2013, 78:5051-5055.
Hassig et al., "Nuclear histone acetylases and deacetylases and transcriptional regulation: HATS off to HDACs," Curr. Opin. Chem. Biol., 1997, 1:300-308.
International Search Report and Written Opinion in International Application No. PCT/IB2021/057975, dated Dec. 7, 2021, 10 pages.
Kovacs et al., "HDAC6 Regulates Hsp90 Acetylation and Chaperone-Dependent Activation of Glucocorticoid Receptor," Mol. Cell, 2005, 18:601-607.
Li et al., "Discovery of a new class of histone deacetylase inhibitors with a novel zinc binding group," Med. Chem. Commun., 2015, 6 pages.
Li et al., "HDAC6 α-tubulin deacetylase: A potential therapeutic target in neurodegenerative diseases," J. Neurol. Sci., 2011, 304:1-8.
Methot et al., "Exploration of the internal cavity of histone deacetylase (HDAC) with selective HDAC1/HDAC2 inhibitors (SHI-1:2)," Bioorg. Med. Chem. Lett., 2008, 18:973-978.
Santo et al., "Preclinical activity, pharmacodynamic, and pharmacokinetic properties of a selective HDAC6 inhibitor, ACY-1215, in combination with bortezomib in multiple myeloma," Blood, 2012, 119:2579-2589.
Subramanian et al., "Clinical Toxicities of Histone Deacetylase Inhibitors," Pharmaceuticals, 2010, 3:2751-2767.
TW Office Action in Taiwanese Application No. 110132427, dated Apr. 28, 2022, 8 pages (with English Translation).
Vishwakarma et al., "Tubastatin, a selective histone deacetylase 6 inhibitor shows anti-inflammatory and anti-rheumatic effects," International Immunopharmacology, 2013, 16:72-78.
Warrell Jr. et al., "Therapeutic Targeting of Transcription in Acute Promyelocytic Leukemia by Use of an Inhibitor of Histone Deacetylase," J. Natl. Cancer Inst., 1998, 90:1621-1625.
Witt et al., "HDAC family: What are the cancer relevant targets?," Cancer Letters, 2009, 277:8-21.
Zhang et al., "Mice Lacking Histone Deacetylase 6 Have Hyperacetylated Tubulin but Are Viable and Develop Normally," Mol. Cell. Biol., 2008, 28:1688-1701.
Alekseev, "Optical isometry and pharmacological activity of drugs," Sorov Educational Journal, 1998, (1)49-55 (with English Translation).
Belikov, "Pharmaceutical chemistry," textbook, Moscow, "MEDpress—inform", 2007, pp. 27-29 (with English Translation).
Dyson et al., "Chemistry of Synthetic Medicinal Substances," Mir, Moscow, 1964, pp. 12-19 (with English Translation).
Office Action in Australian Application No. 2021337217, dated Aug. 10, 2023, 9 pages.
Office Action in Chinese Application No. 202180053894.9, dated Aug. 31, 2023, 13 pages (with English Translation).
Office Action in Indian Application No. 202337023623, dated Dec. 27, 2023, 5 pages (with English Translation).
Office Action in Russian Application No. 2023107900, dated Aug. 22, 2023, 17 pages (with English Translation).
Vasilenko, "Optical isomers in pharmacy," Development and registration of medicines, 2015, (1)92-97 (with English Translation).

COMPOUNDS AS HISTONE DEACETYLASE 6 INHIBITOR, AND PHARMACEUTICAL COMPOSITION COMPRISING THE SAME

TECHNICAL FIELD

The present invention relates to a novel compound having a histone deacetylase 6 (HDAC6) inhibitory activity, stereoisomers thereof, pharmaceutically acceptable salts thereof, a use thereof in preparation of a therapeutic medicament, a pharmaceutical composition containing the same, a therapeutic method using the composition, and a method for preparing the same.

BACKGROUND

In cells, a post-translational modification such as acetylation serves as a very important regulatory module at the hub of biological processes, and is also strictly controlled by a number of enzymes. As a core protein constituting chromatin, histone functions as an axis, around which DNA winds, and thus helps a DNA condensation. Also, a balance between acetylation and deacetylation of histone plays a very important role in gene expression.

As an enzyme for removing an acetyl group from lysine residue of histone protein, which constitutes chromatin, histone deacetylase (HDAC) is known to be associated with gene silencing and induce a cell cycle arrest, angiogenic inhibition, immunoregulation, apoptosis, etc. (Hassig et al., Curr. Opin. Chem. Biol. 1997, 1, 300-308). Also, it is reported that the inhibition of HDAC enzyme functions induces cancer cells into committing apoptosis for themselves by lowering an activity of cancer cell survival-related factors and activating cancer cell death-related factors in the body (Warrell et al., J. Natl. Cancer Inst. 1998, 90, 1621-1625).

For humans, 18 HDACs are known and classified into four classes according to homology with yeast HDAC. In this case, eleven HDACs using zinc as a cofactor may be divided into three groups: Class I (HDAC1, 2, 3, 8), Class II (IIa: HDAC4, 5, 7, 9; IIb: HDAC6, 10) and Class IV (HDAC11). Further, seven HDACs of Class III (SIRT 1-7) use NAD+ as a cofactor instead of zinc (Bolden et al., Nat. Rev. Drug Discov. 2006, 5(9), 769-784).

Various HDAC inhibitors are now in a preclinical or clinical development stage, but only non-selective HDAC inhibitors have been known as an anti-cancer agent so far. Vorinostat (SAHA) and romidepsin (FK228) have obtained an approval as a therapeutic agent for cutaneous T-cell lymphoma, while panobinostat (LBH-589) has won an approval as a therapeutic agent for multiple myeloma. However, it is known that the non-selective HDAC inhibitors generally bring about side effects such as fatigue, nausea and the like at high doses (Piekarz et al., Pharmaceuticals 2010, 3, 2751-2767). It is reported that the side effects are caused by the inhibition of class I HDACs. Due to the side effects, etc., the non-selective HDAC inhibitors have been subject to restriction on drug development in other fields than an anticancer agent (Witt et al., Cancer Letters 277 (2009) 8.21).

Meanwhile, it is reported that the selective inhibition of class II HDACs would not show toxicity, which have occurred in the inhibition of class I HDACs. In case of developing the selective HDAC inhibitors, it would be likely to solve side effects such as toxicity, etc., caused by the non-selective inhibition of HDACs. Accordingly, there is a chance that the selective HDAC inhibitors may be developed as an effective therapeutic agent for various diseases (Matthias et al., Mol. Cell. Biol. 2008, 28, 1688-1701).

HDAC6, one of the class IIb HDACs, is known to be mainly present in cytoplasm and contain a tubulin protein, thus being involved in the deacetylation of a number of non-histone substrates (HSP90, cortactin, etc.) (Yao et al., Mol. Cell 2005, 18, 601-607). HDAC6 has two catalytic domains, in which a zinc finger domain of C-terminal may bind to an ubiquitinated protein. HDAC6 is known to have a number of non-histone proteins as a substrate, and thus play an important role in various diseases such as cancer, inflammatory diseases, autoimmune diseases, neurological diseases, neurodegenerative disorders and the like (Santo et al., Blood 2012 119: 2579-258; Vishwakarma et al., International Immunopharmacology 2013, 16, 72-78; Hu et al., J. Neurol. Sci. 2011, 304, 1-8).

A structural feature that various HDAC inhibitors have in common is comprised of a cap group, a linker group and a zinc binding group (ZBG) as shown in a following structure of vorinostat. Many researchers have conducted a study on the inhibitory activity and selectivity with regard to enzymes through a structural modification of the cap group and the linker group. Out of the groups, it is known that the zinc binding group plays a more important role in the enzyme inhibitory activity and selectivity (Wiest et al., J. Org. Chem. 2013 78: 5051-5065; Methot et al., Bioorg. Med. Chem. Lett. 2008, 18, 973-978).

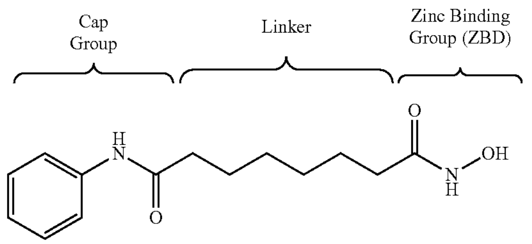 [SMILES: O=C(CCCCCCC(=O)Nc1ccccc1)NO]

Most of said zinc binding group is comprised of hydroxamic acid or benzamide, out of which hydroxamic acid derivatives show a strong HDAC inhibitory effect, but have a problem with low bioavailability and serious off-target activity. Benzamide contains aniline, and thus has a problem in that it may produce toxic metabolites in vivo (Woster et al., Med. Chem. Commun. 2015, online publication).

Accordingly, unlike the non-selective inhibitors having side effects, there is a need to develop a selective HDAC6 inhibitor, which has a zinc binding group with improved bioavailability, while causing no side effects in order to treat cancer, inflammatory diseases, autoimmune diseases, neurological diseases, neurodegenerative disorders and the like.

PRIOR ART REFERENCE

Patent Document

International Patent Publication No. WO 2011/091213 (publicized on Jul. 28, 2011): ACY-1215

International Patent Publication No. WO 2011/011186 (publicized on Jan. 27, 2011): Tubastatin International Patent Publication No. WO 2013/052110 (publicized on Apr. 11, 2013): Sloan-K International Patent Publication No. WO 2013/041407 (publicized on Mar. 28, 2013): Cellzome International Patent Publication No. WO 2013/134467 (publicized on Sep. 12, 2013): Kozi International Patent Publication No. WO 2013/008162 (publicized on Jan. 17, 2013): Novartis International Patent Publication No. WO 2013/080120 (publicized on Jun. 6, 2013): Novartis International Patent Publication No. WO 2013/066835 (publicized on May 10, 2013): Tempero International Patent Publication No. WO 2013/066838 (publicized on May 10, 2013): Tempero International Patent Publication No. WO 2013/066833 (publicized on May 10, 2013): Tempero International Patent Publication No. WO 2013/066839 (publicized on May 10, 2013): Tempero

DETAILED DESCRIPTION OF THF INVENTION

Technical Problem

An objective of the present invention is to provide a novel compound having a selective HDAC6 inhibitory activity, stereoisomers thereof or pharmaceutically acceptable salts thereof.

Another objective of the present invention is to provide a pharmaceutical composition containing a novel compound having a selective HDAC6 inhibitory activity, stereoisomers thereof or pharmaceutically acceptable salts thereof.

Still another objective of the present invention is to provide a method for preparing the same.

Still another objective of the present invention is to provide a pharmaceutical composition for preventing or treating HDAC6 activity-related diseases, containing the compound, stereoisomers thereof or pharmaceutically acceptable salts thereof as an effective ingredient.

Still another objective of the present invention is to provide a use of the compound, stereoisomers thereof or pharmaceutically acceptable salts thereof; or a pharmaceutical composition containing the same as an effective ingredient for preventing or treating HDAC6 activity-related diseases.

Still another objective of the present invention is to provide a use of the compound, stereoisomers thereof or pharmaceutically acceptable salts thereof; or a pharmaceutical composition containing the same as an effective ingredient in preparation of a medicament for preventing or treating HDAC6 activity-related diseases.

Still another objective of the present invention is to provide a method for preventing or treating HDAC6 activity-related diseases, including administering a therapeutically effective amount of the compound, stereoisomers thereof or pharmaceutically acceptable salts thereof; or a pharmaceutical composition containing the same as an effective ingredient into a subject in need thereof.

Technical Solution

The present inventors have found an oxadiazole derivative compound having a histone deacetylase 6 (HDAC6) inhibitory activity and have used the same in inhibiting or treating HDAC6 activity-related diseases, thereby completing the present invention.

Compound Represented by Chemical Formula I

The present invention provides a novel compound having a selective HDAC6 inhibitory activity represented by a following chemical formula I, stereoisomers thereof or pharmaceutically acceptable salts thereof:

[Chemical Formula I]

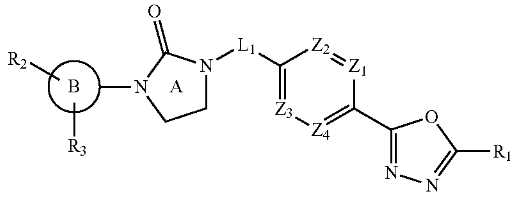

wherein, $Z_1$ to $Z_4$ are each independently N or $CR_0$ (here, $R_0$ is H or halogen);

$R_1$ is $CX_3$ or $CX_2H$ (here, X is halogen);

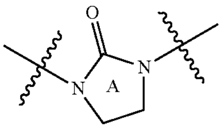

is

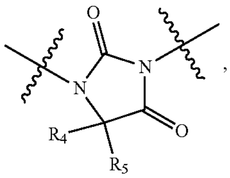

,

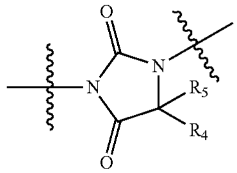

or

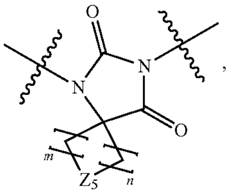

, $R_4$ and $R_5$ are each independently H or C1-C4 alkyl, $Z_5$ is N—$R_6$ or $CH_2$, $R_6$ is H, C1-C4 alkyl, —C(═O)—(C1-C4 alkyl), —C(═O)—O—(C1-C4 alkyl) or 4- to 6-membered heterocycloalkyl having one O;

$L_1$ is —(C1-C2 alkylene)-;

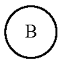

is C6-C12 aryl, 5- to 9-membered heteroaryl having at least one N or

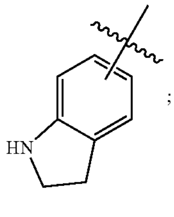

;

$R_2$ and $R_3$ are each independently H, halogen, C1-C4 alkyl, C6-C12 aryl, 5- or 6-membered heteroaryl having N or O, 5- or 6-membered heterocycloalkyl having N, 5- or 6-membered heterocycloalkenyl having N, —C(═O)—O—(C1-C4 alkyl), —C(═O)—(C1-C4 alkyl), —NH—C(═O)—(C1-C4 alkyl), —$NO_2$ or —$NH_2$, at least one H of above $R_2$ and $R_3$ may be each independently substituted with halogen or C1-C4 alkyl; and n and m are each independently 1 or 2.

In one embodiment, in above chemical formula I, $R_2$ and $R_3$ are each independently H, halogen, C1-C4 alkyl, phenyl, furanyl, pyridinyl, C1-C4 alkyl substituted or unsubstituted piperidinyl, C1-C4 alkyl substituted or unsubstituted tetrahydropyridinyl, —C(═O)—O—(C1-C4 alkyl), —C(═O)—(C1-C4 alkyl), —NH—C(═O)—(C1-C4 alkyl), —$NO_2$ or —$NH_2$,

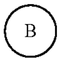

is phenyl, indole or

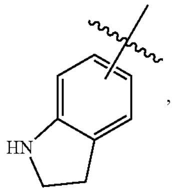

if

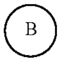

is indole or

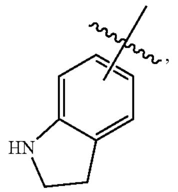

H of NH thereof may be substituted with —C(═O)—O—(C1-C4 alkyl) or —C(═O)—(C1-C4 alkyl), and if

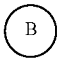

is phenyl, at least one H of phenyl may be each independently substituted with halogen, and n and m may be each independently 1 or 2.

In the present invention, the term "substituted" may represent a moiety having a substituent which replaces at least one hydrogen on carbon of a main chain. The "substitution", "may be substituted with~" or "substituted with~" may be defined to include implicit conditions, in which the substitution follows a permitted valency of a substituted atom and a substituent and induces a compound stabilized by substitution, for example, a compound which is not naturally modified by rearrangement, cyclization, removal, etc.

In the present invention, "Cx-y" may refer to having carbon atoms in a range of x to y.

In the present invention, "alkyl" may refer to a linear (or straight-chain) saturated hydrocarbon group or a branched (or side-chain) saturated hydrocarbon group, and includes methyl, ethyl, n-propyl, isopropyl, n-butyl, sec-butyl, isobutyl, tert-butyl, n-pentyl, n-hexyl, n-heptyl, etc.

In the present invention, "alkylene" may refer to a divalent functional group which is induced from the alkyl group as defined above.

In the present invention, "aryl" may include a monocyclic aromatic structure or a polycyclic aromatic structure, as well as a structure in which a saturated hydrocarbon ring is fused into the monocyclic or polycyclic aromatic group. Aryl may include a phenyl group, naphthalenyl, tetrahydronaphthalenyl, anthracenyl, phenanthrenyl, pyrenyl, etc.

In the present invention, "heteroaryl" may refer to a monocyclic or polycyclic hetero ring in which at least one carbon atom is substituted with at least one hetero atom, which is at least one of nitrogen (N) and oxygen (O) in aryl as defined above. Heteroaryl may include pyridinyl, triazolyl, tetrazolyl, indolyl, isoindolyl, furanyl, pyrrolyl, imidazolyl, oxazolyl, isoxazolyl, pyrazinyl, pyridazinyl, pyrimidinyl, etc., but is not limited thereto.

In the present invention, "cycloalkyl" may refer to a saturated hydrocarbon ring generally having a specified number of carbon atoms containing a ring, and may include cyclohexyl, cycloheptanyl, cyclooctanyl, etc. In the present invention, "heterocycloalkyl" may refer to a saturated ring structure containing one to four hetero atoms, which are at least one of nitrogen (N) and oxygen (O).

In the present invention, "heterocycloalkenyl" may refer to a structure having at least one carbon-carbon double bond containing one to four hetero atoms, which are at least one of nitrogen (N) and oxygen (O).

In the present invention, "halogen" may refer to F, Cl or Br.

In the present invention, "stereoisomer" may include a diastereomer and an optical isomer (enantiomer), in which the optical isomer may include not only an enantiomer, but also a mixture of the enantiomer and even a racemate.

In the present invention, pharmaceutically acceptable salts may refer to the salts conventionally used in a pharmaceutical industry, for example, inorganic ion salts prepared from calcium, potassium, sodium, magnesium and the like; inorganic acid salts prepared from hydrochloric acid, nitric acid, phosphoric acid, bromic acid, iodic acid, perchloric acid, sulfuric acid and the like; organic acid salts prepared from acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbric acid, carbonic acid, vanillic acid, hydroiodic acid, etc.; sulfonic acid salts prepared from methanesulfonic acid, ethanesulfonic acid, benzenesulfonic acid, p-toluenesulfonic acid, naphthalenesulfonic acid and the like; amino acid salts prepared from glycine, arginine, lysine, etc.; amine salts prepared from trimethylamine, triethylamine, ammonia, pyridine, picoline, etc.; and the like, but types of salts meant in the present invention are not limited to those listed salts.

In the present invention, preferable salts may include hydrochloride, phosphate, sulfate, trifluoroacetate, citrate, bromate, maleate or tartrate.

In one embodiment, the compound represented by chemical formula I of the present invention, stereoisomers thereof or pharmaceutically acceptable salts thereof may include the compounds as shown in table 1 below.

TABLE 1
| Compound | Structure |
|---|---|
| 1 | 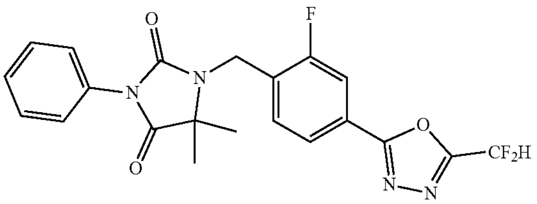 [SMILES: CC1(C)C(=O)N(c2ccccc2)C(=O)N1Cc1ccc(-c2nnc(C(F)F)o2)cc1F] |
| 2 | 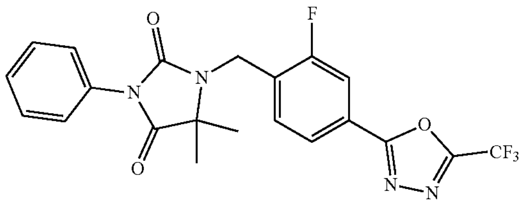 [SMILES: CC1(C)C(=O)N(c2ccccc2)C(=O)N1Cc1ccc(-c2nnc(C(F)(F)F)o2)cc1F] |
| 3 | 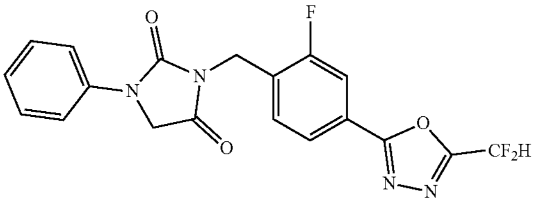 [SMILES: O=C1CN(c2ccccc2)C(=O)N1Cc1ccc(-c2nnc(C(F)F)o2)cc1F] |
| 4 | 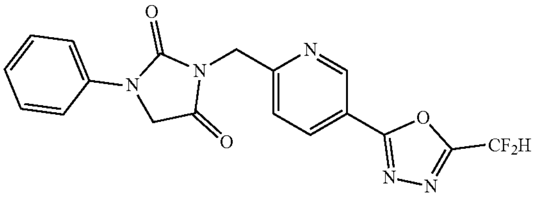 [SMILES: O=C1CN(c2ccccc2)C(=O)N1Cc1ccc(-c2nnc(C(F)F)o2)cn1] |
| 5 | 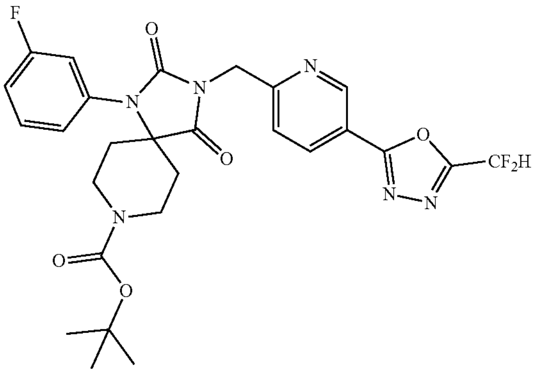 [SMILES: CC(C)(C)OC(=O)N1CCC2(CC1)C(=O)N(Cc1ccc(-c3nnc(C(F)F)o3)cn1)C(=O)N2c1cccc(F)c1] |
| 6 | 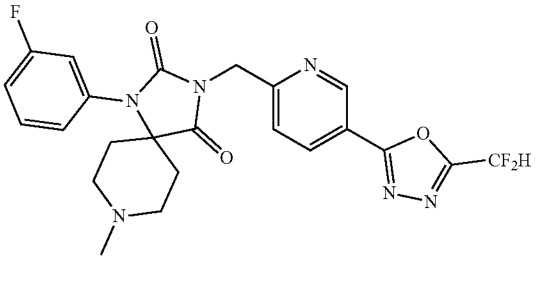 [SMILES: CN1CCC2(CC1)C(=O)N(Cc1ccc(-c3nnc(C(F)F)o3)cn1)C(=O)N2c1cccc(F)c1] |

TABLE 1-continued
| Compound | Structure |
|---|---|
| 7 | 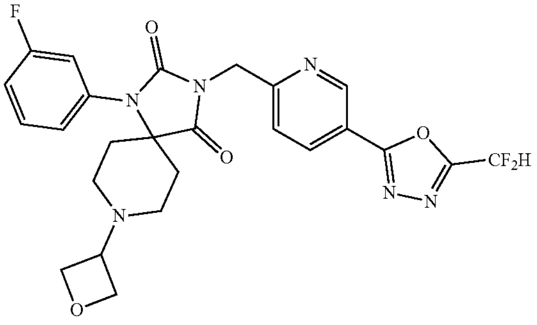 [SMILES: O=C1N(Cc2ccc(-c3nnc(C(F)F)o3)cn2)C(=O)C2(CCN(C3COC3)CC2)N1c1cccc(F)c1] |
| 8 | 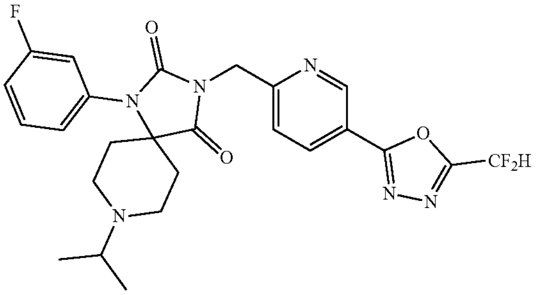 [SMILES: CC(C)N1CCC2(CC1)C(=O)N(Cc1ccc(-c3nnc(C(F)F)o3)cn1)C(=O)N2c1cccc(F)c1] |
| 9 | 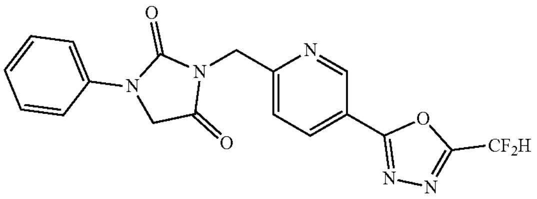 [SMILES: O=C1CN(c2ccccc2)C(=O)N1Cc1ccc(-c2nnc(C(F)F)o2)cn1] |
| 10 | 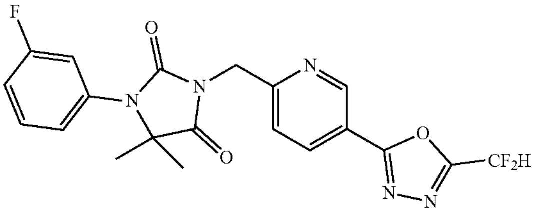 [SMILES: CC1(C)C(=O)N(Cc2ccc(-c3nnc(C(F)F)o3)cn2)C(=O)N1c1cccc(F)c1] |
| 11 | 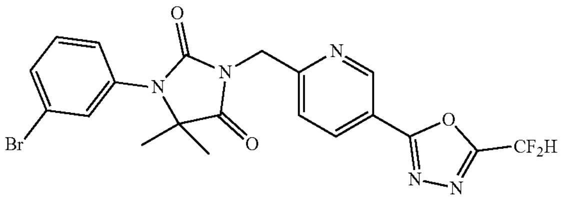 [SMILES: CC1(C)C(=O)N(Cc2ccc(-c3nnc(C(F)F)o3)cn2)C(=O)N1c1cccc(Br)c1] |
| 12 | 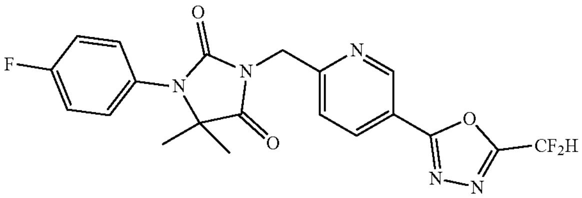 [SMILES: CC1(C)C(=O)N(Cc2ccc(-c3nnc(C(F)F)o3)cn2)C(=O)N1c1ccc(F)cc1] |

TABLE 1-continued
| Compound | Structure |
| --- | --- |
| 13 | 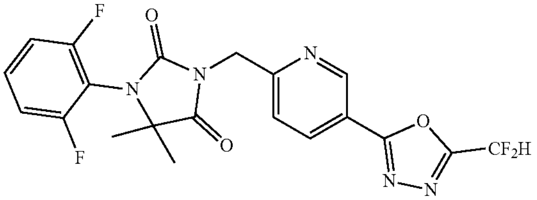 [SMILES: CC1(C)C(=O)N(Cc2ccc(-c3nnc(C(F)F)o3)cn2)C(=O)N1c1c(F)cccc1F] |
| 14 | 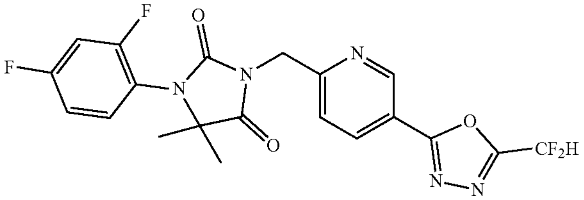 [SMILES: CC1(C)C(=O)N(Cc2ccc(-c3nnc(C(F)F)o3)cn2)C(=O)N1c1ccc(F)cc1F] |
| 15 | 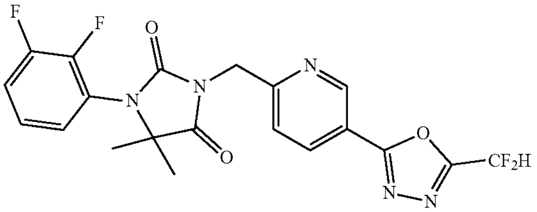 [SMILES: CC1(C)C(=O)N(Cc2ccc(-c3nnc(C(F)F)o3)cn2)C(=O)N1c1cccc(F)c1F] |
| 16 | 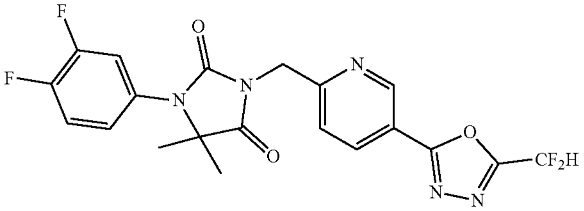 [SMILES: CC1(C)C(=O)N(Cc2ccc(-c3nnc(C(F)F)o3)cn2)C(=O)N1c1ccc(F)c(F)c1] |
| 17 | 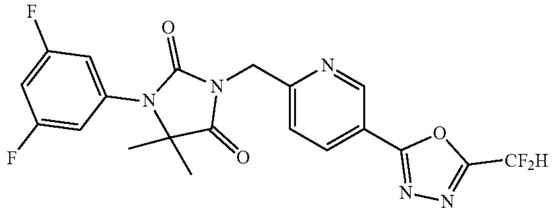 [SMILES: CC1(C)C(=O)N(Cc2ccc(-c3nnc(C(F)F)o3)cn2)C(=O)N1c1cc(F)cc(F)c1] |
| 18 | 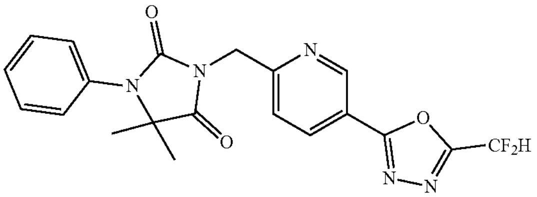 [SMILES: CC1(C)C(=O)N(Cc2ccc(-c3nnc(C(F)F)o3)cn2)C(=O)N1c1ccccc1] |
| 19 | 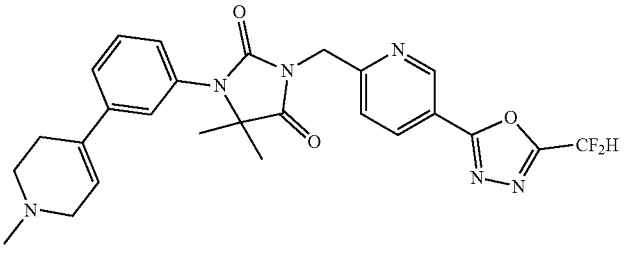 [SMILES: CN1CC=C(c2cccc(N3C(=O)N(Cc4ccc(-c5nnc(C(F)F)o5)cn4)C(=O)C3(C)C)c2)CC1] |

TABLE 1-continued
| Compound | Structure |
|---|---|
| 20 | 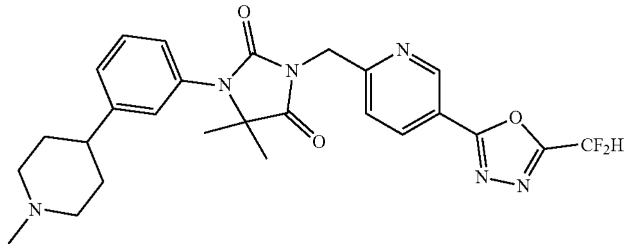 [SMILES: CN1CCC(c2cccc(N3C(=O)N(Cc4ccc(-c5nnc(C(F)F)o5)cn4)C(=O)C3(C)C)c2)CC1] |
| 21 | 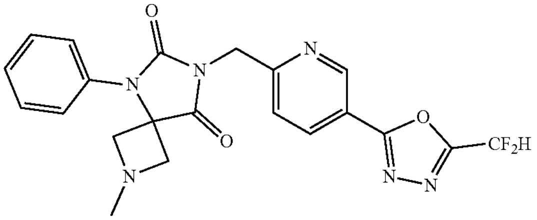 [SMILES: CN1CC2(C1)C(=O)N(Cc1ccc(-c3nnc(C(F)F)o3)cn1)C(=O)N2c1ccccc1] |
| 22 | 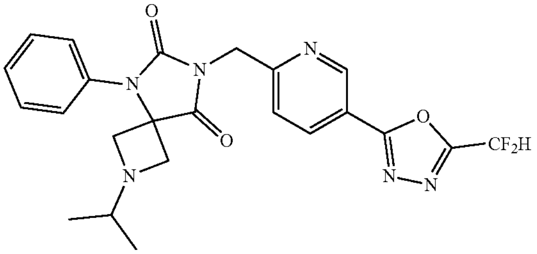 [SMILES: CC(C)N1CC2(C1)C(=O)N(Cc1ccc(-c3nnc(C(F)F)o3)cn1)C(=O)N2c1ccccc1] |
| 23 | 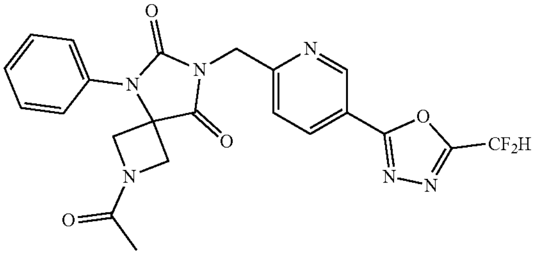 [SMILES: CC(=O)N1CC2(C1)C(=O)N(Cc1ccc(-c3nnc(C(F)F)o3)cn1)C(=O)N2c1ccccc1] |
| 24 | 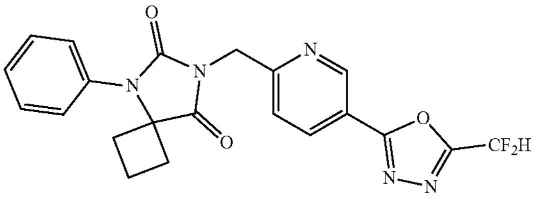 [SMILES: O=C1N(Cc2ccc(-c3nnc(C(F)F)o3)cn2)C(=O)C2(CCC2)N1c1ccccc1] |
| 25 | 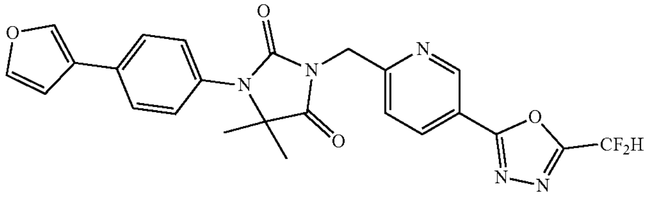 [SMILES: CC1(C)C(=O)N(Cc2ccc(-c3nnc(C(F)F)o3)cn2)C(=O)N1c1ccc(-c2ccoc2)cc1] |

TABLE 1-continued
| Compound | Structure |
|---|---|
| 26 | 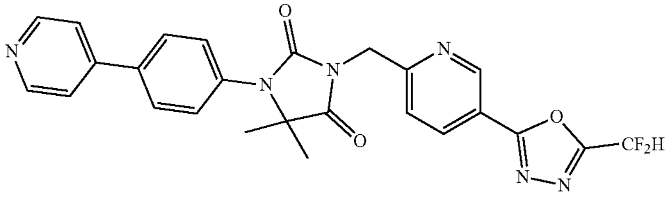 [SMILES: CC1(C)C(=O)N(Cc2ccc(-c3nnc(C(F)F)o3)cn2)C(=O)N1c1ccc(-c2ccncc2)cc1] |
| 27 | 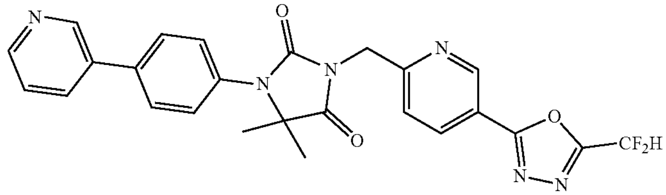 [SMILES: CC1(C)C(=O)N(Cc2ccc(-c3nnc(C(F)F)o3)cn2)C(=O)N1c1ccc(-c2cccnc2)cc1] |
| 28 | 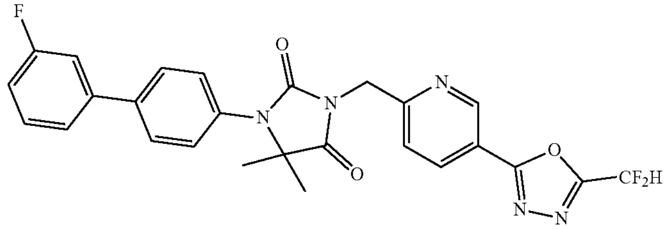 [SMILES: CC1(C)C(=O)N(Cc2ccc(-c3nnc(C(F)F)o3)cn2)C(=O)N1c1ccc(-c2cccc(F)c2)cc1] |
| 29 | 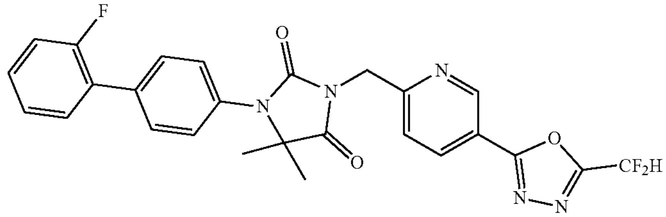 [SMILES: CC1(C)C(=O)N(Cc2ccc(-c3nnc(C(F)F)o3)cn2)C(=O)N1c1ccc(-c2ccccc2F)cc1] |
| 30 | 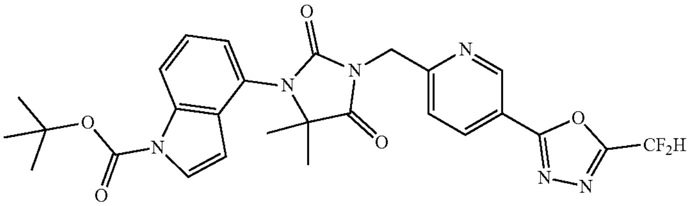 [SMILES: CC(C)(C)OC(=O)n1ccc2c(N3C(=O)N(Cc4ccc(-c5nnc(C(F)F)o5)cn4)C(=O)C3(C)C)cccc21] |
| 31 | 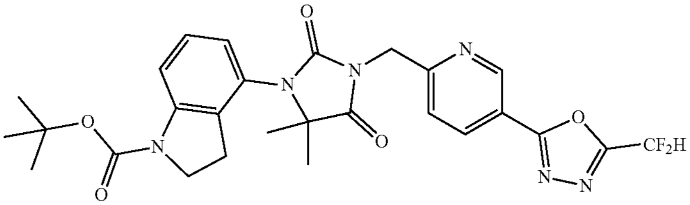 [SMILES: CC(C)(C)OC(=O)N1CCc2c1cccc2N1C(=O)N(Cc2ccc(-c3nnc(C(F)F)o3)cn2)C(=O)C1(C)C] |
| 32 | 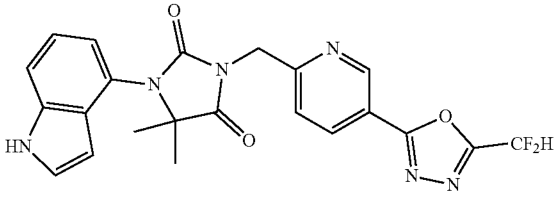 [SMILES: CC1(C)C(=O)N(Cc2ccc(-c3nnc(C(F)F)o3)cn2)C(=O)N1c1cccc2[nH]ccc12] |

TABLE 1-continued

| Compound | Structure |
|---|---|
| 33 | 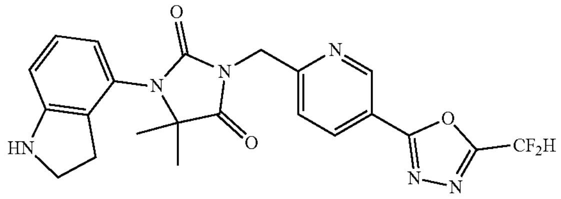 [SMILES: CC1(C)C(=O)N(Cc2ccc(-c3nnc(C(F)F)o3)cn2)C(=O)N1c1cccc2c1CCN2] |
| 34 | 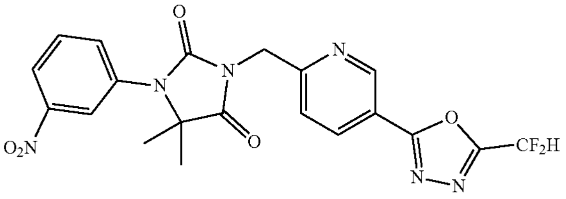 [SMILES: CC1(C)C(=O)N(Cc2ccc(-c3nnc(C(F)F)o3)cn2)C(=O)N1c1cccc([N+](=O)[O-])c1] |
| 35 | 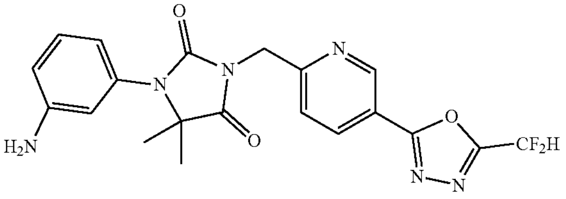 |
| 36 | 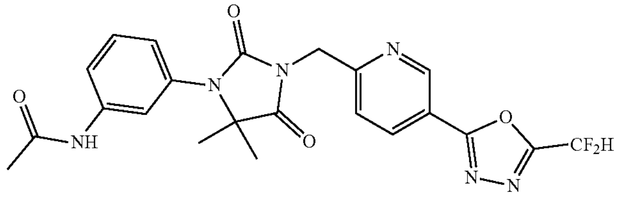 [SMILES: CC(=O)Nc1cccc(N2C(=O)N(Cc3ccc(-c4nnc(C(F)F)o4)cn3)C(=O)C2(C)C)c1] |
| 37 | 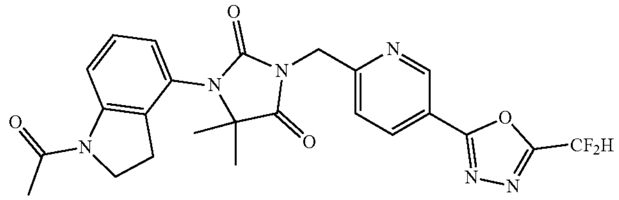 [SMILES: CC(=O)N1CCc2c1cccc2N1C(=O)N(Cc2ccc(-c3nnc(C(F)F)o3)cn2)C(=O)C1(C)C] |

Method for Preparing Compound Represented by Chemical Formula I

The present invention may provide a method for preparing a compound represented by chemical formula I, stereoisomers thereof or pharmaceutically acceptable salts thereof.

A preferable method for preparing the compound represented by chemical formula I, stereoisomers thereof or pharmaceutically acceptable salts thereof is the same as shown in reaction formulas 1, 1-1 and 2 to 7, and even a preparation method modified at a level apparent to those skilled in the art is also included therein.

In each of reaction formulas 1, 1-1 and 2 to 7, $R_1$ to $R_5$, $Z_1$ to $Z_4$, $L_1$, m, n and X are each substantially the same as defined in chemical formula I. In reaction formulas 1, 1-1 and 2 to 7, "halo" may refer to halogen of F, Cl or Br. In addition, in reaction formulas 1, 1-1 and 2 to 7, "PG" may refer to a protecting group of a nitrogen atom and may include tert-butyloxycarbonyl (Boc), benzyloxycarbonyl (Cbz) or the like.

[Reaction Formula 1]

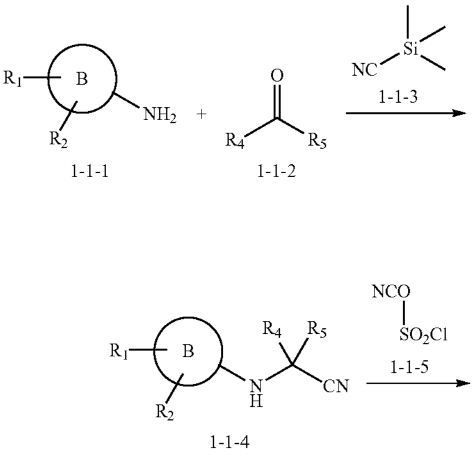

1-1-1
1-1-2
1-1-4

-continued

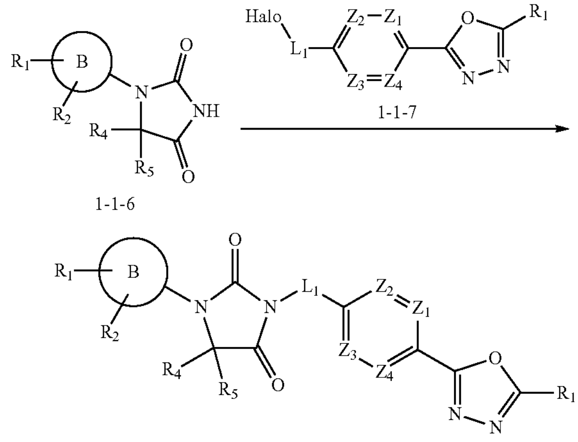

1-1-7

1-1-6

1-1-8

Above reaction formula 1 shows a method for synthesizing a compound having an imidazolidin-2,4-di one structure, in which a compound of chemical formula 1-1-1 may react with a compound of chemical formula 1-1-2 and a compound of chemical formula 1-1-3 so as to prepare a compound of chemical formula 1-1-4 having an aminonitrile structure. After that, the resulting compound may react with a compound of chemical formula 1-1-5 to prepare a compound of chemical formula 1-1-6 having an imidazolidin-2,4-di one structure, and then react with a compound of chemical formula 1-1-7 so as to prepare a compound of chemical formula 1-1-8.

In the present invention, the compound prepared according to above reaction formula 1 may include 3, 4, 9, 10, 11, 12, 13, 14, 15, 16, 17, 18 and the like.

[Reaction Formula 1-1]

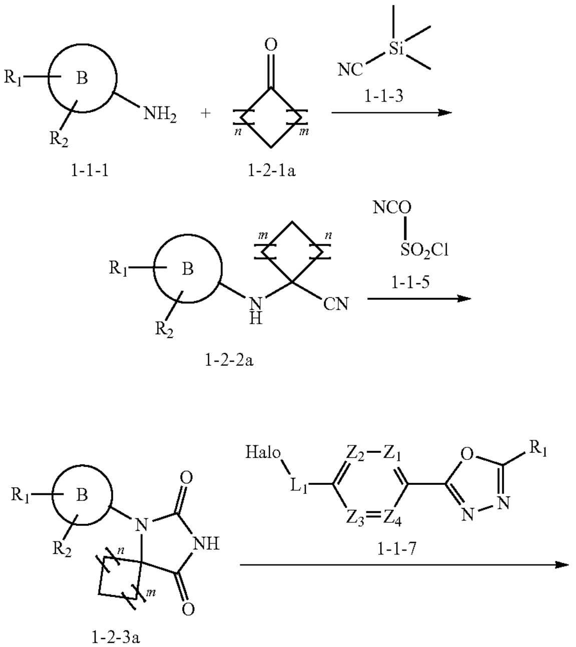

1-1-1 1-2-1a 1-1-3 1-2-2a 1-1-5 1-2-3a 1-1-7

-continued

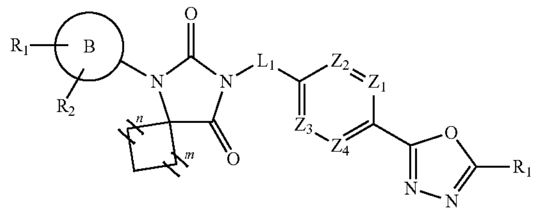

1-2-4a

Above reaction formula 1-1 refers to substantially the same chemical reaction as above reaction formula 1, in which a compound of chemical formula 1-1-1 may react with a compound of chemical formula 1-2-1a and a compound of chemical formula 1-1-3 so as to prepare a compound of chemical formula 1-2-2a. After that, the resulting compound may react with a compound of chemical formula 1-1-5 to prepare a compound of chemical formula 1-2-3a having an imidazolidin-2,4-dione structure, and then react with a compound of chemical formula 1-1-7 so as to prepare a compound of chemical formula 1-2-4a. In the present invention, the compound prepared according to above reaction formula 1-1 may include 24 and the like.

[Reaction Formula 2]

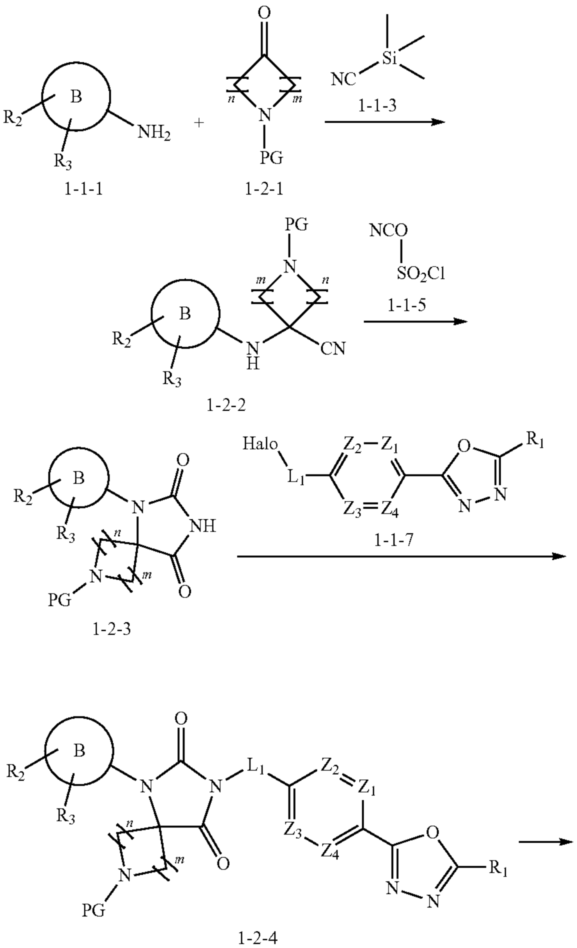

1-1-1 1-2-1 1-1-3 1-2-2 1-1-5 1-2-3 1-1-7 1-2-4

-continued

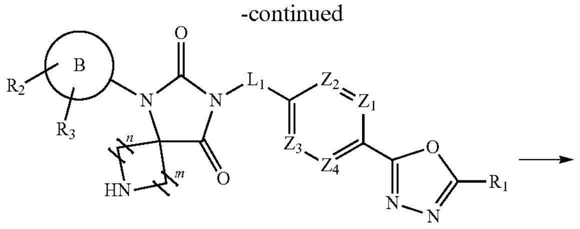

1-2-5

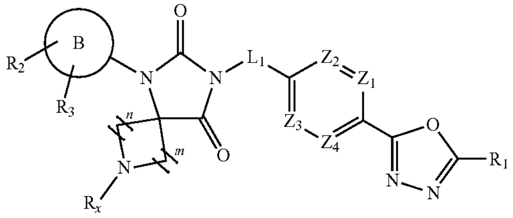

1-2-6

In above reaction formula 2, "$R_x$" may represent C1-C4 alkyl, 4- to 6-membered heterocycloalkyl having one O or C(═O)—(C1-C4 alkyl). Above reaction formula 2 shows a method for synthesizing a compound having an imidazolidin-2,4-dione structure, in which a compound of chemical formula 1-1-1 may react with a compound of chemical formula 1-2-1, to which a protecting group is added, and a compound of chemical formula 1-1-3 so as to prepare a compound of chemical formula 1-2-2 having an aminonitrile structure. After that, the resulting compound may react with a compound of chemical formula 1-1-5 to prepare a compound of chemical formula 1-2-3 having an imidazolidin-2,4-dione structure, and then react with a compound of chemical formula 1-1-7 so as to prepare a compound of chemical formula 1-2-4. A protecting group may be removed from the compound of chemical formula 1-2-4 so as to prepare a compound of chemical formula 1-2-5, and then a reductive amination reaction or a substitution reaction may be performed to prepare a compound of chemical formula 1-2-6.

In the present invention, the compound prepared according to above reaction formula 2 may include 5, 6, 7, 8, 21, 22, 23 and the like.

[Reaction Formula 3]

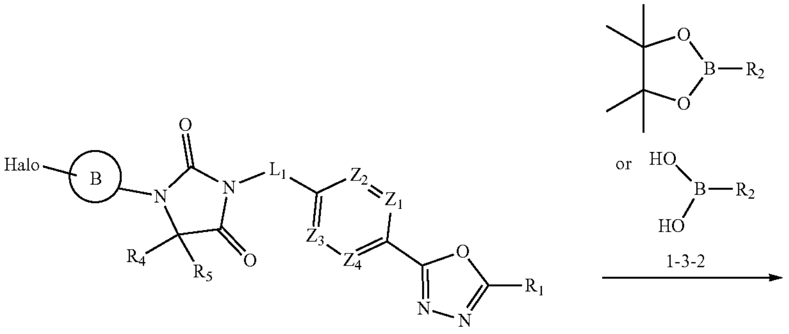

1-3-1

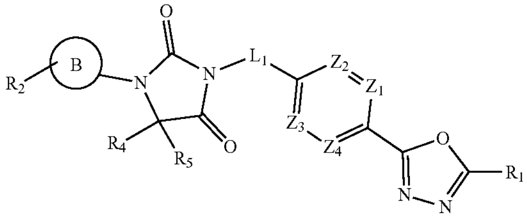

1-3-3

Above reaction formula 3 shows a method for synthesizing a compound having an imidazolidin-2,4-dione structure, in which a compound of chemical formula 1-3-1 prepared in reaction formula 1 may be subjected to C—C coupling (Suzuki reaction) with a compound of chemical formula 1-3-2, so as to prepare a compound of chemical formula 1-3-3.

In the present invention, the compound prepared according to above reaction formula 3 may include 25, 26, 27, 28, 29 and the like.

[Reaction Formula 4]

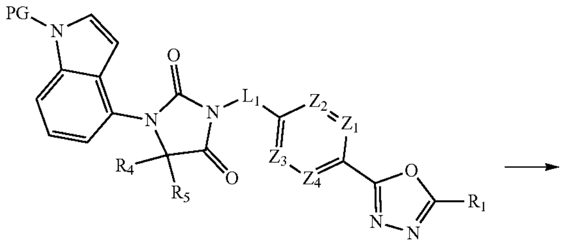

1-4-1

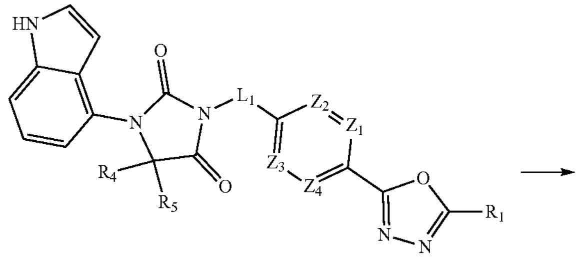

1-4-2

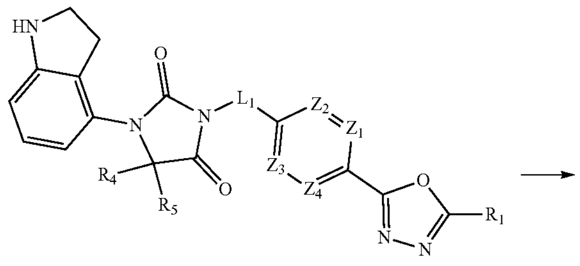

1-4-3

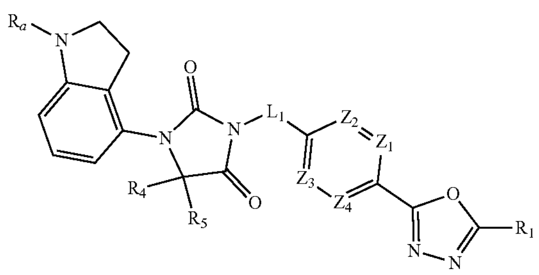

1-4-4

In above reaction formula 4, "$R_a$" may be C(═O)—(C1-C4 alkyl).

Above reaction formula 4 shows a method for synthesizing a compound having an imidazolidin-2,4-dione structure, in which a protecting group may be removed from a compound of chemical formula 1-4-1 having the protecting group, prepared in reaction formula 1, so as to prepare a compound of chemical formula 1-4-2, after which a reduction reaction may be performed to prepare a compound of chemical formula 1-4-3. After that, a reductive amination reaction or a substitution reaction may be performed to prepare a compound of chemical formula 1-4-4.

In the present invention, the compound prepared according to above reaction formula 4 may include 30, 31, 32, 33, 37 and the like.

[Reaction Formula 5]

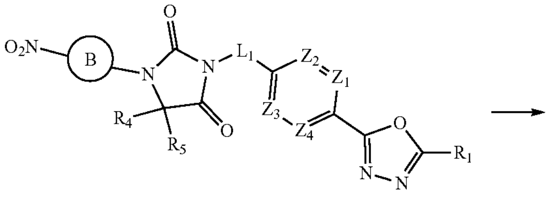

1-5-1

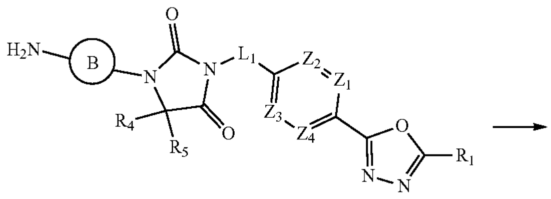

1-5-2

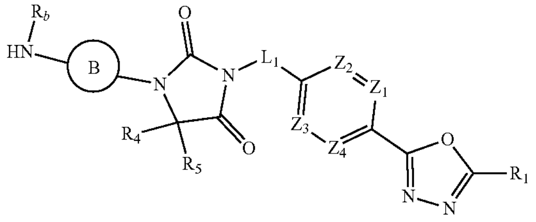

1-5-3

In above reaction formula 5, "$R_b$" may be —C(═)—(C1-C4 alkyl).

Above reaction formula 5 shows a method for synthesizing a compound having an imidazolidin-2,4-dione structure, in which a reduction reaction may be performed with a compound of chemical formula 1-5-1 prepared in reaction formula 1 with the addition of nitro, so as to prepare a compound of chemical formula 1-5-2, after which a reductive amination reaction or a substitution reaction may be performed to prepare a compound of chemical formula 1-5-3.

In the present invention, the compound prepared according to above reaction formula 5 may include 34, 35, 36 and the like.

[Reaction Formula 6]

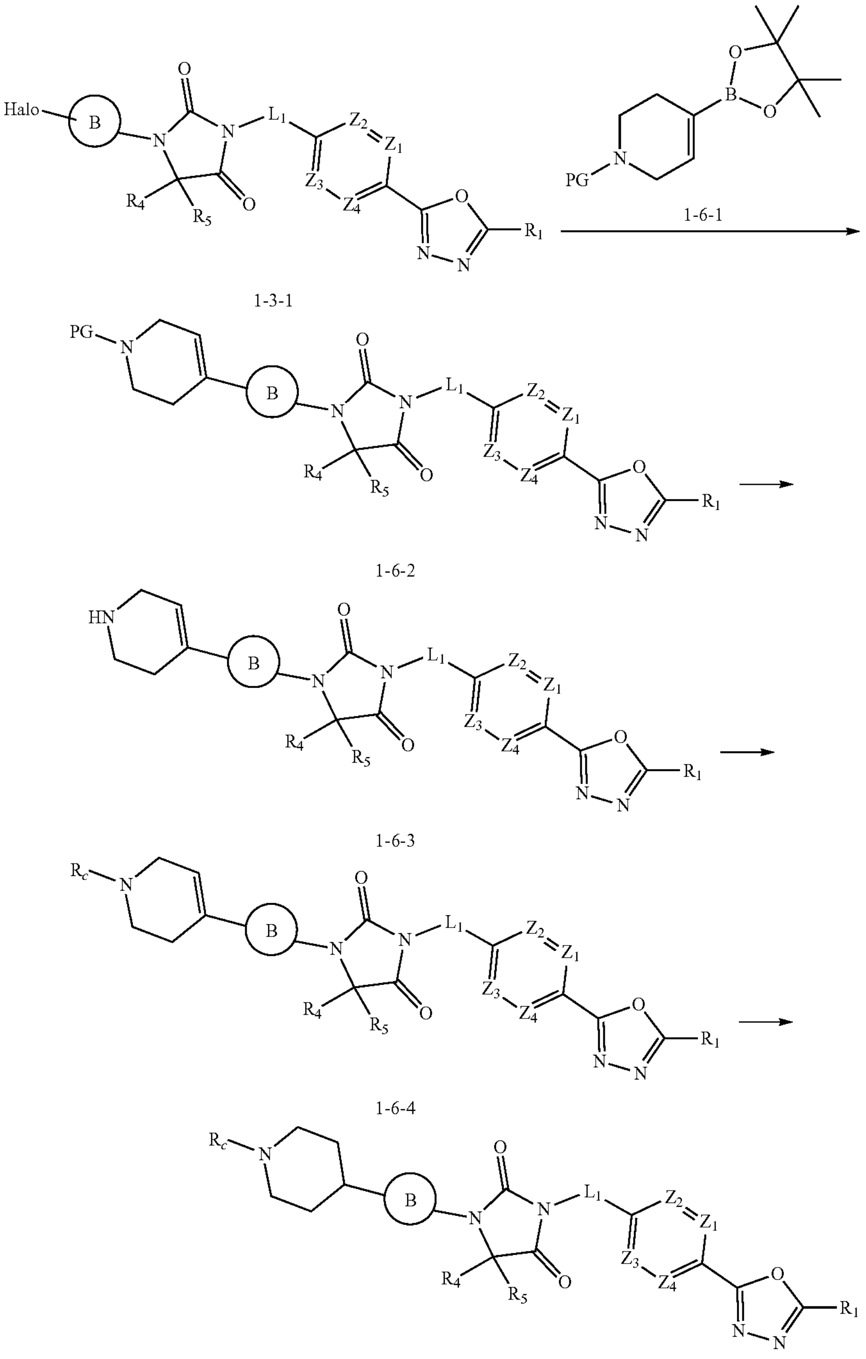

1-3-1, 1-6-1, 1-6-2, 1-6-3, 1-6-4, 1-6-5

In above reaction formula 6, R may be C1-C4 alkyl.

Above reaction formula 6 shows a method for synthesizing a compound having an imidazolidin-2,4-di one structure, in which a compound of chemical formula 1-3-1 prepared in reaction formula 1 may be subjected to C—C coupling (Suzuki reaction) with a compound of chemical formula 1-6-1 having a protecting group so as to prepare a compound of chemical formula 1-6-2. A protecting group may be removed from the compound of chemical formula 1-6-2 so as to prepare a compound of chemical formula 1-6-3, and then a reductive amination reaction or a substitution reaction may be performed to prepare a compound of chemical formula 1-6-4. After that, a reduction reaction may be performed to prepare a compound of chemical formula 1-6-5.

In the present invention, the compound prepared according to above reaction formula 6 may include 19, 20 and the like.

[Reaction Formula 7]

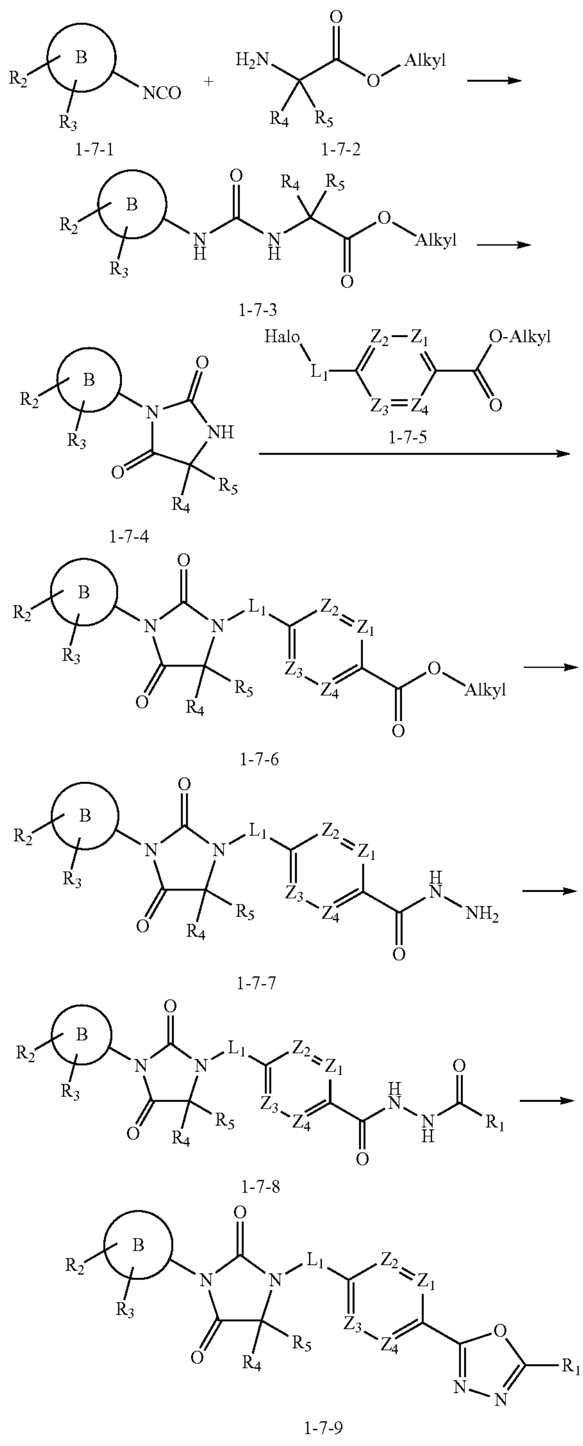

1-7-1 1-7-2 1-7-3 1-7-4 1-7-5 1-7-6 1-7-7 1-7-8 1-7-9

In above reaction formula 7, alkyl may be C1-C4 alkyl.

Above reaction formula 7 shows a method for synthesizing a compound having an imidazolidin-2,4-di one structure, in which a compound of chemical formula 1-7-1 may react with a compound of chemical formula 1-7-2 to prepare a compound of chemical formula 1-7-3, and a cyclization reaction may be performed to prepare a compound of chemical formula 1-7-4. A compound of chemical formula 1-7-6 may be prepared through a substitution reaction between a compound of chemical formula 1-7-4 and a compound of chemical formula 1-7-5, after which the compound of chemical formula 1-7-6 may react with hydrazine to prepare a compound of chemical formula 1-7-7, and then react with difluoroacetic anhydride and trifluoroacetic anhydride to prepare a compound of chemical formula 1-7-8. After that, the compound of chemical formula 1-7-8 may be subjected to a cyclization reaction with a Burgess reagent to prepare a compound of chemical formula 1-7-9.

In the present invention, the compound prepared according to above reaction formula 7 may include 1, 2 and the like.

Composition Containing Compound Represented by Chemical Formula I, Use Thereof and Therapeutic Method Using the Same The present invention may provide a pharmaceutical composition for preventing or treating histone deacetylase (HDAC)-mediated diseases, containing a compound represented by above chemical formula I, stereoisomers thereof or pharmaceutically acceptable salts thereof as an effective ingredient. Preferably, the present invention may provide a pharmaceutical composition for preventing or treating HDAC6 activity-related diseases. Above chemical formula I is the same as defined above.

The pharmaceutical composition of the present invention may selectively inhibit HDAC6, thereby showing a remarkable effect on preventing or treating histone deacetylase 6 activity-related diseases.

The histone deacetylase (HDAC)-mediated diseases, specifically HDAC6 activity-related diseases may include infectious diseases such as prion disease; neoplasm such as benign tumor (for example, myelodysplastic syndrome) or malignant tumor (for example, multiple myeloma, lymphoma, leukemia, lung cancer, colorectal cancer, colon cancer, prostate cancer, urothelial carcinoma, breast cancer, melanoma, skin cancer, liver cancer, brain cancer, stomach cancer, ovarian cancer, pancreatic cancer, head and neck cancer, oral cancer or glioma); endocrinopathy, nutritional and metabolic diseases such as Wilson's disease, amyloidosis or diabetes; mental and behavioral disorders such as depression or rett syndrome; neurological diseases such as central nervous system atrophy (for example, Huntington's disease, spinal muscular atrophy (SMA), spinocerebellar ataxia (SCA)), neurodegenerative disease (for example, Alzheimer's disease), motor disorder (for example, Parkinson's disease), neuropathy (for example, hereditary neuropathy (Charcot-Marie-Tooth disease), sporadic neuropathy, inflammatory neuropathy, drug-induced neuropathy), motor neuropathy (for example, amyotrophic lateral sclerosis (ALS)), central nervous system demyelinating disease (for example, multiple sclerosis (MS)), or the like; eye and ocular adnexal diseases such as uveitis; circulatory diseases such as atrial fibrillation, stroke or the like; respiratory diseases such as asthma; digestive diseases such as alcoholic liver disease, inflammatory bowel disease, Crohn's disease, ulcerative bowel disease or the like; skin and subcutaneous tissue diseases such as psoriasis; musculoskeletal system and connective tissue diseases such as rheumatoid arthritis, osteoarthritis, systemic lupus erythematosis (SLE) or the like; or teratosis, deformities and chromosomal aberration such as autosomal dominant polycystic kidney disease, and also may include other symptoms or diseases related to abnormal functions of histone deacetylase.

The pharmaceutically acceptable salts are the same as described in the pharmaceutically acceptable salts of the compound of the present invention.

For administration, the pharmaceutical composition of the present invention may further contain at least one type of a pharmaceutically acceptable carrier, in addition to the compound, stereoisomers thereof or pharmaceutically acceptable salts thereof. The pharmaceutically acceptable carrier used may include saline solution, sterilized water, Ringer's solution, buffered saline, dextrose solution, maltodextrin solution, glycerol, ethanol and a mixture of at least one ingredient thereof, and other conventional additives such as antioxidants, buffer solutions, bacteriostatic agents, etc., may be added thereto, if needed. In addition, diluents, dispersing agents, surfactants, binders and lubricants may be added to be formulated into injectable dosage forms such as aqueous solutions, suspensions, emulsions, etc., pills, capsules, granules or tablets. Thus, the composition of the present invention may be patches, liquid medicines, pills, capsules, granules, tablets, suppositories, etc. Such preparations may be prepared according to a conventional method used for formulation in the art or a method disclosed in Remington's Pharmaceutical Science (latest edition), Mack Publishing Company, Easton PA, and such composition may be formulated into various preparations depending on each disease or component.

The composition of the present invention may be orally or parenterally administered (for example, applied intravenously, hypodermically, intraperitoneally or locally) according to a targeted method, in which a dosage thereof varies in a range thereof depending on a patient's weight, age, gender, health condition and diet, an administration time, an administration method, an excretion rate, a severity of a disease and the like. A daily dosage of the compound of the present invention, stereoisomers thereof or pharmaceutically acceptable salts thereof may be about 1 to 1000 mg/kg, preferably 5 to 100 mg/kg, and may be administered at one time a day or several times a day by dividing the daily dosage of the compound.

The pharmaceutical composition of the present invention may further contain at least one effective ingredient, which shows the same or similar medicinal effect, in addition to the compound, stereoisomers thereof or pharmaceutically acceptable salts thereof.

The present invention may provide a method for preventing or treating histone deacetylase (HDAC)-mediated diseases, including administering a therapeutically effective amount of the compound represented by above chemical formula I, stereoisomers thereof or pharmaceutically acceptable salts thereof; or a pharmaceutical composition containing the same as an effective ingredient into a subject in need thereof. The histone deacetylase (HDAC)-mediated diseases may be HDAC6 activity-related diseases.

As used herein, the term "therapeutically effective amount" may refer to an amount of the compound, stereoisomers thereof or pharmaceutically acceptable salts thereof, which are effective in preventing or treating histone deacetylase (HDAC)-mediated diseases, specifically HDAC6 activity-related diseases.

In the present invention, the term "subject" may refer to mammals including humans, and the term "administration" may refer to providing a predetermined material to a subject through any appropriate method. It is apparent to those skilled in the art that the therapeutically effective dosage and the number of administration for effective ingredient of the present invention may vary depending on a desired effect.

In the present invention, the term "prevention" may refer to a delay of occurrence of disease, disorder or condition. If the occurrence of disease, disorder or condition is delayed for an expected period of time, the prevention may be considered as complete.

In the present invention, the term "treatment" may refer to the one that partially or completely reduces, ameliorates, alleviates, inhibits or delays the occurrence of a certain disease, disorder and/or condition, reduces a severity thereof, or reduces the occurrence of at least one symptom or property thereof.

In addition, the present invention may provide a method for selectively inhibiting HDAC6 by administering a therapeutically effective amount of the compound represented by above chemical formula I, stereoisomers thereof or pharmaceutically acceptable salts thereof; or a pharmaceutical composition containing the same as an effective ingredient into mammals including humans.

The method for preventing or treating histone deacetylase (HDAC)-mediated diseases, specifically HDAC6 activity-related diseases according to the present invention may include not only dealing with the diseases themselves before expression of their symptoms, but also inhibiting or avoiding such symptoms by administering the compound, stereoisomers thereof or pharmaceutically acceptable salts thereof. In managing the disease, a preventive or therapeutic dose of a certain active ingredient may vary depending on a nature and severity of the disease or condition and a route of administering the active component. A dose and a frequency thereof may vary depending on an individual patient's age, weight and reactions. A suitable dose and usage may be easily selected by those skilled in the art, naturally considering such factors. In addition, the method for preventing or treating histone deacetylase (HDAC)-mediated diseases, specifically HDAC6 activity-related diseases according to the present invention may further include administering a therapeutically effective amount of an additional active agent, which is helpful in treating the diseases, along with the compound represented by above chemical formula I, and the additional active agent may exhibit a synergy effect or an additive effect together with the compound, stereoisomers thereof or pharmaceutically acceptable salts thereof.

The present invention may also provide a use of the compound represented by chemical formula I, stereoisomers thereof or pharmaceutically acceptable salts thereof; or a pharmaceutical composition containing the same as an effective ingredient for preventing or treating histone deacetylase (HDAC)-mediated diseases. The histone deacetylase (HDAC)-mediated diseases may be HDAC6 activity-related diseases.

The present invention may also provide a use of the compound represented by above chemical formula I, stereoisomers thereof or pharmaceutically acceptable salts thereof; or a pharmaceutical composition containing the same as an effective ingredient in preparation of a medicament for preventing or treating histone deacetylase (HDAC)-mediated diseases. The histone deacetylase (HDAC)-mediated diseases may be HDAC6 activity-related diseases.

For preparing a medicament, the compound, stereoisomers thereof or pharmaceutically acceptable salts thereof may be combined with acceptable adjuvants, diluents, carriers, etc., and may be prepared into a complex preparation together with other active agents and thus have a synergy action of active components.

Matters mentioned in the use, composition and therapeutic method of the present invention are equally applied, if not contradictory to each other.

Advantageous Effects

According to the present invention, the compound represented by above chemical formula I, stereoisomers thereof or pharmaceutically acceptable salts thereof have not only an HDAC6 inhibitory activity, but also a remarkably excellent effect of preventing or treating HDAC6 activity-related diseases by selectively inhibiting HDAC6.

Also, the inventive compound having a selective HDAC6 inhibitory activity, stereoisomers thereof or pharmaceutically acceptable salts thereof can be advantageously used to prevent or treat HDAC6 activity-related diseases such as cancers, inflammatory diseases, autoimmune diseases, neurological diseases or neurodegenerative disorders, etc.

BEST MODE FOR INVENTION

Hereinafter, the present invention will be described in more detail through the following examples and experimental examples. However, those examples are provided only for the purpose of illustrating the present invention, and thus the scope of the present invention is not limited thereto.

Preparation of Compound

A specific method for preparing the compound represented by chemical formula I is the same as follows.

Example 1: Synthesis of Compound 1, 1-(4-(5-(difluoromethyl)-1,3,4-oxadiazol-2-yl)-2-fluorobenzyl)-5,5-dimethyl-3-phenylimidazolidin-2,4-dione

[Step 1] Synthesis of N'-(2,2-difluoroacetyl)-4-((5,5-dimethyl-2,4-dioxo-3-phenylimidazolidin-1-yl)methyl)-3-fluorobenzohydrazide

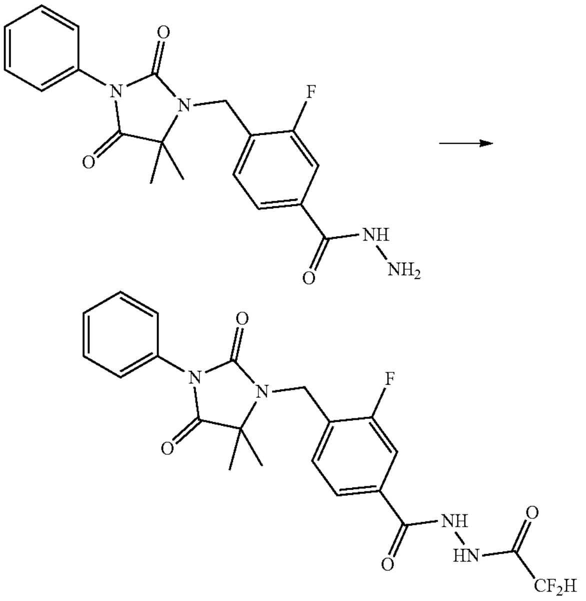

The 4-((5,5-dimethyl-2,4-dioxo-3-phenylimidazolidin-1-yl)methyl)-3-fluorobenzohydrazide (0.119 g, 0.321 mmol) and triethylamine (0.067 mL, 0.482 mmol) were dissolved in dichloromethane (4 mL) at room temperature, after which 2,2-difluoroacetic anhydride (0.036 mL, 0.289 mmol) was added to the resulting solution and stirred at the same temperature. Solvent was removed from the reaction mixture under reduced pressure, after which the resulting concentrate was purified via column chromatography ($SiO_2$, 4 g cartridge; ethyl acetate/hexane=20 to 70%) and concentrated to obtain a title compound (0.053 g, 36.8%) in a colorless oil form.

[Step 2] Synthesis of Compound 1

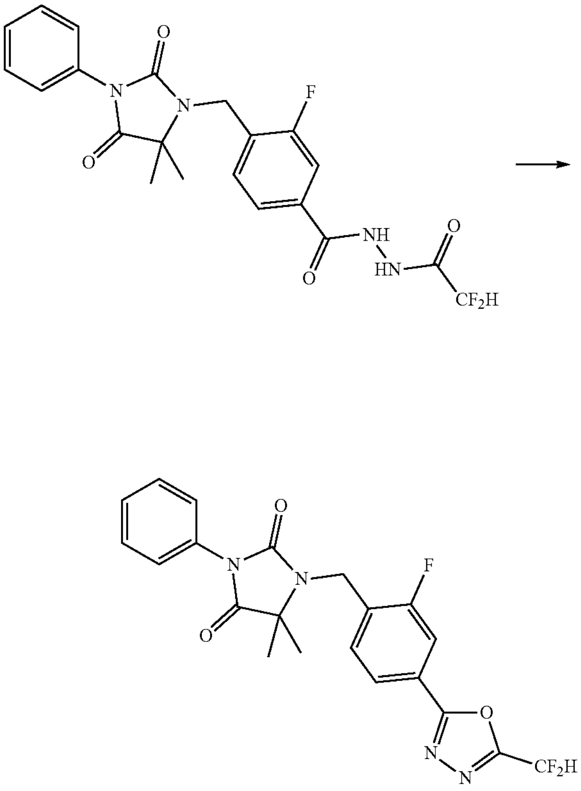

The N'-(2,2-difluoroacetyl)-4-((5,5-dimethyl-2,4-dioxo-3-phenylimidazolidin-1-yl)methyl)-3-fluorobenzohydrazide (0.053 g, 0.118 mmol) prepared in step 1 and 1-methoxy-N-triethylammoniosulfonyl-methanimidate (Burgess reagent, 0.042 g, 0.177 mmol) were mixed in tetrahydrofuran (4 mL) at room temperature, after which the resulting mixture was irradiated with microwave, then heated at 150° C. for 30 minutes, and then a reaction was finished by lowering a temperature to room temperature. Solvent was removed from the reaction mixture under reduced pressure, after which water was poured into the resulting concentrate, and then an extraction was performed with ethyl acetate. An organic layer was washed with saturated hydrogen carbonate aqueous solution, dehydrated with anhydrous magnesium sulfate, filtered, and concentrated under reduced pressure. The resulting concentrate was purified via column chromatography ($SiO_2$, 4 g cartridge; ethyl acetate/hexane=0 to 40%) and concentrated to obtain a title compound (0.009 g, 17.7%) in a colorless oil form.

$^1H$ NMR (400 MHz, $CDCl_3$) δ 7.94 (d, J=8.2 Hz, 1H), 7.88 (d, J=10.0 Hz, 1H), 7.53~7.47 (m, 4H), 7.43~7.39 (m, 1H), 6.95 (t, J=51.6 Hz, 1H), 4.77 (s, 2H); LRMS (ES) m/z 431.0 ($M^+$+1).

Synthesis of Compound 2, 1-(2-fluoro-4-(5-(trifluoromethyl)-1,3,4-oxadiazol-2-yl)benzyl)-5,5-dimethyl-3-phenylimidazolidin-2,4-dione

[Step 1] Synthesis of methyl 2-methyl-2-(3-phenylureido)propanoate

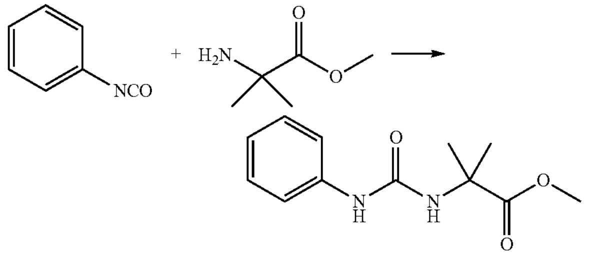

Isocyanatobenzene (1.000 g, 8.395 mmol), methyl 2-amino-2-methylpropanoate (1.418 g, 9.234 mmol) and triethylamine (1.280 mL, 9.234 mmol) were dissolved in dichloromethane (10 mL) at room temperature, after which the resulting solution was stirred at the same temperature for 8 hours. Solvent was removed from the reaction mixture under reduced pressure, after which an obtained product was used without an additional purification process (1.900 g, 95.8%, white solid).

[Step 2] Synthesis of 5,5-dimethyl-3-phenylimidazolidin-2,4-dione

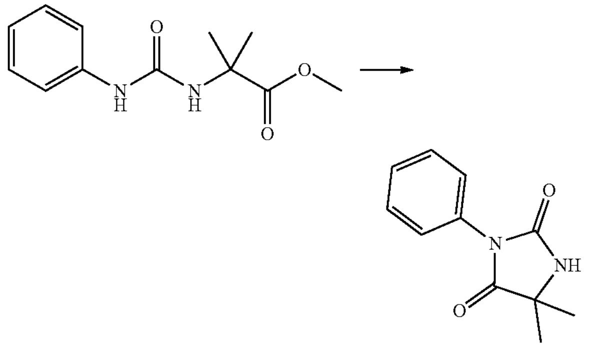

The methyl 2-methyl-2-(3-phenylureido)propanoate (1.900 g, 8.028 mmol) prepared in step 1 and 4M hydrochloric acid aqueous solution (4.00 M solution in dioxane, 8.028 mL, 32.112 mmol) were dissolved in methanol (20 mL) at room temperature, after which the resulting solution was stirred at the same temperature for 12 hours. Water was poured into the reaction mixture and an extraction was performed with ethyl acetate. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 12 g cartridge; ethyl acetate/hexane=0 to 30%) and concentrated to obtain a desired title compound (1.300 g, 79.3%) in a white solid form.

[Step 3] Synthesis of methyl 4-((5,5-dimethyl-2,4-dioxo-3-phenylimidazolidin-1-yl)methyl)-3-fluorobenzoate

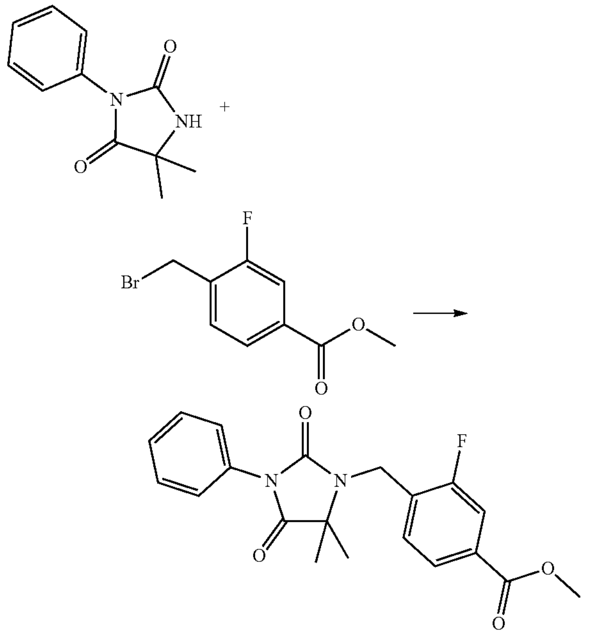

The 5,5-dimethyl-3-phenylimidazolidin-2,4-dione (0.413 g, 2.022 mmol) prepared in step 2 was dissolved in N,N-dimethylformamide (15 mL) at 0° C., after which sodium hydride (0.073 g, 3.033 mmol) was added into the resulting solution, and stirred at the same temperature for 30 minutes. Methyl 4-(bromomethyl)-3-fluorobenzoate (0.500 g, 2.022 mmol) was added into the reaction mixture and further stirred at room temperature for 12 hours. Water was poured into the reaction mixture and an extraction was performed with ethyl acetate. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 12 g cartridge; ethyl acetate/hexane=0 to 30%), and concentrated to obtain a desired title compound (0.265 g, 35.4%) in a colorless oil form.

[Step 4] Synthesis of 4-((5,5-dimethyl-2,4-dioxo-3-phenylimidazolidin-1-yl)methyl)-3-fluorobenzohydrazide

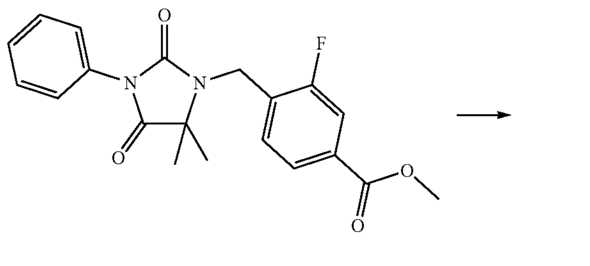

-continued

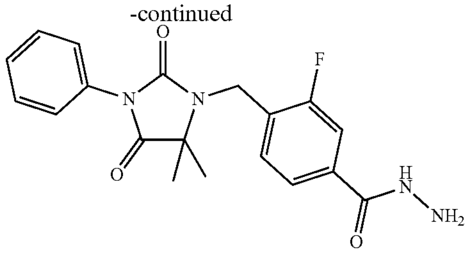

The methyl 4-((5,5-dimethyl-2,4-dioxo-3-phenylimidazolidin-1-yl)methyl)-3-fluorobenzoate (0.265 g, 0.715 mmol) prepared in step 3 and hydrazine monohydrate (0.676 mL, 14.310 mmol) were mixed in ethanol (10 mL), then heated at 120° C. for one hour by irradiation with microwaves, and then a reaction was finished by lowering a temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, dehydrated with anhydrous magnesium sulfate, filtered, and concentrated under reduced pressure. An obtained product was used without an additional purification process (0.220 g, 83.0%, white foamy solid).

[Step 5] Synthesis of 4-((5,5-dimethyl-2,4-dioxo-3-phenylimidazolidin-1-yl)methyl)-3-fluoro-N'-(2,2,2-trifluoroacetyl)benzohydrazide

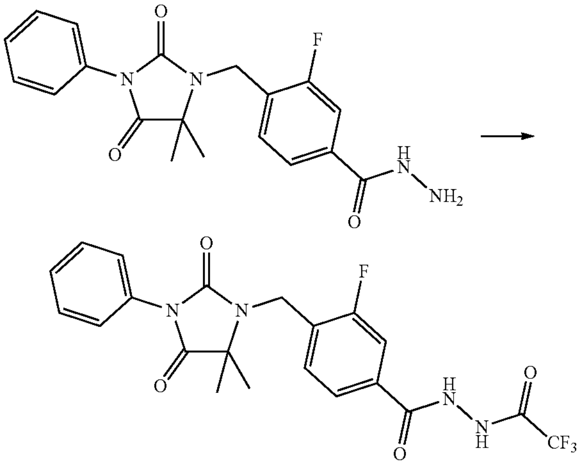

The 4-((5,5-dimethyl-2,4-dioxo-3-phenylimidazolidin-11-yl)methyl)-3-fluorobenzohydrazide (0.108 g, 0.292 mmol) prepared in step 4, trifluoroacetic anhydride (0.037 mL, 0.262 mmol) and triethylamine (0.061 mL, 0.437 mmol) were dissolved in dichloromethane (10 mL) at room temperature, after which the resulting solution was stirred at the same temperature for one hour. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 12 g cartridge; dichloromethane/dichloromethane=0 to 10%) and concentrated to obtain a desired title compound (0.084 g, 61.8%) in a colorless oil form.

[Step 6] Synthesis of Compound 2

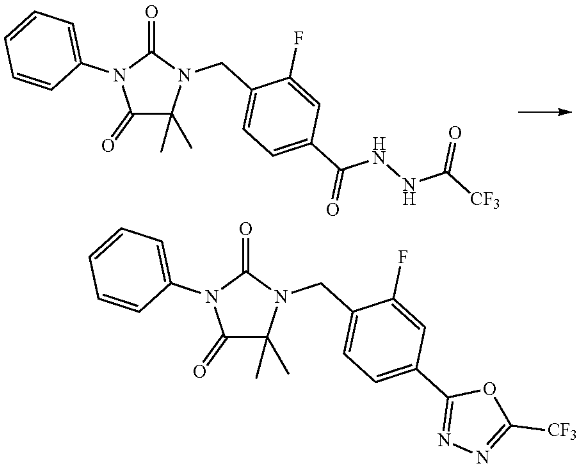

The 4-((5,5-dimethyl-2,4-dioxo-3-phenylimidazolidin-1-yl)methyl)-3-fluoro-N'-(2,2,2-trifluoroacetyl)benzohydrazide (0.084 g, 0.180 mmol) prepared in step 5 and 1-methoxy-N-triethylammoniosulfonyl-methanimidate (Burgess reagent, 0.064 g, 0.270 mmol) were mixed in tetrahydrofuran (10 mL), after which the resulting mixture was irradiated with microwave, then heated at 150° C. for 30 minutes, and then a reaction was finished by lowering a temperature to room temperature. Water was poured into the reaction mixture and an extraction was performed with ethyl acetate. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 12 g cartridge; ethyl acetate/hexane=0 to 50%), and concentrated to obtain a desired compound (0.040 g, 49.5%) in a colorless oil form.

$^1$H NMR (400 MHz, $CDCl_3$) δ 7.95~7.92 (m, 1H), 7.88 (dd, J=9.9, 1.5 Hz, 1H), 7.78 (t, J=7.7 Hz, 1H), 7.54~7.38 (m, 5H), 4.77 (s, 2H), 1.48 (s, 9H).

Synthesis of Compound 3, 3-(4-(5-(difluoromethyl)-1,3,4-oxadiazol-2-yl)-2-fluorobenzyl)-1-phenylimidazolidin-2,4-dione

[Step 1] Synthesis of 4-((2,5-dioxo-3-phenylimidazolidin-1-yl)methyl)-3-fluorobenzohydrazide

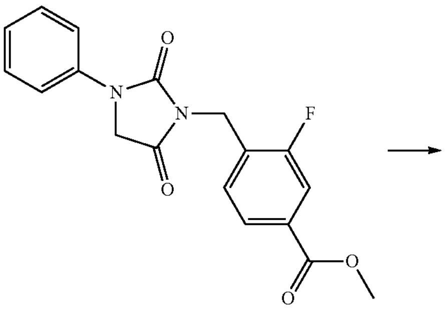

-continued

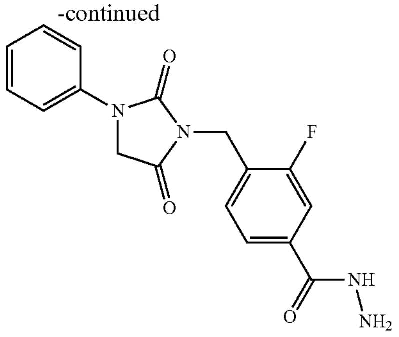

Methyl 4-((4,4-dimethyl-2,5-dioxo-3-phenylimidazolidin-1-yl)methyl)-3-fluorobenzoate (0.175 g, 0.511 mmol) and hydrazine monohydrate (0.497 mL, 10.224 mmol) were dissolved in ethanol (3 mL) at room temperature, after which the resulting solution was stirred at 120° C. for one hour, and then a reaction was finished by lowering a temperature to room temperature. A precipitated solid was filtered, washed with ethanol, and dried to obtain a title compound (0.100 g, 57.1%) in a white solid form.

[Step 2] Synthesis of N'-(2,2-difluoroacetyl)-4-((2,5-dioxo-3-phenylimidazolidin-1-yl)methyl)-3-fluorobenzohydrazide

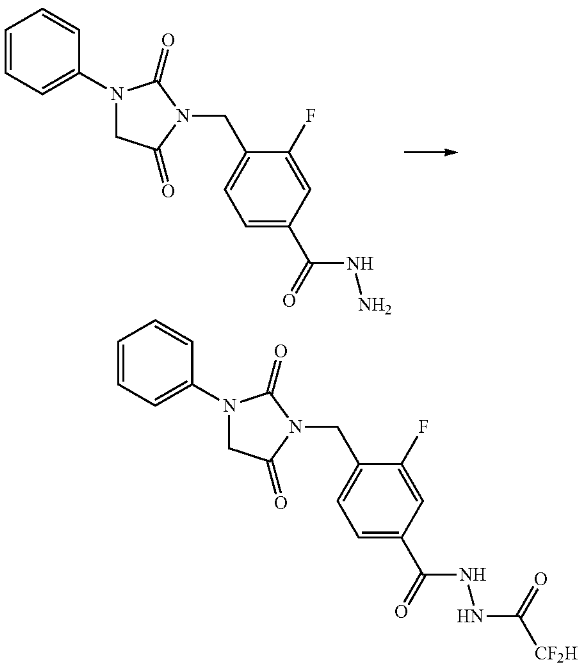

The 4-((2,5-dioxo-3-phenylimidazolidin-1-yl)methyl)-3-fluorobenzohydrazide (0.100 g, 0.292 mmol) prepared in step 1 and triethylamine (0.061 mL, 0.438 mmol) were dissolved in dichloromethane (10 mL) at room temperature, after which 2,2-difluoroacetic anhydride (0.029 mL, 0.263 mmol) was added to the resulting solution and stirred at the same temperature for 17 hours. A precipitated solid was filtered, washed with dichloromethane, and dried to obtain a title compound (0.100 g, 81.4%) in a white solid form.

[Step 3] Synthesis of Compound 3

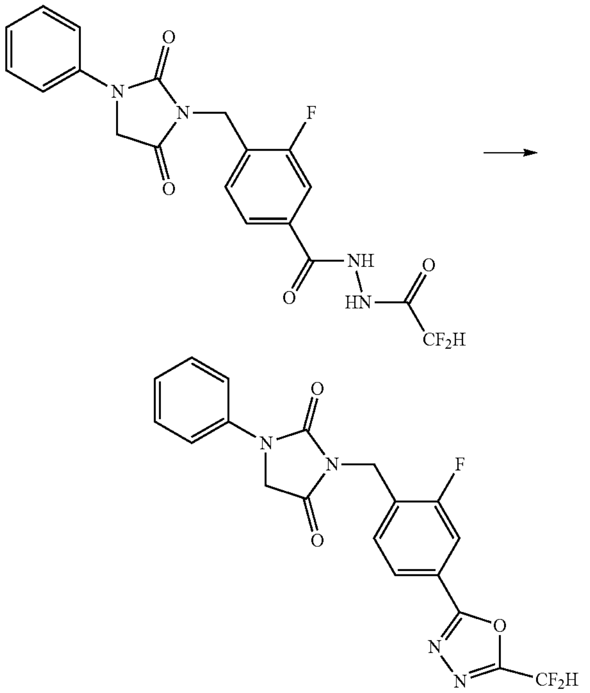

The N'-(2,2-difluoroacetyl)-4-((2,5-dioxo-3-phenylimidazolidin-1-yl)methyl)-3-fluorobenzohydrazide (0.100 g, 0.238 mmol) prepared in step 2 and 1-methoxy-N-triethylammoniosulfonyl-methanimidate (Burgess reagent, 0.085 g, 0.357 mmol) were mixed in tetrahydrofuran (3 mL) at room temperature, after which the resulting mixture was irradiated with microwave, then heated at 150° C. for 30 minutes, and then a reaction was finished by lowering a temperature to room temperature. Solvent was removed from the reaction mixture under reduced pressure, after which water was poured into the resulting concentrate, and an extraction was performed with dichloromethane, filtered via a plastic filter to remove a solid residue and an aqueous solution layer therefrom, and concentrated under reduced pressure. The resulting concentrate was purified via column chromatography ($SiO_2$, 4 g cartridge; ethyl acetate/hexane=5 to 70%), and concentrated to obtain a title compound (0.019 g, 19.9%) in a white solid form.

$^1H$ NMR (400 MHz, $CDCl_3$) δ 7.89 (dd, J=4.8, 1.3 Hz, 1H), 7.87 (t, J=2.2 Hz, 1H), 7.69~7.38 (m, 6H), 7.14 (t, J=7.4 Hz, 1H), 4.79 (s, 2H), 4.61 (s, 2H).

Synthesis of Compound 4, 3-((5-(5-(difluoromethyl)-1,3,4-oxadiazol-2-yl)pyridin-2-yl)methyl)-1-phenylimidazolidin-2,4-dione

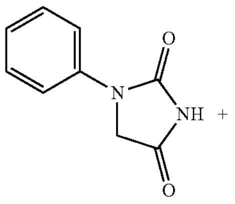

-continued

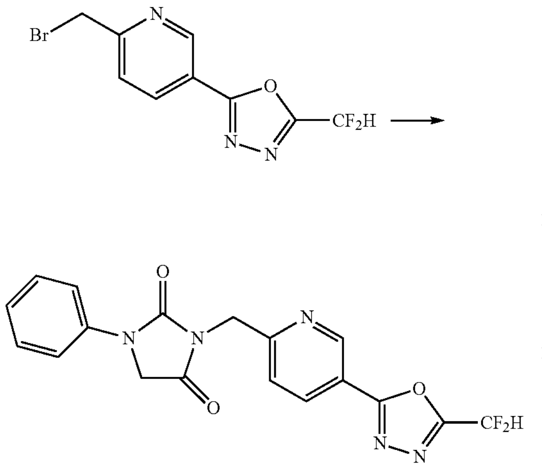

The 1-phenylimidazolidin-2,4-dione (0.200 g, 1.135 mmol) was dissolved in N,N-dimethylformamide (10 mL) at 0° C., after which sodium hydride (60.00%, 0.068 g, 1.703 mmol) was added into the resulting solution, and stirred at the same temperature for 30 minutes. 2-(6-(bromomethyl)pyridin-3-yl)-5-(difluoromethyl)-1,3,4-oxadiazole (0.329 g, 1.135 mmol) was added into the reaction mixture and further stirred at room temperature for three hours. Water was poured into the reaction mixture and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain a title compound (0.100 g, 22.9%) in a white solid form.

$^1H$ NMR (400 MHz, $CDCl_3$) δ 9.27~9.26 (m, 1H), 8.39 (dd, J=8.2, 2.2 Hz, 1H), 7.61 (dd, J=7.8, 1.1 Hz, 2H), 7.54 (dd, J=8.2, 0.7 Hz, 1H), 7.44~7.40 (m, 2H), 7.20~7.18 (m, 1H), 7.08 (s, 0.25H), 6.95 (s, 0.5H), 6.82 (s, 0.25H), 5.03 (s, 2H), 4.47 (s, 2H); LRMS (ES) m/z 386.4 ($M^+$+1).

Synthesis of Compound 5, tert-butyl 3-((5-(5-(difluoromethyl)-1,3,4-oxadiazol-2-yl)pyridin-2-yl)methyl)-1-(3-fluorophenyl)-2,4-dioxo-1,3,8-triazaspiro[4.5]decan-8-carboxylate

[Step 1] Synthesis of tert-butyl 4-((3-(4-(5-(difluoromethyl)-1,3,4-oxadiazol-2-yl)-2-fluorobenzyl)-3-phenylureido)methyl)piperidin-1-carboxylate

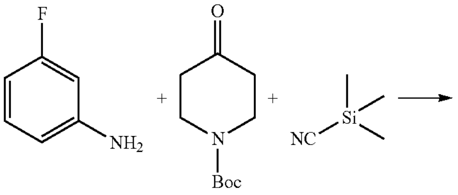

-continued

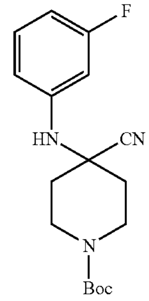

The 3-fluoroaniline (1.000 g, 8.999 mmol), tert-butyl 4-oxopiperidin-1-carboxylate (1.793 g, 8.999 mmol) and trimethylsilacarbonitrile (0.893 g, 8.999 mmol) were dissolved in acetic acid (30 mL), after which the resulting solution was stirred at 0° C. for 30 minutes and further stirred at room temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain a title compound (1.850 g, 64.4%) in a white solid form.

[Step 2] Synthesis of tert-butyl 1-(3-fluorophenyl)-2,4-dioxo-1,3,8-triazaspiro[4.5]decan-8-carboxylate

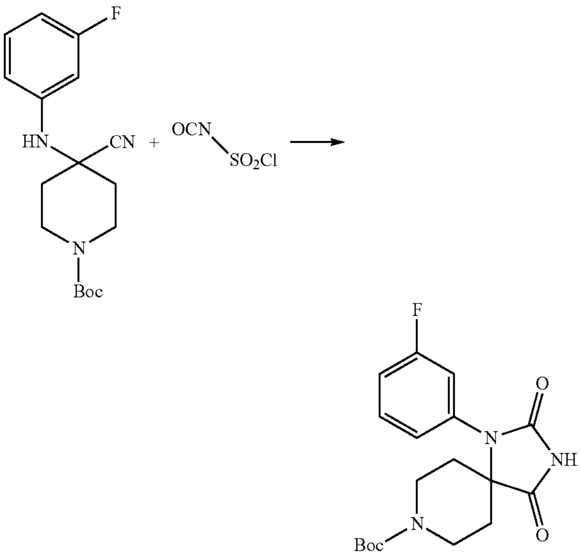

The tert-butyl 4-cyano-4-((3-fluorophenyl)amino)piperidin-1-carboxylate (1.850 g, 5.792 mmol) prepared in step 1 was dissolved in dichloromethane (5 mL), after which sulfurisocyanatidic chloride (1.230 g, 8.689 mmol) was added at 0° C. into the resulting solution and stirred for 30 minutes. 1N-hydrochloric acid aqueous solution (10 mL) was poured into the reaction mixture, after which solvent was concentrated under reduced pressure, and then ethanol (15 mL) was added. The resulting mixture was stirred again at 80° C. for 30 minutes, after which solvent was concentrated under reduced pressure. After that, the resulting mixture was dissolved in THF (20 mL) and adjusted to pH 8 with 10% potassium carbonate solution, after which di-tert-butyl dicarbonate (1.896 g, 8.689 mmol) dissolved in THF (20 mL) was added and stirred for 18 hours. After that, a precipitate solid was filtered to obtain a desired title compound (1.23 g, 59.9%) in a white solid form.

[Step 3] Synthesis of Compound 5

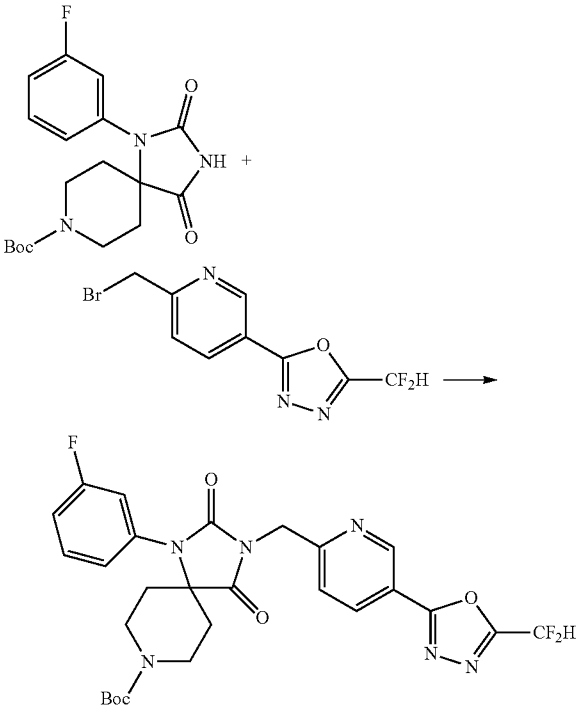

The tert-butyl 1-(3-fluorophenyl)-2,4-dioxo-1,3,8-triazaspiro[4.5]decan-8-carboxylate (0.600 g, 1.651 mmol) prepared in step 2 was dissolved in N,N-dimethylformamide (10 mL) at 0° C., after which sodium hydride (60.00%, 0.099 g, 2.477 mmol) was added into the resulting solution, and stirred at the same temperature for 30 minutes. 2-(6-(bromomethyl)pyridin-3-yl)-5-(difluoromethyl)-1,3,4-oxadiazole (0.718 g, 2.477 mmol) was added into the reaction mixture and further stirred at room temperature for three hours. Water was poured into the reaction mixture and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain a title compound (0.257 g, 27.2%) in a colorless oil form.

$^1H$ NMR (400 MHz, $CDCl_3$) δ 9.22 (t, J=1.1 Hz, 1H), 8.34 (dd, J=8.2, 2.2 Hz, 1H), 7.48~7.39 (m, 2H), 7.20~7.15 (m, 1H), 7.06 (s, 0.25H), 7.01~7.00 (m, 1H), 6.98 (s, 0.5H), 6.99~6.94 (m, 1H), 6.92 (s, 0.25H), 4.95 (s, 2H), 4.10~3.95 (m, 2H), 3.50~3.40 (m, 2H), 1.99~1.95 (m, 2H), 1.80~1.75 (m, 2H), 1.36 (s, 9H); LRMS (ES) m/z 573.4 ($M^+$+1).

Synthesis of Compound 6, 3-((5-(5-(difluoromethyl)-1,3,4-oxadiazol-2-yl)pyridin-2-yl)methyl)-1-(3-fluorophenyl)-8-methyl-1,3,8-triazaspiro[4.5]decan-2,4-dione

[Step 1] Synthesis of 3-((5-(5-(difluoromethyl)-1,3,4-oxadiazol-2-yl)pyridin-2-yl)methyl)-1-(3-fluorophenyl)-1,3,8-triazaspiro[4.5]decan-2,4-dione 2,2,2-trifluoroacetate

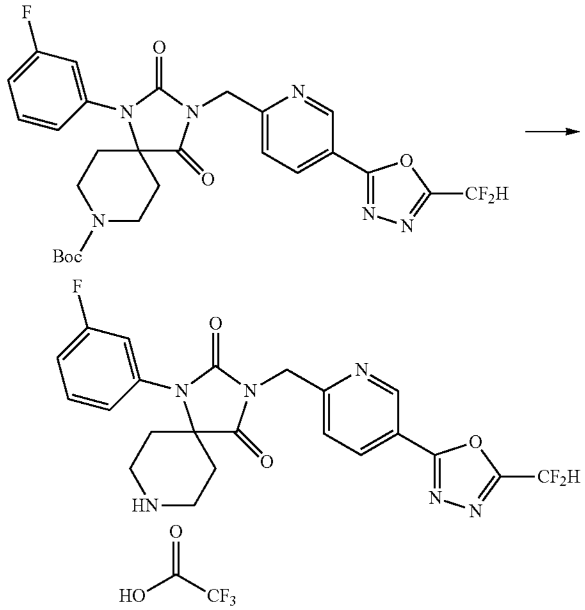

Tert-butyl 3-((5-(5-(difluoromethyl)-1,3,4-oxadiazol-2-yl)pyridin-2-yl)methyl)-1-(3-fluorophenyl)-2,4-dioxo-1,3,8-triazaspiro[4.5]decan-8-carboxylate (0.257 g, 0.449 mmol) and trifluoroacetic acid (0.344 mL, 4.489 mmol) were dissolved in dichloromethane (30 mL) at room temperature, after which the resulting solution was stirred at the same temperature for 12 hours. Solvent was removed from the reaction mixture under reduced pressure, after which an obtained product was used without an additional purification process (0.250 g, 95.0%, yellow oil).

[Step 2] Synthesis of Compound 6

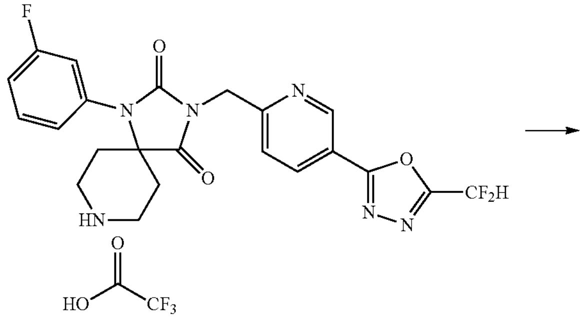

-continued

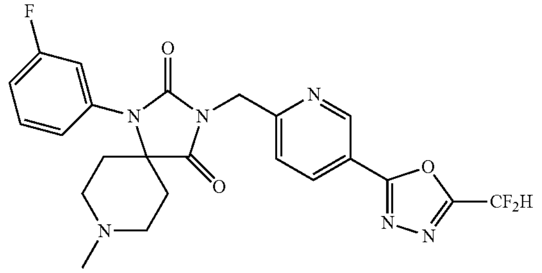

The 3-((5-(5-(difluoromethyl)-1,3,4-oxadiazol-2-yl)pyridin-2-yl)methyl)-1-(3-fluorophenyl)-1,3,8-triazaspiro[4.5]decan-2,4-dione 2,2,2-trifluoroacetate (0.200 g, 0.341 mmol) prepared in step 1, formaldehyde (0.020 g, 0.682 mmol), N,N-diisopropylethylamine (0.059 mL, 0.341 mmol) and sodium triacetoxyborohydride (0.145 g, 0.682 mmol) were dissolved in dichloromethane (10 mL) at room temperature, after which the resulting solution was stirred at the same temperature for two hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; methanol/dichloromethane=0 to 10%) and concentrated to obtain a title compound (0.100 g, 60.3%) in a colorless oil form.

$^1H$ NMR (400 MHz, $CDCl_3$) δ 9.28 (d, J=1.4 Hz, 1H), 8.41 (dd, J=8.2, 2.2 Hz, 1H), 7.51 (d, J=8.2 Hz, 1H), 7.47~7.41 (m, 1H), 7.18~7.14 (m, 1H), 7.08 (s, 0.25H), 7.05~7.03 (m, 1H), 7.00~6.97 (m, 1H), 6.95 (s, 0.5H), 6.82 (s, 0.25H), 5.00 (s, 2H), 3.20~2.90 (m, 4H), 2.48 (s, 3H), 2.23~2.20 (m, 2H), 2.08~2.05 (m, 2H); LRMS (ES) m/z 487.5 ($M^+$+1).

Synthesis of Compound 7, 3-((5-(5-(difluoromethyl)-1,3,4-oxadiazol-2-yl)pyridin-2-yl)methyl)-1-(3-fluorophenyl)-8-(oxetan-3-yl)-1,3,8-triazaspiro[4.5]decan-2,4-dione -continued

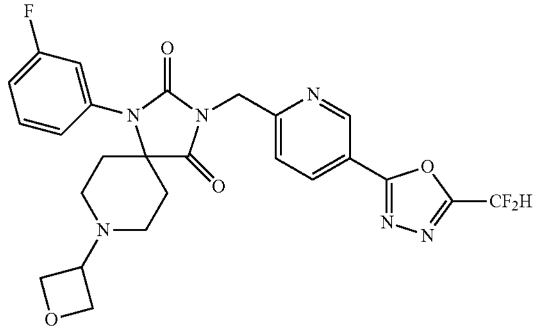

N'-(2,2-difluoroacetyl)-6-((1-(3-fluorophenyl)-8-(oxetan-3-yl)-2,4-dioxo-1,3,8-triazaspiro[4.5]decan-3-yl)methyl)nicotinohydrazide (0.060 g, 0.110 mmol) and 1-methoxy-N-triethylammoniosulfonyl-methanimidate (Burgess reagent, 0.052 g, 0.220 mmol) were dissolved in tetrahydrofuran (5 mL) at 80° C., after which the resulting solution was stirred at the same temperature for 13 hours, and then a reaction was finished by lowering a temperature to room temperature. Water was poured into the reaction mixture and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 100%) and concentrated to obtain a title compound (0.020, 34.5%) in a colorless oil form.

$^1H$ NMR (400 MHz, $CDCl_3$) δ 9.28 (dd, J=2.2, 0.8 Hz, 1H), 8.39 (dd, J=8.2, 2.2 Hz, 1H), 7.51~7.49 (m, 1H), 7.47~7.43 (m, 1H), 7.21~7.16 (m, 1H), 7.08~7.05 (m, 1H), 7.08 (s, 0.25H), 7.01~6.98 (m, 1H), 6.95 (s, 0.5H), 6.82 (s, 0.25H), 4.99 (s, 2H), 4.66 (t, J=6.6 Hz, 2H), 4.55 (t, J=5.0 Hz, 2H), 3.61~3.58 (m, 1H), 2.74~2.66 (m, 4H), 2.11~2.04 (m, 4H).

Synthesis of Compound 8, 3-((5-(5-(difluoromethyl)-1,3,4-oxadiazol-2-yl)pyridin-2-yl)methyl)-1-(3-fluorophenyl)-8-isopropyl-1,3,8-triazaspiro[4.5]decan-2,4-dione

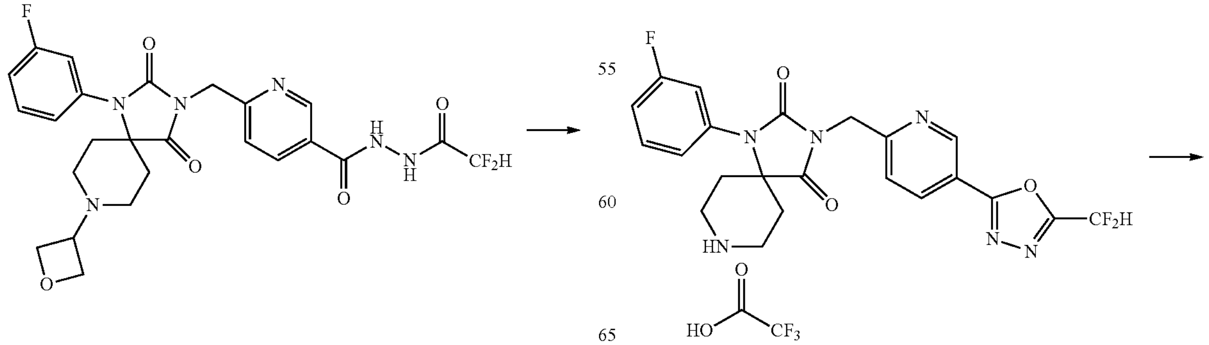

-continued

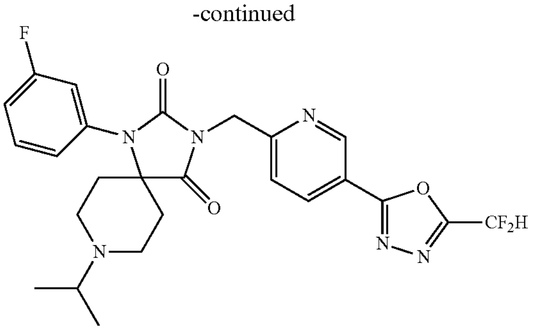

The 3-((5-(5-(difluoromethyl)-1,3,4-oxadiazol-2-yl)pyridin-2-yl)methyl)-1-(3-fluorophenyl)-1,3,8-triazaspiro[4.5]decan-2,4-dione 2,2,2-trifluoroacetate (0.200 g, 0.341 mmol), acetone (0.051 mL, 0.682 mmol), N,N-diisopropylethylamine (0.059 mL, 0.341 mmol) and sodium triacetoxyborohydride (0.145 g, 0.682 mmol) were dissolved in dichloromethane (10 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; methanol/dichloromethane=0 to 10%), and concentrated to obtain a title compound (0.110 g, 62.8%) in a white foamy solid form.

$^1H$ NMR (400 MHz, $CDCl_3$) δ 9.29 (dd, J=2.1, 0.7 Hz, 1H), 8.41 (dd, J=8.2, 2.2 Hz, 1H), 7.53~7.50 (m, 1H), 7.47~7.43 (m, 1H), 7.19~7.16 (m, 1H), 7.08 (s, 0.25H), 7.01~7.00 (m, 1H), 6.99~6.98 (m, 1H), 6.96 (s, 0.5H), 6.83 (s, 0.25H), 5.00 (s, 2H), 3.28~3.25 (m, 1H), 3.10~3.08 (m, 4H), 2.33~2.30 (m, 2H), 2.09~2.06 (m, 2H), 1.18~1.13 (m, 6H); LRMS (ES) m/z 515.5 ($M^+$+1).

Synthesis of Compound 9, 3-((5-(5-(difluoromethyl)-1,3,4-oxadiazol-2-yl)pyrimidin-2-yl)methyl)-1-phenylimidazolidin-2,4-dione

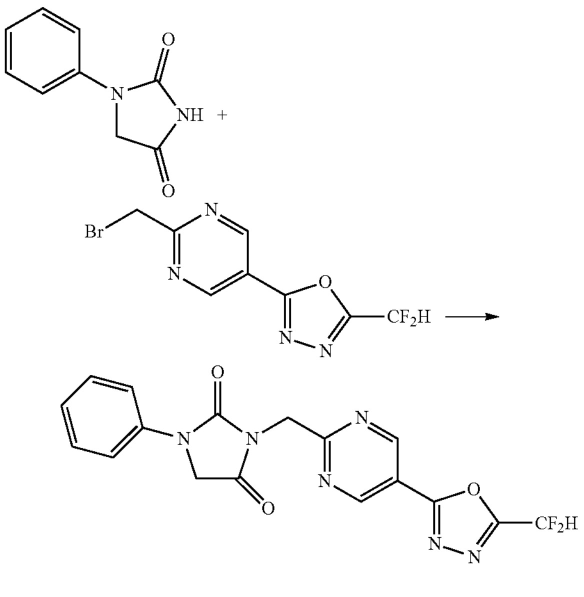

1-phenylimidazolidin-2,4-dione (0.300 g, 1.703 mmol), 2-(2-(bromomethyl)pyrimidin-5-yl)-5-(difluoromethyl)-1,3,4-oxadiazole (0.496 g, 1.703 mmol) and potassium carbonate (0.353 g, 2.554 mmol) were dissolved in N,N-dimethylformamide (5 mL) at 80° C., after which the resulting solution was stirred at the same temperature for 12 hours, and then a reaction was finished by lowering a temperature to room temperature. Water was poured into the reaction mixture and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain a title compound (0.110 g, 16.7%) in a yellow solid form.

$^1H$ NMR (400 MHz, $CDCl_3$) δ 9.37 (s, 2H), 7.65~7.62 (m, 2H), 7.46~7.42 (m, 2H), 7.23~7.19 (m, 1H), 7.10 (s, 0.25H), 6.97 (s, 0.5H), 6.84 (s, 0.25H), 5.18 (s, 2H), 4.52 (s, 2H); LRMS (ES) m/z 387.3 ($M^+$+1).

Synthesis of Compound 10, 3-((5-(5-(difluoromethyl)-1,3,4-oxadiazol-2-yl)pyridin-2-yl)methyl)-1-(3-fluorophenyl)-5,5-dimethylimidazolidin-2,4-dione

[Step 1] Synthesis of 2-((3-fluorophenyl)amino)-2-methylpropanenitrile

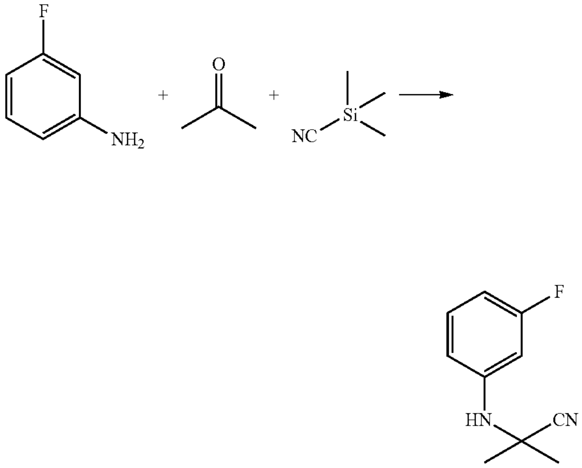

The 3-fluoroaniline (1.000 g, 8.999 mmol), trimethylsilylacarbonitrile (0.893 g, 8.999 mmol) and propan-2-one (0.523 g, 8.999 mmol) were dissolved in acetone (20 mL) at room temperature, after which the resulting solution was stirred at the same temperature for 12 hours. Saturated ammonium chloride aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 40 g cartridge; ethyl acetate/hexane=0 to 20%) and concentrated to obtain a title compound (1.240 g, 77.3%) in a white solid form.

[Step 2] Synthesis of 1-(3-fluorophenyl)-5,5-dimethylimidazolidin-2,4-dione

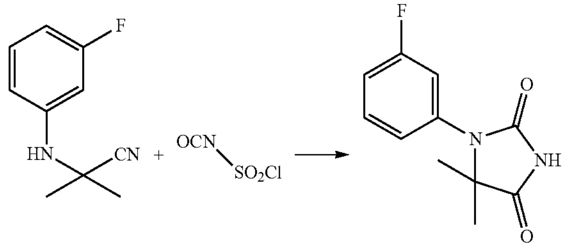

The 2-(3-fluorophenyl)-2-methylpropanenitrile (1.240 g, 7.598 mmol) prepared in step 1 and sulfurisocyanatidic chloride (1.613 g, 11.397 mmol) were dissolved in dichloromethane (10 mL) at room temperature, after which the resulting solution was stirred at the same temperature for one hour. 1N-hydrochloric acid aqueous solution (10 mL) was poured into the reaction mixture, after which solvent was concentrated under reduced pressure, and then ethanol (15 mL) was added. The resulting mixture was stirred again at 80° C. for 30 minutes, after which solvent was concentrated under reduced pressure. The resulting concentrate was purified via column chromatography ($SiO_2$, 12 g cartridge; ethyl acetate/hexane=0 to 30%) and concentrated to obtain a title compound (0.880 g, 52.1%) in a white solid form.

[Step 3] Synthesis of Compound 10

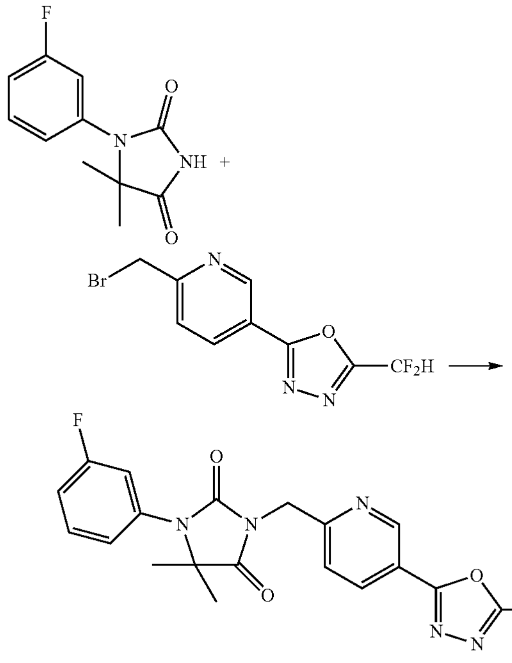

The 1-(3-fluorophenyl)-5,5-dimethylimidazolidin-2,4-dione (0.100 g, 0.450 mmol) prepared in step 2, 2-(6-(bromomethyl)pyridin-3-yl)-5-(difluoromethyl)-1,3,4-oxadiazole (0.144 g, 0.495 mmol) and potassium carbonate (0.124 g, 0.900 mmol) were dissolved in N,N-dimethylformamide (10 mL), after which the resulting solution was stirred at 50° C. for 18 hours, and then further stirred at room temperature for 18 hours. Water was poured into the reaction mixture and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 80%) and concentrated to obtain a title compound (0.130 g, 67.0%) in a white solid form.

$^1$H NMR (400 MHz, $CDCl_3$) δ 9.26 (t, J=1.1 Hz, 1H), 8.37 (dd, J=8.2, 2.2 Hz, 1H), 7.49 (d, J=8.2 Hz, 1H), 7.43~7.40 (m, 1H), 7.14~7.06 (m, 3H), 7.08 (s, 0.25H), 6.95 (s, 0.5H), 6.82 (s, 0.25H), 5.00 (s, 2H), 1.55 (s, 6H); LRMS (ES) m/z 432.3 ($M^+$+1).

Synthesis of Compound 11, 1-(3-bromophenyl)-3-((5-(5-(difluoromethyl)-1,3,4-oxadiazol-2-yl)pyridin-2-yl)methyl)-5,5-dimethylimidazolidin-2,4-dione

[Step 1] Synthesis of 2-((3-bromophenyl)amino)-2-methylpropanenitrile

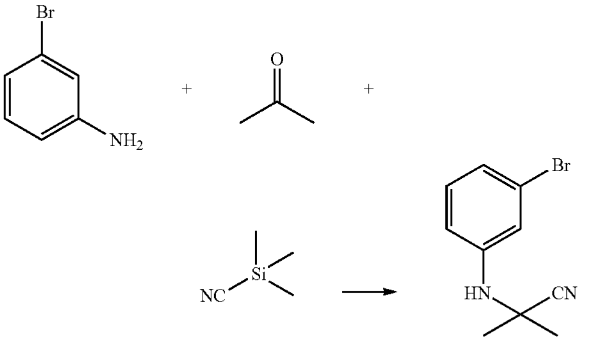

The 3-bromoaniline (2.000 g, 11.626 mmol), trimethylsilacarbonitrile (1.150 g, 11.626 mmol) and propan-2-one (0.675 g, 11.626 mmol) were dissolved in acetone (20 mL) at room temperature, after which the resulting solution was stirred at the same temperature for 12 hours. Saturated ammonium chloride aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 40 g cartridge; ethyl acetate/hexane=0 to 20%), and concentrated to obtain a title compound (2.200 g, 79.1%) in a brown oil form.

[Step 2] Synthesis of 1-(3-bromophenyl)-5,5-dimethylimidazolidin-2,4-dione

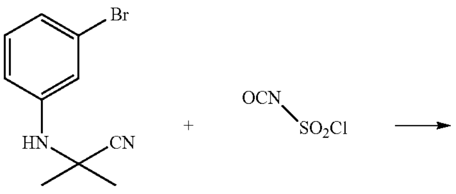

-continued

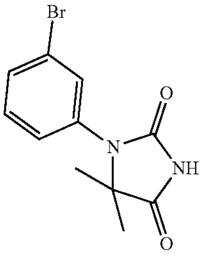

The 2-(3-bromophenyl)-2-methylpropanenitrile (2.200 g, 9.817 mmol) prepared in step 1 and sulfurisocyanatidic chloride (2.084 g, 14.726 mmol) were dissolved in dichloromethane (10 mL) at room temperature, after which the resulting solution was stirred at the same temperature for one hour. 1N-hydrochloric acid aqueous solution (10 mL) was poured into the reaction mixture, after which solvent was concentrated under reduced pressure, and then ethanol (15 mL) was added. The resulting mixture was stirred again at 80° C. for 30 minutes, after which solvent was concentrated under reduced pressure. The resulting concentrate was purified via column chromatography ($SiO_2$, 12 g cartridge; ethyl acetate/hexane=0 to 30%) and concentrated to obtain a title compound (1.500 g, 54.0%) in a white solid form.

[Step 3] Synthesis of Compound 11

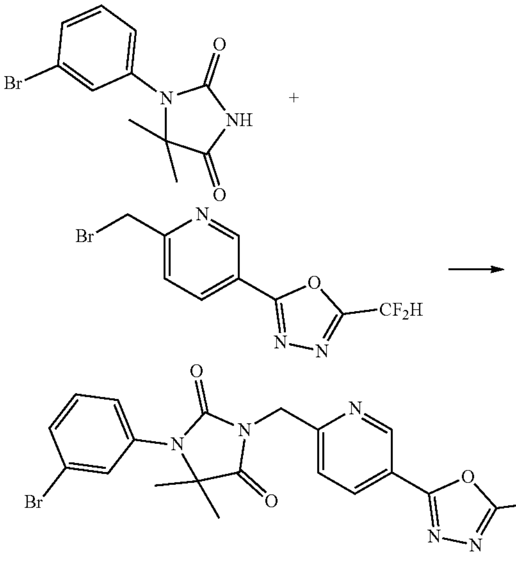

The 1-(3-bromophenyl)-5,5-dimethylimidazolidin-2,4-dione (0.892 g, 3.150 mmol) prepared in step 2, 2-(6-(bromomethyl)pyridin-3-yl)-5-(difluoromethyl)-1,3,4-oxadiazole (1.005 g, 3.466 mmol) and potassium carbonate (0.871 g, 6.301 mmol) were dissolved in N,N-dimethylformamide (10 mL), after which the resulting solution was stirred at 50° C. for 18 hours, and then further stirred at room temperature for 18 hours. Water was poured into the reaction mixture and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 80%), and concentrated to obtain a title compound (1.100 g, 70.9%) in a yellow oil form.

$^1H$ NMR (400 MHz, $CDCl_3$) δ 9.30 (t, J=1.1 Hz, 1H), 8.41 (dd, J=8.2, 2.2 Hz, 1H), 7.57~7.55 (m, 1H), 7.51~7.49 (m, 1H), 7.36 (t, J=8.0 Hz, 1H), 7.30~7.27 (m, 2H), 7.09 (s, 0.25H), 6.95 (s, 0.5H), 6.83 (s, 0.25H), 5.03 (s, 2H), 1.59 (s, 6H); LRMS (ES) m/z 494.2 ($M^+$+1).

Synthesis of Compound 12, 3-((5-(5-(difluoromethyl)-1,3,4-oxadiazol-2-yl)pyridin-2-yl)methyl)-1-(4-fluorophenyl)-5,5-dimethylimidazolidin-2,4-dione

[Step 1] Synthesis of 2-((4-fluorophenyl)amino)-2-methylpropanenitrile

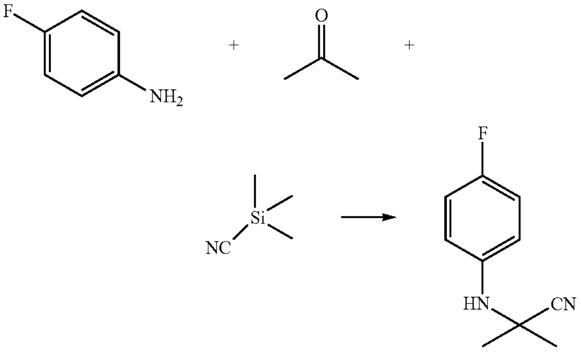

The 4-fluoroaniline (1.000 g, 8.999 mmol), trimethylsilacarbonitrile (0.893 g, 8.999 mmol) and propan-2-one (0.523 g, 8.999 mmol) were dissolved in acetone (20 mL) at room temperature, after which the resulting solution was stirred at the same temperature for 12 hours. Saturated ammonium chloride aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 40 g cartridge; ethyl acetate/hexane=0 to 20%) and concentrated to obtain a title compound (0.535 g, 33.4%) in a white solid form.

[Step 2] Synthesis of 1-(4-fluorophenyl)-5,5-dimethylimidazolidin-2,4-dione

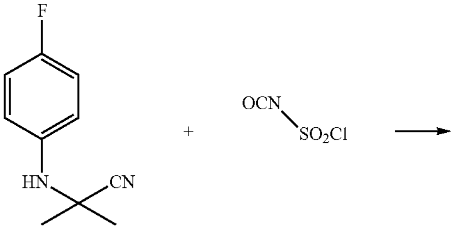

-continued

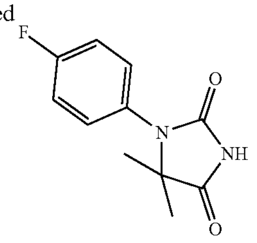

The 2-(4-fluorophenyl)-2-methylpropanenitrile (0.530 g, 3.248 mmol) prepared in step 1 and sulfurisocyanatidic chloride (0.689 g, 4.871 mmol) were dissolved in dichloromethane (10 mL) at room temperature, after which the resulting solution was stirred at the same temperature for one hour. 1N-hydrochloric acid aqueous solution (10 mL) was poured into the reaction mixture, after which solvent was concentrated under reduced pressure, and then ethanol (15 mL) was added. The resulting mixture was stirred again at 80° C. for 30 minutes, after which solvent was concentrated under reduced pressure. The resulting concentrate was purified via column chromatography ($SiO_2$, 12 g cartridge; ethyl acetate/hexane=0 to 30%) and concentrated to obtain a title compound (0.330 g, 45.7%) in a white solid form.

[Step 3] Synthesis of Compound 12

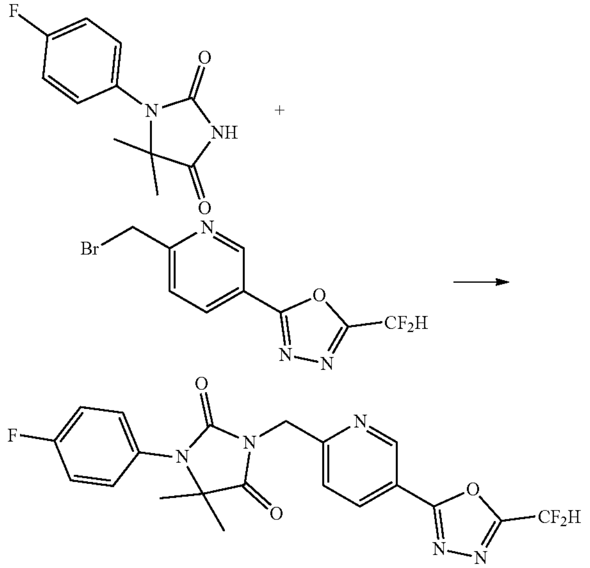

The 1-(4-fluorophenyl)-5,5-dimethylimidazolidin-2,4-dione (0.100 g, 0.450 mmol) prepared in step 2, 2-(6-(bromomethyl)pyridin-3-yl)-5-(difluoromethyl)-1,3,4-oxadiazole (0.144 g, 0.495 mmol) and potassium carbonate (0.124 g, 0.900 mmol) were dissolved in N,N-dimethylformamide (10 mL), after which the resulting solution was stirred at 50° C. for 18 hours, and then further stirred at room temperature for 18 hours. Water was poured into the reaction mixture and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 80%) and concentrated to obtain a title compound (0.110 g, 56.7%) in a white solid form.

$^1$H NMR (400 MHz, $CDCl_3$) δ 9.27 (t, J=1.1 Hz, 1H), 8.38 (dd, J=8.2, 2.2 Hz, 1H), 7.49 (d, J=8.2 Hz, 1H), 7.30~7.26 (m, 2H), 7.17~7.13 (m, 2H), 7.08 (s, 0.25H), 6.95 (s, 0.5H), 6.82 (s, 0.25H), 5.01 (s, 2H), 1.52 (s, 6H); LRMS (ES) m/z 432.3 ($M^+$+1).

Synthesis of Compound 13, 3-((5-(5-(difluoromethyl)-1,3,4-oxadiazol-2-yl)pyridin-2-yl)methyl)-1-(2,6-difluorophenyl)-5,5-dimethylimidazolidin-2,4-dione

[Step 1] Synthesis of 2-((2,6-difluorophenyl) amino)-2-methylpropanenitrile

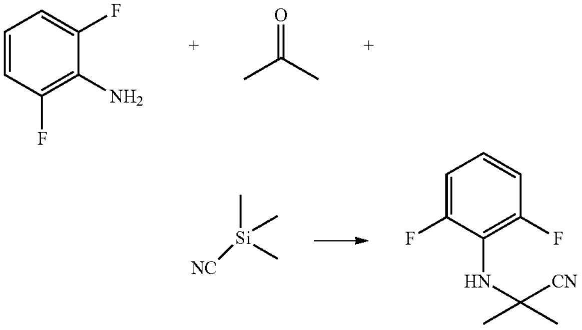

The 2,6-difluoroaniline (0.781 mL, 7.745 mmol), trimethylsilacarbonitrile (0.973 mL, 7.745 mmol) and propan-2-one (0.569 mL, 7.745 mmol) were dissolved in acetic acid (10 mL) at room temperature, after which the resulting solution was stirred at the same temperature for 18 hours. Solvent was removed from the reaction mixture under reduced pressure, after which hexane (20 mL) and ethyl acetate (10 mL) were added into the resulting concentrate and stirred to filter out a precipitated solid, washed with hexane, and dried to obtain a title compound (0.330 g, 21.7%) in a white solid form.

[Step 2] Synthesis of 1-(2,6-difluorophenyl)-5,5-dimethylimidazolidin-2,4-dione

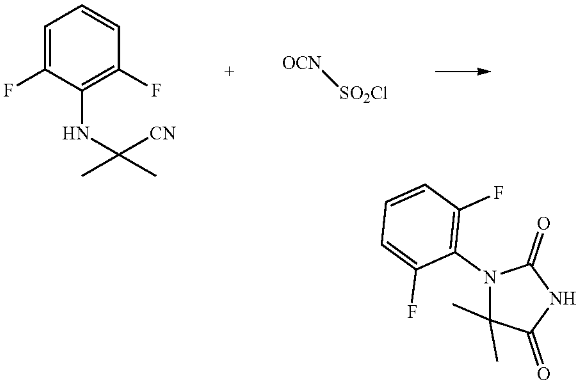

The 2-((2,6-difluorophenyl)amino)-2-methylpropanenitrile (0.330 g, 1.682 mmol) prepared in step 1 and sulfurisocyanatidic chloride (0.357 g, 2.523 mmol) were dissolved in dichloromethane (50 mL), after which the resulting solution was stirred at 0° C. for 30 minutes and further stirred at room temperature for 18 hours. 1N-hydrochloric acid aqueous solution (10 mL) was poured into the reaction mixture, after which solvent was concentrated under reduced pressure, and then ethanol (30 mL) was added. The resulting mixture was stirred again at 80° C. for 30 minutes, after which solvent was concentrated under reduced pressure. The resulting concentrate was purified via column chromatography ($SiO_2$, 12 g cartridge; ethyl acetate/hexane=0 to 50%) and concentrated to obtain a title compound (0.100 g, 24.8%) in a white solid form.

[Step 3] Synthesis of Compound 13

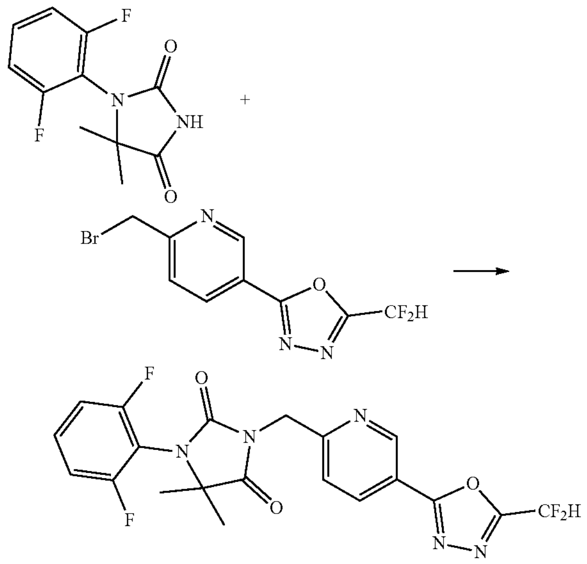

The 1-(2,6-difluorophenyl)-5,5-dimethylimidazolidin-2,4-dione (0.100 g, 0.416 mmol) prepared in step 2, 2-(6-(bromomethyl)pyridin-3-yl)-5-(difluoromethyl)-1,3,4-oxadiazole (0.121 g, 0.416 mmol) and potassium carbonate (0.115 g, 0.833 mmol) were dissolved in N,N-dimethylformamide (5 mL) at 80° C., after which the resulting solution was stirred at the same temperature for 18 hours, and then a reaction was finished by lowering a temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain a title compound (0.150 g, 80.2%) in a white solid form.

$^1H$ NMR (400 MHz, $CDCl_3$) δ 9.30 (dd, J=2.2, 0.8 Hz, 1H), 8.40 (dd, J=8.2, 2.2 Hz, 1H), 7.48~7.39 (m, 2H), 7.09~7.05 (m, 2H), 7.08 (s, 0.25H), 6.95 (s, 0.5H), 6.82 (s, 0.25H), 5.04 (s, 2H), 1.54 (s, 6H); LRMS (ES) m/z 450.2 ($M^+$+1).

Synthesis of Compound 14, 3-((5-(5-(difluoromethyl)-1,3,4-oxadiazol-2-yl)pyridin-2-yl)methyl)-1-(2,4-difluorophenyl)-5,5-dimethylimidazolidin-2,4-dione

[Step 1] Synthesis of 2-((2,4-difluorophenyl) amino)-2-methylpropanenitrile

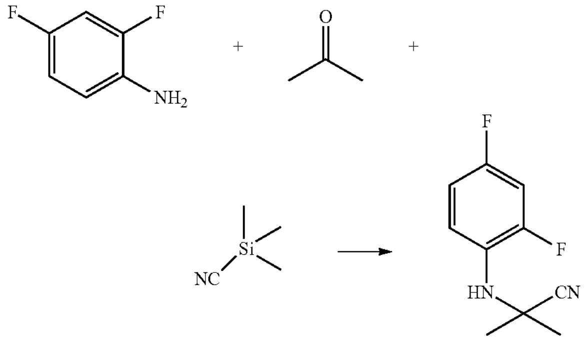

The 2,4-difluoroaniline (1.000 g, 7.745 mmol), trimethylsilacarbonitrile (0.768 g, 7.745 mmol) and propan-2-one (0.450 g, 7.745 mmol) were dissolved in acetic acid (10 mL) at room temperature, after which the resulting solution was stirred at the same temperature for 18 hours. Solvent was removed from the reaction mixture under reduced pressure, after which hexane (20 mL) and ethyl acetate (10 mL) were added into the resulting concentrate and stirred to filter out a precipitated solid, washed with hexane, and dried to obtain a title compound (1.000 g, 65.8%) in a white solid form.

[Step 2] Synthesis of 1-(2,4-difluorophenyl)-5,5-dimethylimidazolidin-2,4-dione

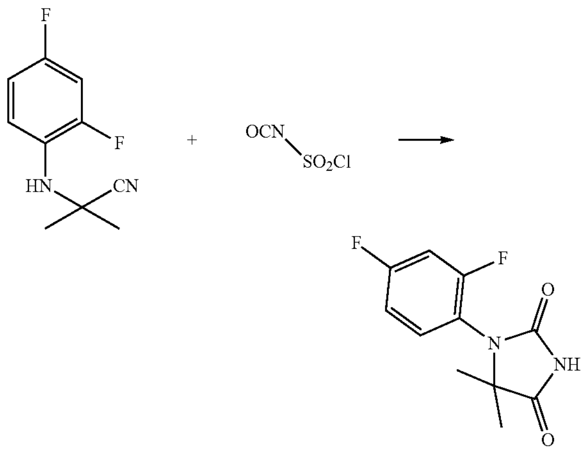

The 2-((2,4-difluorophenyl)amino)-2-methylpropanenitrile (1.000 g, 5.097 mmol) prepared in step 1 and sulfurisocyanatidic chloride (1.082 g, 7.645 mmol) were dissolved in dichloromethane (50 mL), after which the resulting solution was stirred at 0° C. for 30 minutes and further stirred at room temperature for 18 hours. 1N-hydrochloric acid aqueous solution (10 mL) was poured into the reaction mixture, after which solvent was concentrated under reduced pressure, and then ethanol (30 mL) was added. The resulting mixture was stirred again at 80° C. for 30 minutes, after which solvent was concentrated under reduced pressure. The resulting concentrate was purified via column chromatography ($SiO_2$, 12 g cartridge; ethyl acetate/hexane=0 to 50%) and concentrated to obtain a title compound (0.700 g, 57.2%) in a white solid form.

[Step 3] Synthesis of Compound 14

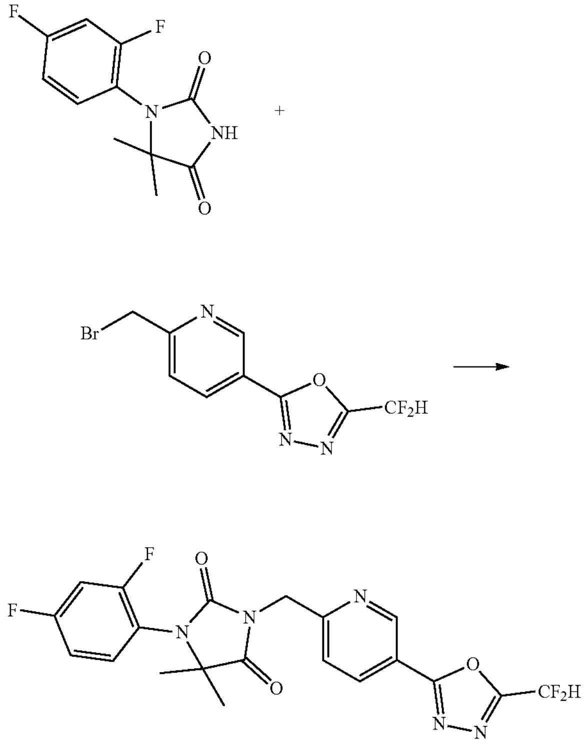

The 1-(2,4-difluorophenyl)-5,5-dimethylimidazolidin-2,4-dione (0.100 g, 0.416 mmol) prepared in step 2, 2-(6-(bromomethyl)pyridin-3-yl)-5-(difluoromethyl)-1,3,4-oxadiazole (0.121 g, 0.416 mmol) and potassium carbonate (0.115 g, 0.833 mmol) were dissolved in N,N-dimethylformamide (5 mL) at 80° C., after which the resulting solution was stirred at the same temperature for 18 hours, and then a reaction was finished by lowering a temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain a title compound (0.130 g, 69.5%) in a white solid form.

$^1H$ NMR (400 MHz, $CDCl_3$) δ 9.30 (d, J=2.2 Hz, 1H), 8.40 (dd, J=8.2, 2.2 Hz, 1H), 7.49 (d, J=8.2 Hz, 1H), 7.31~7.28 (m, 1H), 7.08 (s, 0.25H), 7.04~6.99 (m, 2H), 6.95 (s, 0.5H), 6.82 (s, 0.25H), 5.03 (s, 2H), 1.52 (s, 6H); LRMS (ES) m/z 450.2 ($M^+$±1).

Synthesis of Compound 15, 3-((5-(5-(difluoromethyl)-1,3,4-oxadiazol-2-yl)pyridin-2-yl)methyl)-1-(2,3-difluorophenyl)-5,5-dimethylimidazolidin-2,4-dione

[Step 1] Synthesis of 2-((2,3-difluorophenyl)amino)-2-methylpropanenitrile

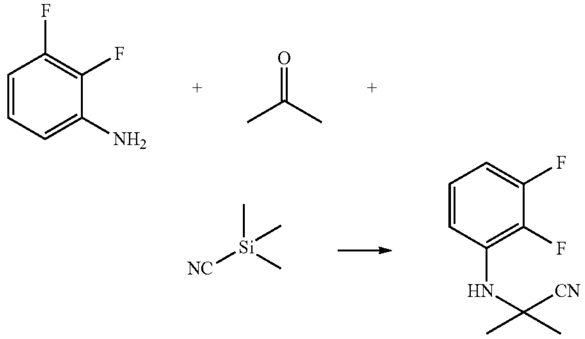

The 2,3-difluoroaniline (1.000 g, 7.745 mmol), trimethylsilacarbonitrile (0.768 g, 7.745 mmol) and propan-2-one (0.450 g, 7.745 mmol) were dissolved in acetic acid (10 mL) at room temperature, after which the resulting solution was stirred at the same temperature for 18 hours. Solvent was removed from the reaction mixture under reduced pressure, after which hexane (20 mL) and ethyl acetate (10 mL) were added into the resulting concentrate and stirred to filter out a precipitated solid, washed with hexane, and dried to obtain a title compound (1.100 g, 72.4%) in a white solid form.

[Step 2] Synthesis of 1-(2,3-difluorophenyl)-5,5-dimethylimidazolidin-2,4-dione

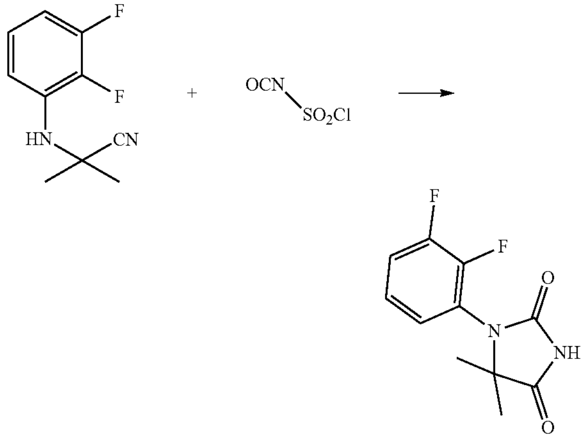

The 2-((2,3-difluorophenyl)amino)-2-methylpropanenitrile (1.100 g, 5.607 mmol) prepared in step 1 and sulfurisocyanatidic chloride (1.190 g, 8.410 mmol) were dissolved in dichloromethane (50 mL), after which the resulting solution was stirred at 0° C. for 30 minutes and further stirred at room temperature for 18 hours. 1N-hydrochloric acid aqueous solution (10 mL) was poured into the reaction mixture, after which solvent was concentrated under reduced pressure, and then ethanol (30 mL) was added. The resulting mixture was stirred again at 80° C. for 30 minutes, after which solvent was concentrated under reduced pressure. The resulting concentrate was purified via column chromatography ($SiO_2$, 12 g cartridge; ethyl acetate/hexane=0 to 50%) and concentrated to obtain a title compound (0.800 g, 59.4%) in a white solid form.

[Step 3] Synthesis of Compound 15

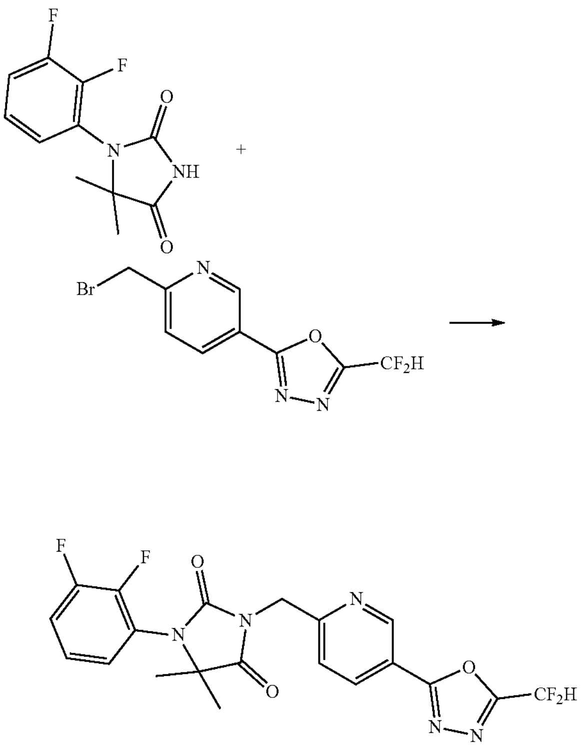

The 1-(2,3-difluorophenyl)-5,5-dimethylimidazolidin-2,4-dione (0.100 g, 0.416 mmol) prepared in step 2, 2-(6-(bromomethyl)pyridin-3-yl)-5-(difluoromethyl)-1,3,4-oxadiazole (0.121 g, 0.416 mmol) and potassium carbonate (0.115 g, 0.833 mmol) were dissolved in N,N-dimethylformamide (5 mL) at 80° C., after which the resulting solution was stirred at the same temperature for 18 hours, and then a reaction was finished by lowering a temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain a title compound (0.150 g, 80.2%) in a white solid form.

$^1H$ NMR (400 MHz, $CDCl_3$) δ 9.30 (dd, J=3.0, 1.7 Hz, 1H), 8.41 (dd, J=8.2, 2.2 Hz, 1H), 7.50 (dd, J=8.2, 0.7 Hz, 1H), 7.31~7.28 (m, 1H), 7.21~7.19 (m, 1H), 7.12~7.08 (m, 1H), 7.08 (s, 0.25H), 6.95 (s, 0.5H), 6.82 (s, 0.25H), 5.04 (s, 2H), 1.54 (s, 6H); LRMS (ES) m/z 450.2 ($M^+$+1).

Synthesis of Compound 16, 3-((5-(5-(difluoromethyl)-1,3,4-oxadiazol-2-yl)pyridin-2-yl)methyl)-1-(3,4-difluorophenyl)-5,5-dimethylimidazolidin-2,4-dione

[Step 1] Synthesis of 2-((3,4-difluorophenyl)amino)-2-methylpropanenitrile

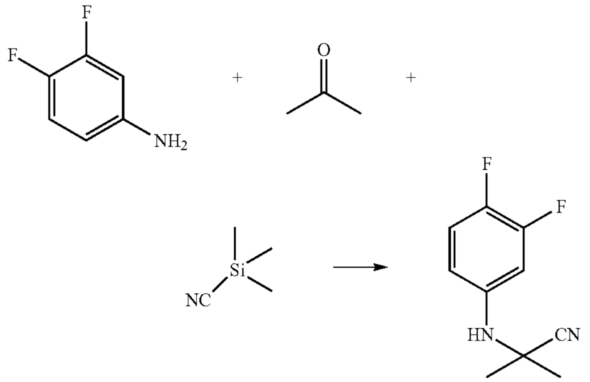

The 3,4-difluoroaniline (1.000 g, 7.745 mmol), trimethylsilacarbonitrile (0.768 g, 7.745 mmol) and propan-2-one (0.450 g, 7.745 mmol) were dissolved in acetic acid (10 mL) at room temperature, after which the resulting solution was stirred at the same temperature for 18 hours. Solvent was removed from the reaction mixture under reduced pressure, after which hexane (20 mL) and ethyl acetate (10 mL) were added into the resulting concentrate and stirred to filter out a precipitated solid, washed with hexane, and dried to obtain a title compound (0.700 g, 46.1%) in a white solid form.

[Step 2] Synthesis of 1-(3,4-difluorophenyl)-5,5-dimethylimidazolidin-2,4-dione

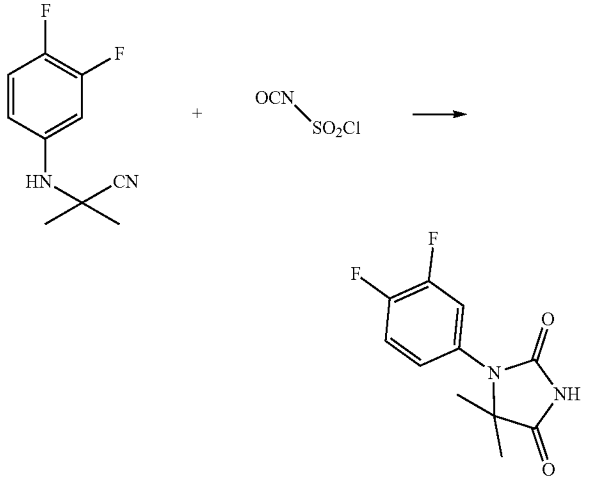

The 2-((3,4-difluorophenyl)amino)-2-methylpropanenitrile (0.700 g, 3.568 mmol) prepared in step 1 and sulfurisocyanatidic chloride (0.757 g, 5.352 mmol) were dissolved in dichloromethane (50 mL), after which the resulting solution was stirred at 0° C. for 30 minutes and further stirred at room temperature for 18 hours. 1N-hydrochloric acid aqueous solution (10 mL) was poured into the reaction mixture, after which solvent was concentrated under reduced pressure, and then ethanol (30 mL) was added. The resulting mixture was stirred again at 80° C. for 30 minutes, after which solvent was concentrated under reduced pressure. The resulting concentrate was purified via column chromatography ($SiO_2$, 12 g cartridge; ethyl acetate/hexane=0 to 50%) and concentrated to obtain a title compound (0.450 g, 52.5%) in a white solid form.

[Step 3] Synthesis of Compound 16

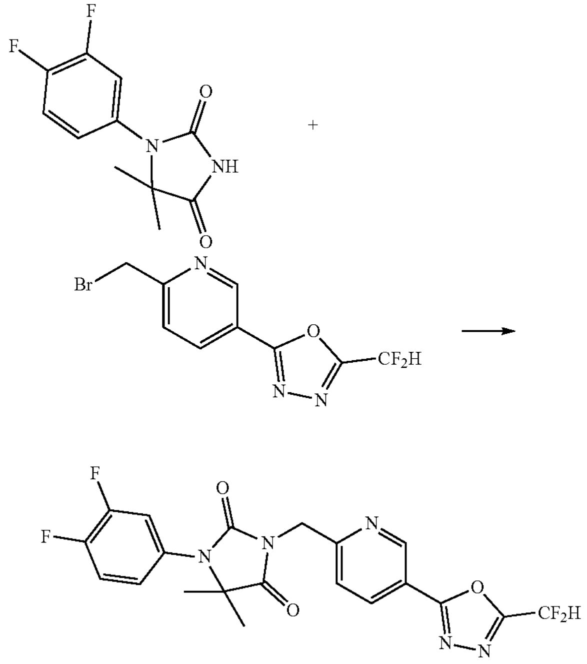

The 1-(3,4-difluorophenyl)-5,5-dimethylimidazolidin-2,4-dione (0.100 g, 0.416 mmol) prepared in step 2, 2-(6-(bromomethyl)pyridin-3-yl)-5-(difluoromethyl)-1,3,4-oxadiazole (0.121 g, 0.416 mmol) and potassium carbonate (0.115 g, 0.833 mmol) were dissolved in N,N-dimethylformamide (5 mL) at 80° C., after which the resulting solution was stirred at the same temperature for 18 hours, and then a reaction was finished by lowering a temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain a title compound (0.130 g, 69.5%) in a white solid form.

$^1$H NMR (400 MHz, $CDCl_3$) δ 9.28 (t, J=1.1 Hz, 1H), 8.40 (dd, J=8.2, 2.2 Hz, 1H), 7.51~7.49 (m, 1H), 7.28~7.19 (m, 2H), 7.09~7.08 (m, 1H), 7.08 (s, 0.25H), 6.95 (s, 0.5H), 6.82 (s, 0.25H), 5.01 (s, 2H), 1.55 (s, 6H); LRMS (ES) m/z 450.4 ($M^+$+1).

Synthesis of Compound 17, 3-((5-(5-(difluoromethyl)-1,3,4-oxadiazol-2-yl)pyridin-2-yl)methyl)-1-(3,5-difluorophenyl)-5,5-dimethylimidazolidin-2,4-dione

[Step 1] Synthesis of 2-((3,5-difluorophenyl)amino)-2-methylpropanenitrile

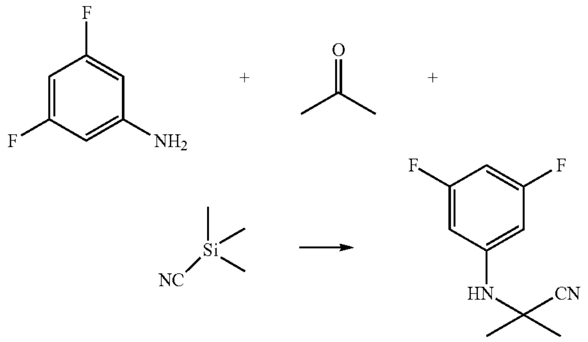

The 3,5-difluoroaniline (1.000 g, 7.745 mmol), trimethylsilacarbonitrile (0.768 g, 7.745 mmol) and propan-2-one (0.450 g, 7.745 mmol) were dissolved in acetic acid (10 mL) at room temperature, after which the resulting solution was stirred at the same temperature for 18 hours. Solvent was removed from the reaction mixture under reduced pressure, after which hexane (20 mL) and ethyl acetate (10 mL) were added into the resulting concentrate and stirred to filter out a precipitated solid, washed with hexane, and dried to obtain a title compound (1.100 g, 72.4%) in a white solid form.

[Step 2] Synthesis of 1-(3,5-difluorophenyl)-5,5-dimethylimidazolidin-2,4-dione

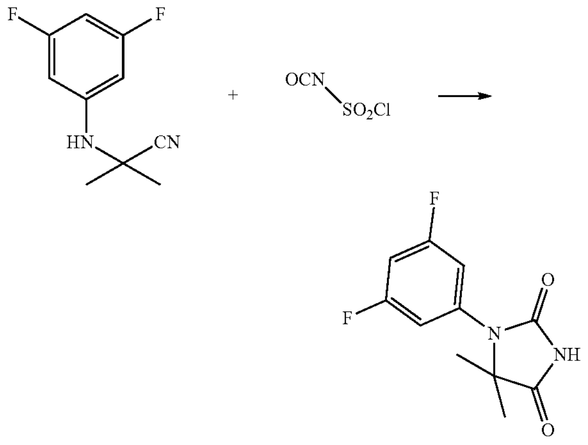

The 2-((3,5-difluorophenyl)amino)-2-methylpropanenitrile (1.100 g, 5.607 mmol) prepared in step 1 and sulfurisocyanatidic chloride (1.190 g, 8.410 mmol) were dissolved in dichloromethane (50 mL), after which the resulting solution was stirred at 0° C. for 30 minutes and further stirred at room temperature for 18 hours. 1N-hydrochloric acid aqueous solution (10 mL) was poured into the reaction mixture, after which solvent was concentrated under reduced pressure, and then ethanol (30 mL) was added. The resulting mixture was stirred again at 80° C. for 30 minutes, after which solvent was concentrated under reduced pressure. The resulting concentrate was purified via column chromatography ($SiO_2$, 12 g cartridge; ethyl acetate/hexane=0 to 50%) and concentrated to obtain a title compound (0.800 g, 59.4%) in a white solid form.

[Step 3] Synthesis of Compound 17

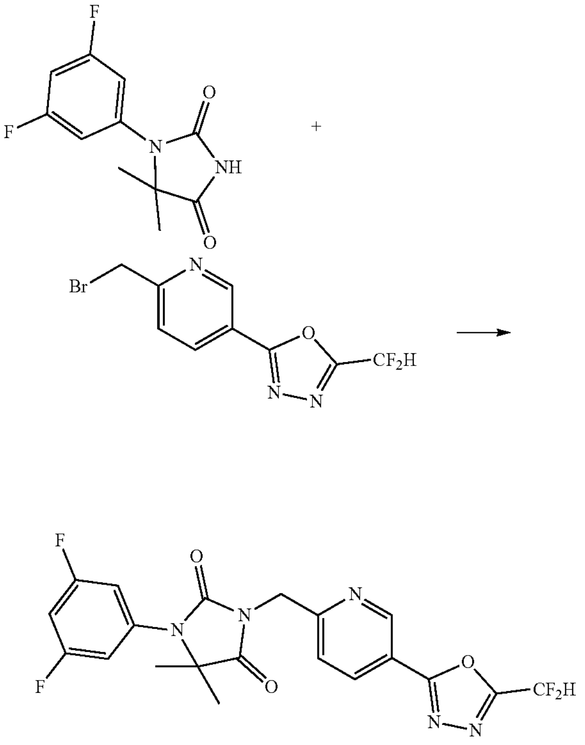

The 1-(3,5-difluorophenyl)-5,5-dimethylimidazolidin-2,4-dione (0.100 g, 0.416 mmol) prepared in step 2, 2-(6-(bromomethyl)pyridin-3-yl)-5-(difluoromethyl)-1,3,4-oxadiazole (0.121 g, 0.416 mmol) and potassium carbonate (0.115 g, 0.833 mmol) were dissolved in N,N-dimethylformamide (5 mL) at 80° C., after which the resulting solution was stirred at the same temperature for 18 hours, and then a reaction was finished by lowering a temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain a title compound (0.110 g, 58.8%) in a white solid form.

$^1H$ NMR (400 MHz, $CDCl_3$) δ 9.28 (t, J=1.1 Hz, 1H), 8.41 (dd, J=8.2, 2.2 Hz, 1H), 7.51 (d, J=8.2 Hz, 1H), 7.09~7.08 (m, 1H), 7.08 (s, 0.25H), 6.97~6.94 (m, 2H), 6.95 (s, 0.5H), 6.82 (s, 0.25H), 5.02 (s, 2H), 1.61 (s, 6H); LRMS (ES) m/z 450.2 ($M^+$+1).

Synthesis of Compound 18, 3-((5-(5-(difluoromethyl)-1,3,4-oxadiazol-2-yl)pyridin-2-yl)methyl)-5,5-dimethyl-1-phenylimidazolidin-2,4-dione

[Step 1] Synthesis of 2-methyl-2-(phenylamino)propanenitrile

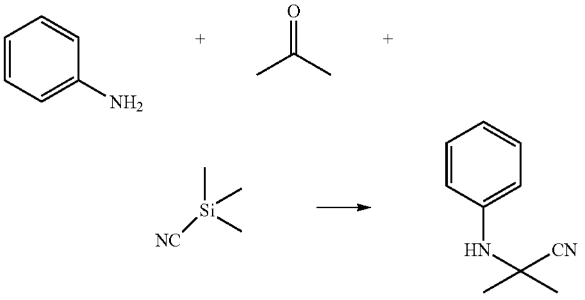

Aniline (0.980 mL, 10.738 mmol), trimethylsilacarbonitrile (1.065 g, 10.738 mmol) and propan-2-one (0.624 g, 10.738 mmol) were dissolved in acetic acid (10 mL) at room temperature, after which the resulting solution was stirred at the same temperature for 18 hours. Solvent was removed from the reaction mixture under reduced pressure, after which hexane (20 mL) and ethyl acetate (10 mL) were added into the resulting concentrate and stirred to filter out a precipitated solid, washed with hexane, and dried to obtain a title compound (1.100 g, 63.9%) in a white solid form.

[Step 2] Synthesis of 5,5-dimethyl-1-phenylimidazolidin-2,4-dione

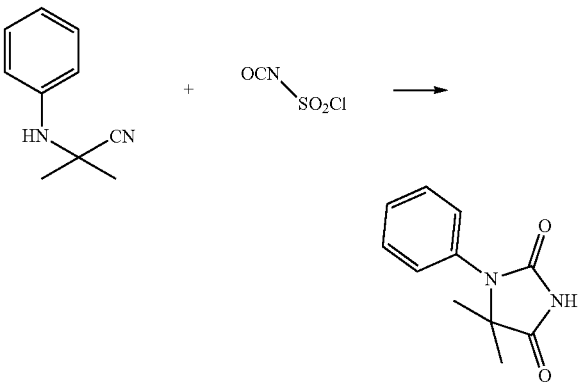

The 2-methyl-2-(phenylamino)propanenitrile (1.100 g, 6.866 mmol) prepared in step 1 and sulfurisocyanatidic chloride (1.458 g, 10.298 mmol) were dissolved in dichloromethane (50 mL), after which the resulting solution was stirred at 0° C. for 30 minutes and further stirred at room temperature for 18 hours. 1N-hydrochloric acid aqueous solution (10 mL) was poured into the reaction mixture, after which solvent was concentrated under reduced pressure, and then ethanol (30 mL) was added. The resulting mixture was stirred again at 80° C. for 30 minutes, after which solvent was concentrated under reduced pressure. The resulting concentrate was purified via column chromatography ($SiO_2$, 12 g cartridge; ethyl acetate/hexane=0 to 50%) and concentrated to obtain a title compound (0.600 g, 42.8%) in a white solid form.

[Step 3] Synthesis of Compound 18

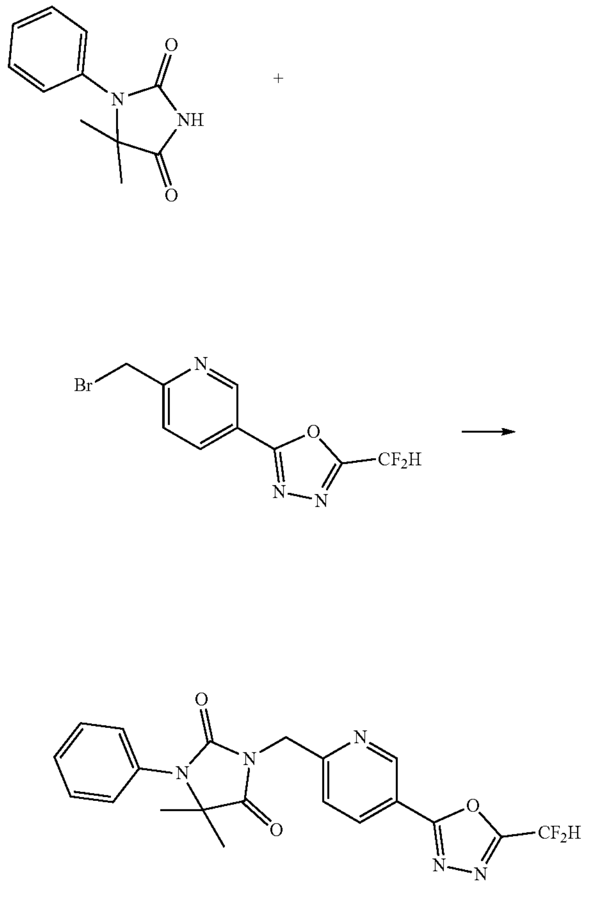

The 5,5-dimethyl-1-phenylimidazolidin-2,4-dione (0.100 g, 0.490 mmol) prepared in step 2, 2-(6-(bromomethyl) pyridin-3-yl)-5-(difluoromethyl)-1,3,4-oxadiazole (0.142 g, 0.490 mmol) and potassium carbonate (0.135 g, 0.979 mmol) were dissolved in N,N-dimethylformamide (5 mL) at 80° C., after which the resulting solution was stirred at the same temperature for 18 hours, and then a reaction was finished by lowering a temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain a title compound (0.080 g, 39.5%) in a white solid form.

$^1$H NMR (400 MHz, $CDCl_3$) δ 9.26~9.25 (m, 1H), 8.37~8.34 (m, 1H), 7.49~7.38 (m, 4H), 7.31~7.23 (m, 2H), 7.08 (s, 0.25H), 6.95 (s, 0.5H), 6.82 (s, 0.25H), 5.02 (s, 2H), 1.52 (s, 6H); LRMS (ES) m/z 414.2 ($M^+$+1).

Synthesis of Compound 19, 3-((5-(5-(difluoromethyl)-1,3,4-oxadiazol-2-yl)pyridin-2-yl)methyl)-5,5-dimethyl-1-(3-(1-methyl-1,2,3,6-tetrahydropyridin-4-yl)phenyl)imidazolidin-2,4-dione

[Step 1] Synthesis of tert-butyl 4-(3-(3-((5-(5-(difluoromethyl)-1,3,4-oxadiazol-2-yl)pyridin-2-yl) methyl)-5,5-dimethyl-2,4-dioxoimidazolidin-1-yl) phenyl)-3,6-dihydropyridin-1(2H)-carboxylate

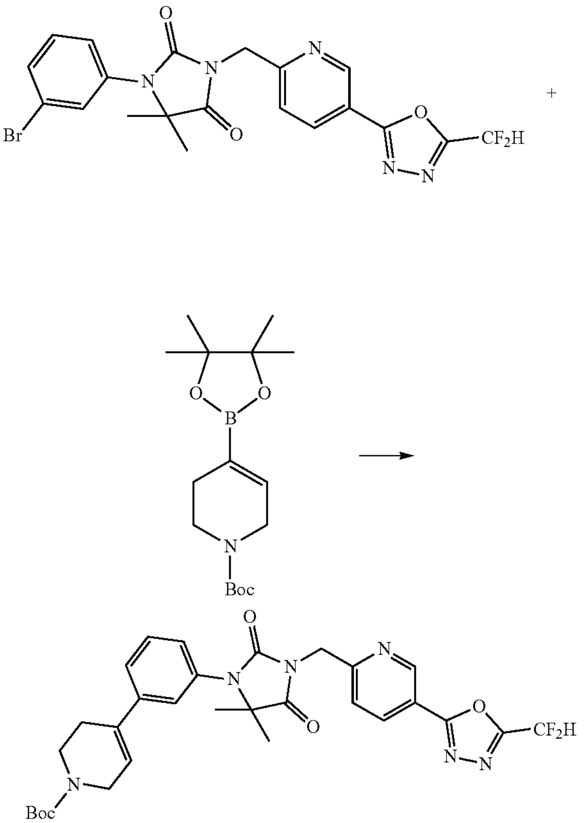

The 1-(3-bromophenyl)-3-((5-(5-(difluoromethyl)-1,3,4-oxadiazol-2-yl)pyridin-2-yl)methyl)-5,5-dimethylimidazolidin-2,4-dione (0.200 g, 0.406 mmol), tert-butyl 4-(4,4,5,5-tetramethyl-1,3,2-dioxaborolan-2-yl)-3,6-dihydropyridin-1(2H)-carboxylate (0.251 g, 0.813 mmol), [1,1'-bis(di-tert-butylphosphino)ferrocene]palladium(II) dichloride (0.026 g, 0.041 mmol) and cesium carbonate (0.199 g, 0.609 mmol) were mixed in 1,2-dichloroethane (6 mL)/water (2 mL), after which the resulting mixture was irradiated with microwave, heated at 100° C. for 20 minutes, and a reaction was finished by lowering a temperature to room temperature. Water was poured into the reaction mixture and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 70%) and concentrated to obtain a title compound (0.140 g, 58.0%) in a colorless oil form.

[Step 2] Synthesis of 3-((5-(5-(difluoromethyl)-1,3,4-oxadiazol-2-yl)pyridin-2-yl)methyl)-5,5-dimethyl-1-(3-(1,2,3,6-tetrahydropyridin-4-yl)phenyl)imidazolidin-2,4-dione 2,2,2-trifluoroacetate

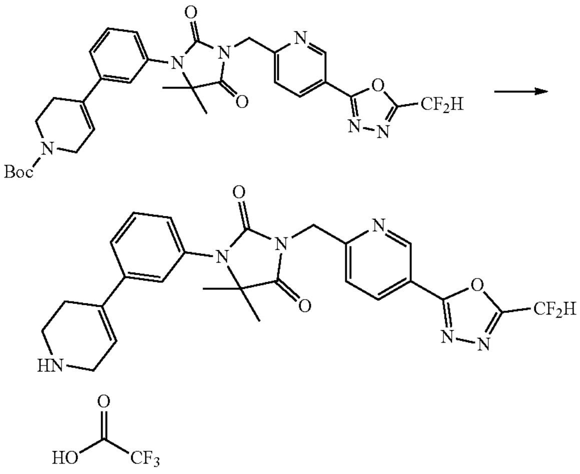

The tert-butyl 4-(3-(3-((5-(5-(difluoromethyl)-1,3,4-oxadiazol-2-yl)pyridin-2-yl)methyl)-5,5-dimethyl-2,4-dioxoimidazolidin-1-yl)phenyl)-3,6-dihydropyridin-1(2H)-carboxylate (0.140 g, 0.235 mmol) prepared in step 1 and trifluoroacetic acid (0.180 mL, 2.354 mmol) were dissolved in dichloromethane (10 mL) at room temperature, after which the resulting solution was stirred at the same temperature for 18 hours. Solvent was removed from the reaction mixture under reduced pressure, after which an obtained product was used without an additional purification process (0.140 g, 97.7%, brown oil).

[Step 3] Synthesis of Compound 19

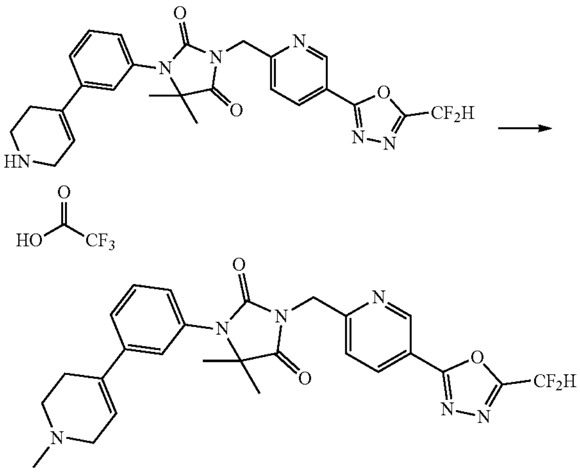

The 3-((5-(5-(difluoromethyl)-1,3,4-oxadiazol-2-yl)pyridin-2-yl)methyl)-5,5-dimethyl-1-(3-(1,2,3,6-tetrahydropyridin-4-yl)phenyl)imidazolidin-2,4-dione 2,2,2-trifluoroacetate (0.080 g, 0.131 mmol) prepared in step 2, formaldehyde (0.008 g, 0.263 mmol), N,N-diisopropylethylamine (0.023 mL, 0.131 mmol) and sodium triacetoxyborohydride (0.056 g, 0.263 mmol) were dissolved in dichloromethane (5 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; methanol/dichloromethane=0 to 10%) and concentrated to obtain a title compound (0.040 g, 59.8%) in a colorless oil form.

$^1$H NMR (400 MHz, $CDCl_3$) δ 9.29 (t, J=1.1 Hz, 1H), 8.39 (dd, J=8.2, 2.2 Hz, 1H), 7.50~7.48 (m, 1H), 7.41~7.39 (m, 2H), 7.29~7.28 (m, 1H), 7.20~7.18 (m, 1H), 7.08 (s, 0.25H), 6.95 (s, 0.5H), 6.82 (s, 0.25H), 6.10~6.08 (m, 1H), 5.02 (s, 2H), 3.16~3.15 (m, 2H), 2.70~2.69 (m, 2H), 2.61~2.60 (m, 2H), 2.43 (s, 3H), 1.53 (s, 6H).

Synthesis of Compound 20, 3-((5-(5-(difluoromethyl)-1,3,4-oxadiazol-2-yl)pyridin-2-yl)methyl)-5,5-dimethyl-1-(3-(1-methylpiperidin-4-yl)phenyl)imidazolidin-2,4-dione

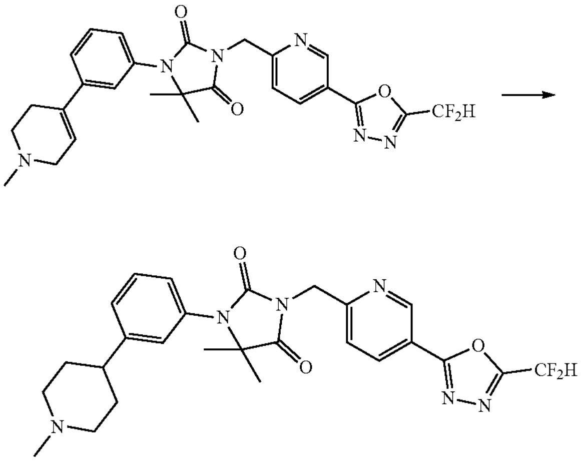

The 3-((5-(5-(difluoromethyl)-1,3,4-oxadiazol-2-yl)pyridin-2-yl)methyl)-5,5-dimethyl-1-(3-(1-methyl-1,2,3,6-tetrahydropyridin-4-yl)phenyl)imidazolidin-2,4-dione (0.034 g, 0.067 mmol) was dissolved in methanol (10 mL) at room temperature, after which 10%-Pd/C (60 mg) was slowly added and stirred for 18 hours in the presence of a hydrogen balloon attached thereto at the same temperature. The reaction mixture was filtered via a celite pad to remove a solid therefrom, after which solvent was removed from the resulting filtrate under reduced pressure, and then an obtained product was used without an additional purification process (0.028 g, 82.0%, colorless oil).

$^1$H NMR (400 MHz, $CDCl_3$) δ d 9.30~9.29 (m, 1H), 8.40 (dd, J=8.2, 2.2 Hz, 1H), 7.50 (d, J=8.2 Hz, 1H), 7.41~7.37 (m, 1H), 7.29~7.27 (m, 1H), 7.16~7.14 (m, 2H), 7.08 (s, 0.25H), 6.95 (s, 0.5H), 6.82 (s, 0.25H), 5.02 (s, 2H), 3.20~3.18 (m, 2H), 2.62~2.55 (m, 1H), 2.45 (s, 3H), 2.29~2.25 (m, 2H), 2.02~1.90 (m, 4H), 1.52 (s, 6H); LRMS (ES) m/z 511.4 ($M^+$+1).

Synthesis of Compound 21, 7-((5-(5-(difluoromethyl)-1,3,4-oxadiazol-2-yl)pyridin-2-yl)methyl)-2-methyl-5-phenyl-2,5,7-triazaspiro[3.4]octan-6,8-dione

[Step 1] Synthesis of benzyl 3-cyano-3-(phenylamino)azetidin-1-carboxylate

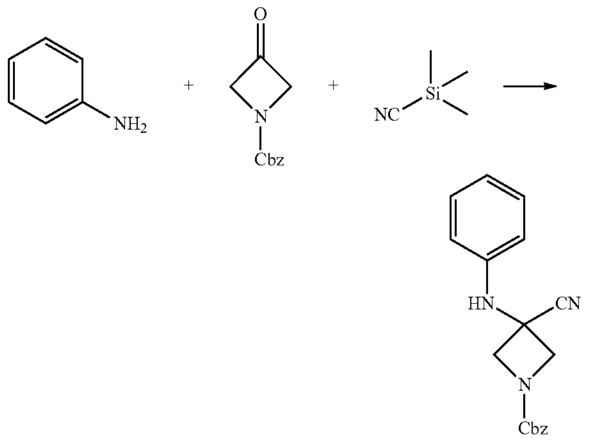

Aniline (1.961 mL, 21.475 mmol), trimethylsilacarbonitrile (2.131 g, 21.475 mmol) and benzyl 3-oxoazetidin-1-carboxylate (4.407 g, 21.475 mmol) were dissolved in acetic acid (20 mL) at room temperature, after which the resulting solution was stirred at the same temperature for 18 hours. Solvent was removed from the reaction mixture under reduced pressure, after which ethyl acetate (10 mL) and hexane (20 mL) were added into the resulting concentrate and stirred to filter out a precipitated solid, washed with hexane, and dried to obtain a title compound (4.700 g, 71.2%) in a white solid form.

[Step 2] Synthesis of benzyl 6,8-dioxo-5-phenyl-2,5,7-triazaspiro[3.4]octan-2-carboxylate

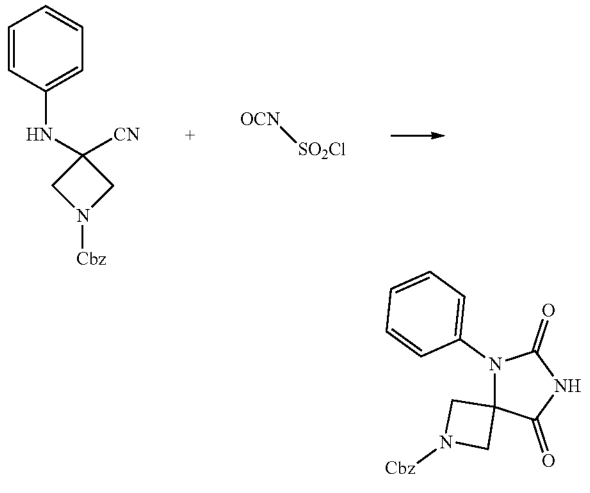

The benzyl 3-cyano-3-(phenylamino)azetidin-1-carboxylate (4.700 g, 15.292 mmol) prepared in step 1 and sulfurisocyanatidic chloride (3.246 g, 22.938 mmol) were dissolved in dichloromethane (50 mL), after which the resulting solution was stirred at 0° C. for 30 minutes and further stirred at room temperature for 18 hours. 1N-hydrochloric acid aqueous solution (10 mL) was poured into the reaction mixture, after which solvent was concentrated under reduced pressure, and then ethanol (30 mL) was added. The resulting mixture was stirred again at 80° C. for 30 minutes, after which solvent was concentrated under reduced pressure. The resulting concentrate was purified via column chromatography ($SiO_2$, 12 g cartridge; ethyl acetate/hexane=0 to 50%) and concentrated to obtain a title compound (2.200 g, 40.9%) in a white solid form.

[Step 3], Synthesis of benzyl 7-((5-(5-(difluoromethyl)-1,3,4-oxadiazol-2-yl)pyridin-2-yl)methyl)-6,8-dioxo-5-phenyl-2,5,7-triazaspiro[3.4]octan-2-carboxylate

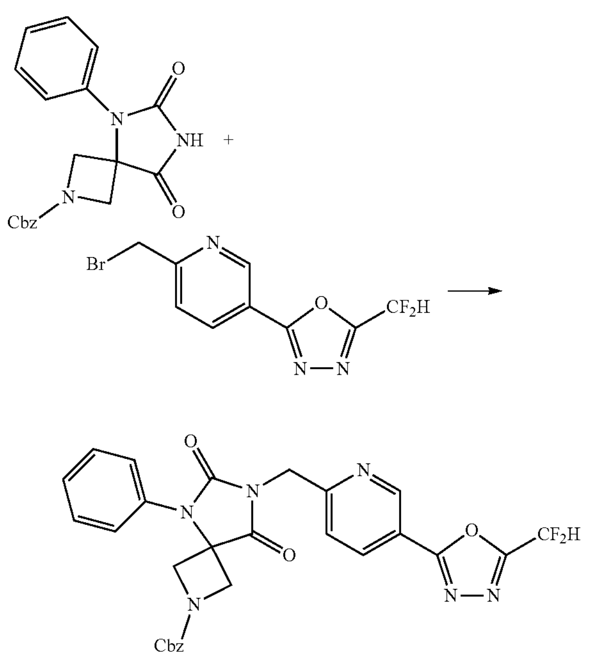

The benzyl 6,8-dioxo-5-phenyl-2,5,7-triazaspiro[3.4]octan-2-carboxylate (0.500 g, 1.423 mmol) prepared in step 2, 2-(6-(bromomethyl)pyridin-3-yl)-5-(difluoromethyl)-1,3,4-oxadiazole (0.413 g, 1.423 mmol) and potassium carbonate (0.393 g, 2.846 mmol) were dissolved in N,N-dimethylformamide (5 mL) at 80° C., after which the resulting solution was stirred at the same temperature for 18 hours, and then a reaction was finished by lowering a temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain a title compound (0.600 g, 75.2%) in a white solid form.

[Step 4] Synthesis of 7-((5-(5-(difluoromethyl)-1,3,4-oxadiazol-2-yl)pyridin-2-yl)methyl)-5-phenyl-2,5,7-triazaspiro[3.4]octan-6,8-dione

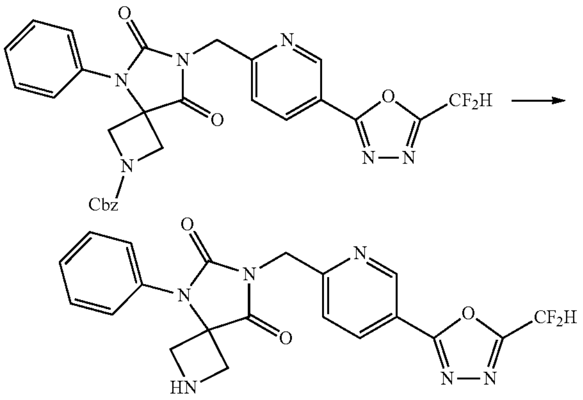

The benzyl 7-((5-(5-(difluoromethyl)-1,3,4-oxadiazol-2-yl)pyridin-2-yl)methyl)-6,8-dioxo-5-phenyl-2,5,7-triazaspiro[3.4]octan-2-carboxylate (0.600 g, 1.070 mmol) prepared in step 3 was dissolved in methanol (10 mL) at room temperature, after which 10%-Pd/C (60 mg) was slowly added and stirred at the same temperature for 18 hours in the presence of a hydrogen balloon attached thereto. The reaction mixture was filtered via a celite pad to remove a solid therefrom, after which solvent was removed from the resulting filtrate under reduced pressure, and then an obtained product was used without an additional purification process (0.450 g, 98.6%, colorless oil).

[Step 5] Synthesis of Compound 21

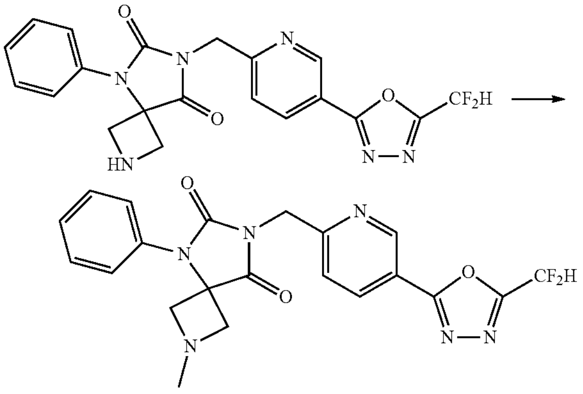

The 7-((5-(5-(difluoromethyl)-1,3,4-oxadiazol-2-yl)pyridin-2-yl)methyl)-5-phenyl-2,5,7-triazaspiro[3.4]octan-6,8-dione (0.150 g, 0.352 mmol) prepared in step 4, formaldehyde (37.00% solution, 0.053 mL, 0.704 mmol) and sodium triacetoxyborohydride (0.149 g, 0.704 mmol) were dissolved in dichloromethane (10 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; methanol/dichloromethane=0 to 10%) and concentrated to obtain a title compound (0.100 g, 64.5%) in a colorless oil form.

$^1$H NMR (400 MHz, $CDCl_3$) δ 9.24 (d, J=2.2 Hz, 1H), 8.36 (dd, J=8.2, 2.2 Hz, 1H), 7.53~7.42 (m, 6H), 7.08 (s, 0.25H), 6.95 (s, 0.5H), 6.82 (s, 0.25H), 4.99 (s, 2H), 3.80~3.73 (m, 4H), 2.31 (s, 3H).

Synthesis of Compound 22, 7-((5-(5-(difluoromethyl)-1,3,4-oxadiazol-2-yl)pyridin-2-yl)methyl)-2-isopropyl-5-phenyl-2,5,7-triazaspiro[3.4]octan-6,8-dione

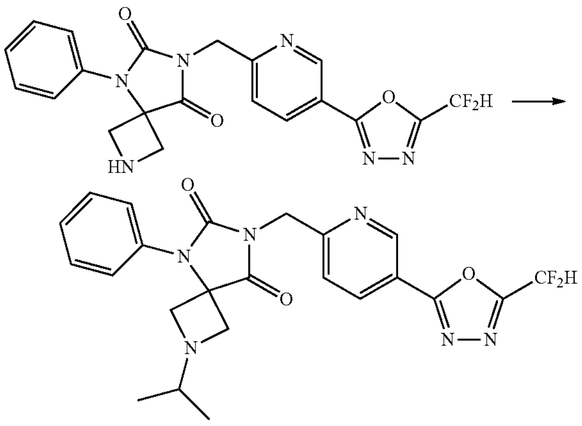

The 7-((5-(5-(difluoromethyl)-1,3,4-oxadiazol-2-yl)pyridin-2-yl)methyl)-5-phenyl-2,5,7-triazaspiro[3.4]octan-6,8-dione (0.100 g, 0.235 mmol), acetone (0.035 mL, 0.469 mmol) and sodium triacetoxyborohydride (0.099 g, 0.469 mmol) were dissolved in dichloromethane (10 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; methanol/dichloromethane=0 to 10%) and concentrated to obtain a title compound (0.070 g, 63.7%) in a colorless oil form.

$^1$H NMR (400 MHz, $CDCl_3$) δ 9.24 (t, J=1.1 Hz, 1H), 8.36 (dd, J=8.2, 2.2 Hz, 4H), 7.51~7.39 (m, 6H), 7.08 (s, 1H), 6.95 (s, 1H), 6.82 (s, 1H), 4.98 (s, 2H), 3.84 (s, 4H), 2.58~2.55 (m, 1H), 0.91~0.87 (m, 6H).

Synthesis of Compound 23, 2-acetyl-7-((5-(5-(difluoromethyl)-1,3,4-oxadiazol-2-yl)pyridin-2-yl)methyl)-5-phenyl-2,5,7-triazaspiro[3.4]octan-6,8-dione

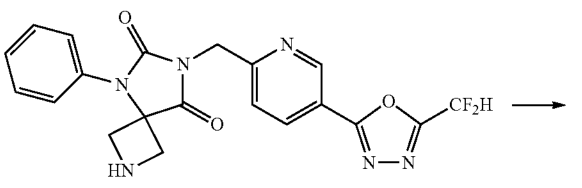

-continued

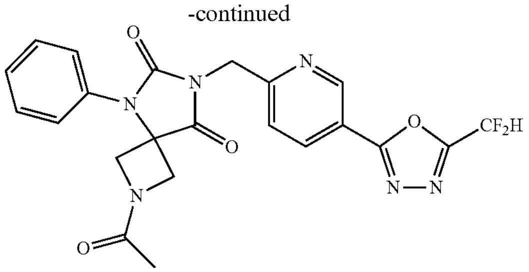

The 7-((5-(5-(difluoromethyl)-1,3,4-oxadiazol-2-yl)pyridin-2-yl)methyl)-5-phenyl-2,5,7-triazaspiro[3.4]octan-6,8-dione (0.124 g, 0.291 mmol), acetyl chloride (0.041 mL, 0.582 mmol) and N,N-diisopropylethylamine (0.101 mL, 0.582 mmol) were dissolved in dichloromethane (5 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; methanol/dichloromethane=0 to 10%) and concentrated to obtain a title compound (0.100 g, 73.4%) in a colorless oil form.

$^1$H NMR (400 MHz, $CDCl_3$) δ 9.26 (t, J=1.1 Hz, 1H), 8.40 (dd, J=8.2, 2.2 Hz, 1H), 7.55~7.39 (m, 6H), 7.08 (s, 0.25H), 6.95 (s, 0.5H), 6.82 (s, 0.25H), 5.03 (s, 2H), 4.62~4.48 (m, 2H), 4.42~4.33 (m, 2H), 1.85 (s, 3H).

Synthesis of Compound 24, 7-((5-(5-(difluoromethyl)-1,3,4-oxadiazol-2-yl)pyridin-2-yl)methyl)-5-phenyl-5,7-diazaspiro[3.4]octan-6,8-dione

[Step 1] Synthesis of 1-(phenylamino)cyclobutan-1-carbonitrile

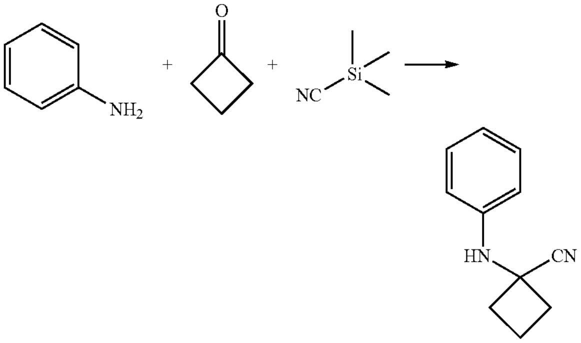

Aniline (0.980 mL, 10.738 mmol), cyclobutanone (0.753 g, 10.738 mmol) and trimethylsilacarbonitrile (1.065 g, 10.738 mmol) were dissolved in acetic acid (20 mL) at room temperature, after which the resulting solution was stirred at the same temperature for 18 hours. Solvent was removed from the reaction mixture under reduced pressure, after which water was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain a title compound (1.200 g, 64.9%) in a white solid form.

[Step 2] Synthesis of 5-phenyl-5,7-diazaspiro[3.4]octan-6,8-dione

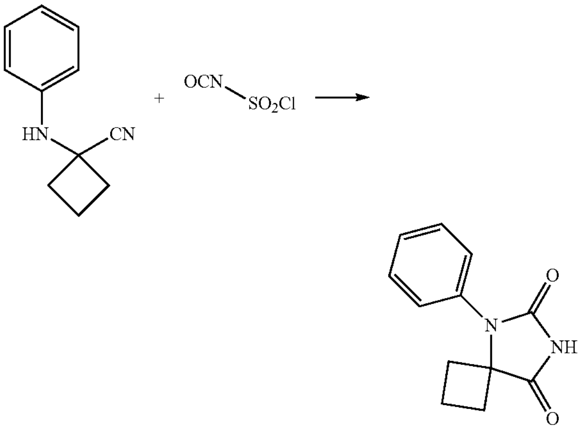

The 1-(phenylamino)cyclobutan-1-carbonitrile (1.000 g, 5.806 mmol) prepared in step 1 and sulfurisocyanatidic chloride (0.761 mL, 8.709 mmol) were dissolved in dichloromethane (20 mL) at room temperature, after which the resulting solution was stirred at the same temperature for 12 hours. After that, 1M HCl (10 mL) was added to the reaction mixture, after which a reaction was finished to remove solvent. Ethanol (10 ml) was added to the reaction mixture and stirred at 80° C. for one hour. Solvent was removed from the reaction mixture under reduced pressure, after which ethyl acetate (20 mL) and hexane (10 mL) were added into the resulting concentrate and stirred to filter out a precipitated solid, washed with hexane, and dried to obtain a title compound (0.950 g, 75.7%) in a white solid form.

[Step 3] Synthesis of Compound 24

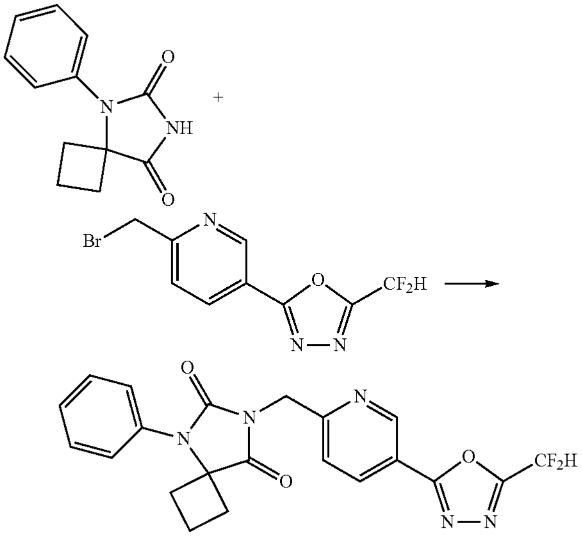

The 5-phenyl-5,7-diazaspiro[3.4]octan-6,8-dione (0.100 g, 0.462 mmol) prepared in step 2 was dissolved in N,N-dimethylformamide (20 mL) at 0° C., after which sodium hydride (60.00%, 0.022 g, 0.555 mmol) was added into the resulting solution and stirred at the same temperature for 30 minutes. 2-(6-(bromomethyl)pyridin-3-yl)-5-(difluoromethyl)-1,3,4-oxadiazole (0.134 g, 0.462 mmol) was added into the reaction mixture and further stirred at room temperature for 2 hours. Water was poured into the reaction mixture and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 40 g cartridge; ethyl acetate/hexane=0 to 50%), and concentrated to obtain a title compound (0.130 g, 66.1%) in a yellow oil form.

$^1H$ NMR (400 MHz, $CDCl_3$) δ 9.30~9.26 (m, 1H), 8.37 (dd, J=8.2, 2.2 Hz, 1H), 7.53~7.43 (m, 4H), 7.33~7.31 (m, 2H), 7.08 (s, 0.25H), 6.95 (s, 0.5H), 6.82 (s, 0.25H), 5.00 (s, 2H), 2.59~2.42 (m, 4H), 2.23~2.04 (m, 2H), 1.69~1.63 (m, 2H).

Synthesis of Compound 25, 3-((5-(5-(difluoromethyl)-1,3,4-oxadiazol-2-yl)pyridin-2-yl)methyl)-1-(4-(furan-3-yl)phenyl)-5,5-dimethylimidazolidin-2,4-dione

[Step 1] Synthesis of 2-((4-bromophenyl)amino)-2-methylpropanenitrile

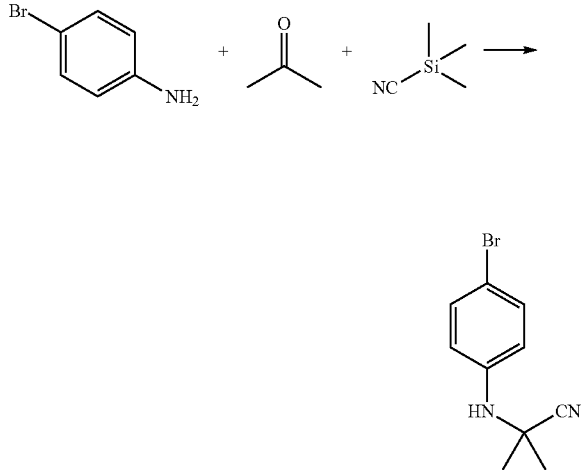

The 4-bromoaniline (3.000 g, 17.439 mmol), propan-2-one (1.013 g, 17.439 mmol) and trimethylsilacarbonitrile (1.730 g, 17.439 mmol) were dissolved in acetic acid (10 mL) at room temperature, after which the resulting solution was stirred at the same temperature for 12 hours. Solvent was removed from the reaction mixture under reduced pressure, after which ethyl acetate (10 mL) and hexane (20 mL) were added into the resulting concentrate and stirred to filter out a precipitated solid, washed with hexane, and dried to obtain a title compound (2.700 g, 64.7%) in a white solid form.

[Step 2] Synthesis of 1-(4-bromophenyl)-5,5-dimethylimidazolidin-2,4-dione

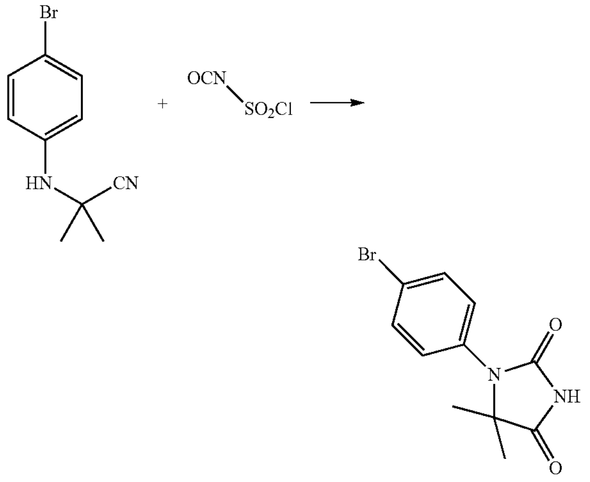

The 2-((4-bromophenyl)amino)-2-methylpropanenitrile (2.740 g, 11.459 mmol) prepared in step 1 and sulfurisocyanatidic chloride (1.502 mL, 17.188 mmol) were dissolved in dichloromethane (5 mL) at room temperature, after which the resulting solution was stirred at the same temperature for 18 hours. 1M HCl (10 mL) was added to the reaction mixture to concentrate an organic layer, after which ethanol (20 mL) was added and stirred at 80° C. for one hour. After that, solvent was removed from the reaction mixture under reduced pressure, after which ethyl acetate (20 mL) and hexane (30 mL) were added into the resulting concentrate and stirred to filter out a precipitated solid, washed with hexane, and dried to obtain a desired compound (2.5 g, 77.1%) in a white solid form.

[Step 3] Synthesis of 1-(4-bromophenyl)-3-((5-(5-(difluoromethyl)-1,3,4-oxadiazol-2-yl)pyridin-2-yl)methyl)-5,5-dimethylimidazolidin-2,4-dione

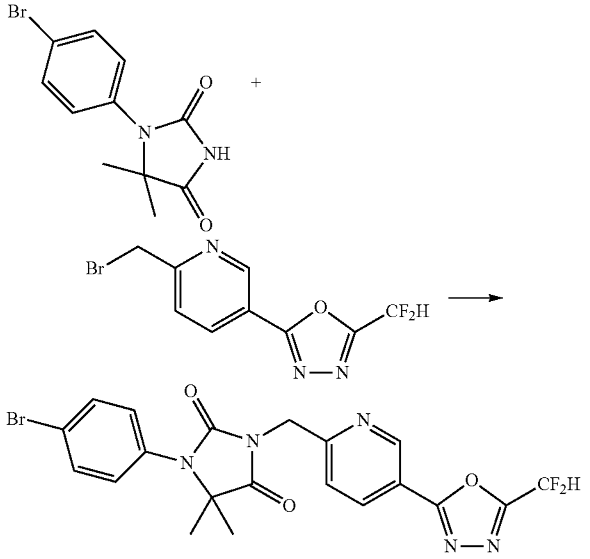

The 1-(4-bromophenyl)-5,5-dimethylimidazolidin-2,4-dione (1.000 g, 3.532 mmol) prepared in step 2, 2-(6-(bromomethyl)pyridin-3-yl)-5-(difluoromethyl)-1,3,4-oxadiazole (1.025 g, 3.532 mmol) and potassium carbonate (0.976 g, 7.064 mmol) were dissolved in N,N-dimethylformamide (30 mL) at 50° C., after which the resulting solution was stirred at the same temperature for 12 hours, and then a reaction was finished by lowering a temperature to room temperature. Water was poured into the reaction mixture and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 40 g cartridge; ethyl acetate/hexane=0 to 50%) and concentrated to obtain a title compound (1.300 g, 74.8%) in a yellow solid form.

[Step 4] Synthesis of Compound 25

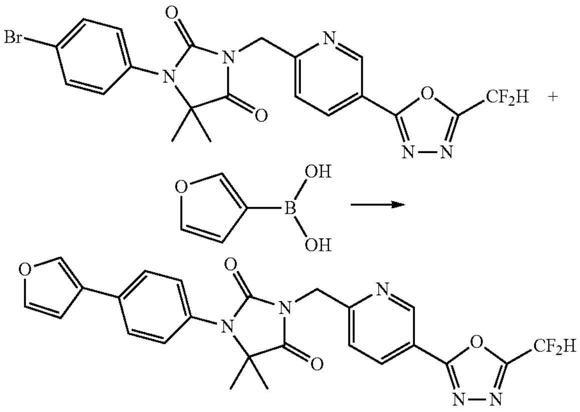

The 1-(4-bromophenyl)-3-((5-(5-(difluoromethyl)-1,3,4-oxadiazol-2-yl)pyridin-2-yl)methyl)-5,5-dimethylimidazolidin-2,4-dione (0.150 g, 0.305 mmol) prepared in step 3, furan-3-ylboronic acid (0.051 g, 0.457 mmol), [1,1'-bis(diphenylphosphino)ferrocene]dichloropalladium (II, 0.020 g, 0.030 mmol) and cesium carbonate (0.149 g, 0.457 mmol) were mixed in 1,4-dioxane (6 mL)/water (2 mL), after which the resulting mixture was irradiated with microwave, then heated at 100° C. for 20 minutes, and then a reaction was finished by lowering a temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; methanol/dichloromethane=0 to 10%), and concentrated to obtain a title compound (0.022 g, 15.1%) in a brown oil form.

$^1H$ NMR (400 MHz, $CDCl_3$) δ 9.30 (dd, J=2.2, 0.8 Hz, 1H), 8.40 (dd, J=8.2, 2.2 Hz, 1H), 7.77~7.74 (m, 2H), 7.52~7.49 (m, 2H), 7.35~7.32 (m, 2H), 7.08 (s, 0.25H), 6.95 (s, 0.5H), 6.82 (s, 0.25H), 6.72 (dd, J=3.4, 0.7 Hz, 1H), 6.51 (dd, J=3.4, 1.8 Hz, 1H), 5.04 (s, 2H), 1.56 (s, 6H); LRMS (ES) m/z 480.3 ($M^+$+1).

Synthesis of Compound 26, 3-((5-(5-(difluoromethyl)-1,3,4-oxadiazol-2-yl)pyridin-2-yl)methyl)-5,5-dimethyl-1-(4-(pyridin-4-yl)phenyl)imidazolidin-2,4-dione

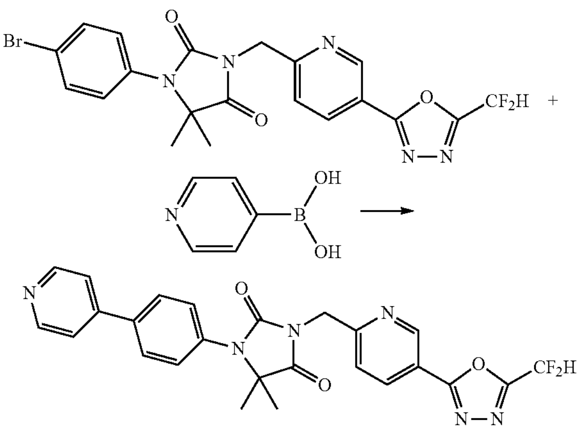

The 1-(4-bromophenyl)-3-((5-(5-(difluoromethyl)-1,3,4-oxadiazol-2-yl)pyridin-2-yl)methyl)-5,5-dimethylimidazolidin-2,4-dione (0.150 g, 0.305 mmol), pyridin-4-ylboronic acid (0.056 g, 0.457 mmol), [1,1'-bis(diphenylphosphino)ferrocene]dichloropalladium (II, 0.020 g, 0.030 mmol) and cesium carbonate (0.149 g, 0.457 mmol) were mixed in 1,4-dioxane (6 mL)/water (2 mL), after which the resulting mixture was irradiated with microwave, then heated at 100° C. for 20 minutes, and then a reaction was finished by lowering a temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; methanol/dichloromethane=0 to 10%), and concentrated to obtain a title compound (0.015 g, 10.0%) in a brown oil form.

$^1H$ NMR (400 MHz, $CDCl_3$) δ 9.29 (dd, J=2.2, 0.8 Hz, 1H), 8.70 (dd, J=4.5, 1.6 Hz, 2H), 8.39 (dd, J=8.2, 2.2 Hz, 1H), 7.73~7.71 (m, 2H), 7.52~7.50 (m, 3H), 7.47~7.45 (m, 2H), 7.08 (s, 0.25H), 6.95 (s, 0.5H), 6.82 (s, 0.25H), 5.04 (s, 2H), 1.60 (s, 6H); LRMS (ES) m/z 491.2 ($M^+$±1).

Synthesis of Compound 27, 3-((5-(5-(difluoromethyl)-1,3,4-oxadiazol-2-yl)pyridin-2-yl)methyl)-5,5-dimethyl-1-(4-(pyridin-3-yl)phenyl)imidazolidin-2,4-dione

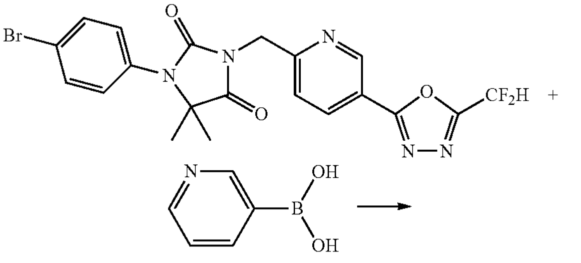

-continued

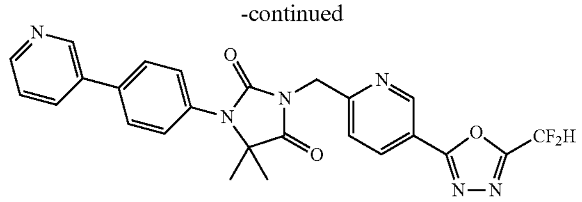

The 1-(4-bromophenyl)-3-((5-(5-(difluoromethyl)-1,3,4-oxadiazol-2-yl)pyridin-2-yl)methyl)-5,5-dimethylimidazolidin-2,4-dione (0.150 g, 0.305 mmol), pyridin-3-ylboronic acid (0.056 g, 0.457 mmol), [1,1'-bis(diphenylphosphino)ferrocene]dichloropalladium (II, 0.020 g, 0.030 mmol) and cesium carbonate (0.149 g, 0.457 mmol) were mixed in 1,4-dioxane (6 mL)/water (2 mL), after which the resulting mixture was irradiated with microwave, then heated at 100° C. for 20 minutes, and then a reaction was finished by lowering a temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; methanol/dichloromethane=0 to 10%), and concentrated to obtain a title compound (0.030 g, 20.1%) in a brown oil form.

$^1H$ NMR (400 MHz, $CDCl_3$) δ 9.30~9.29 (m, 1H), 8.87~8.86 (m, 1H), 8.64 (dd, J=4.8, 1.6 Hz, 1H), 8.40 (dd, J=8.2, 2.2 Hz, 1H), 7.91~7.88 (m, 1H), 7.68~7.65 (m, 2H), 7.52 (d, J=8.2 Hz, 1H), 7.46~7.38 (m, 3H), 7.08 (s, 0.25H), 6.95 (s, 0.5H), 6.82 (s, 0.25H), 5.04 (s, 2H), 1.60 (s, 6H); LRMS (ES) m/z 491.3 ($M^+$+1).

Synthesis of Compound 28, 3-((5-(5-(difluoromethyl)-1,3,4-oxadiazol-2-yl)pyridin-2-yl)methyl)-1-(3'-fluoro-[1,1'-biphenyl]-4-yl)-5,5-dimethylimidazolidin-2,4-dione

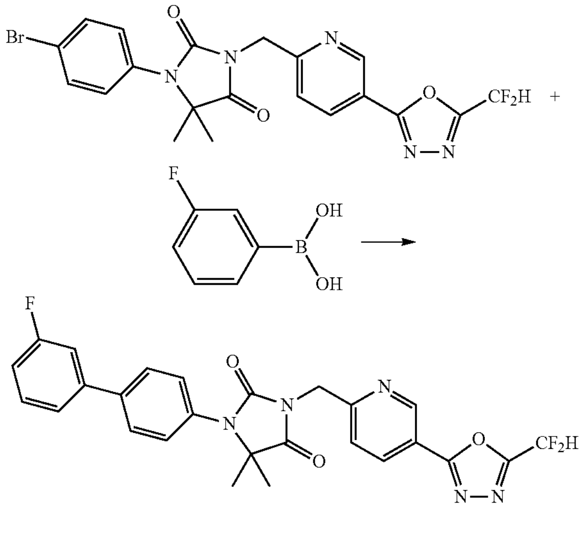

The 1-(4-bromophenyl)-3-((5-(5-(difluoromethyl)-1,3,4-oxadiazol-2-yl)pyridin-2-yl)methyl)-5,5-dimethylimidazolidin-2,4-dione (0.150 g, 0.305 mmol), (3-fluorophenyl)boronic acid (0.064 g, 0.457 mmol) [1,1'-bis(diphenylphosphino)ferrocene]dichloropalladium (II, 0.020 g, 0.030 mmol) and cesium carbonate (0.149 g, 0.457 mmol) were mixed in 1,4-dioxane (6 mL)/water (2 mL), after which the resulting mixture was irradiated with microwave, then heated at 100° C. for 20 minutes, and then a reaction was finished by lowering a temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; methanol/dichloromethane=0 to 10%), and concentrated to obtain a title compound (0.060 g, 38.8%) in a brown oil form.

$^1H$ NMR (400 MHz, $CDCl_3$) δ 9.31~9.30 (m, 1H), 8.40 (dd, J=8.2, 2.2 Hz, 1H), 7.67~7.64 (m, 2H), 7.52 (d, J=8.2 Hz, 1H), 7.45~7.28 (m, 5H), 7.11~7.07 (m, 1H), 7.08 (s, 0.25H), 6.95 (s, 0.5H), 6.82 (s, 0.25H), 5.05 (s, 2H), 1.60 (s, 6H); LRMS (ES) m/z 508.2 ($M^+$+1).

Synthesis of Compound 29, 3-((5-(5-(difluoromethyl)-1,3,4-oxadiazol-2-yl)pyridin-2-yl)methyl)-1-(2'-fluoro-[1,1'-biphenyl]-4-yl)-5,5-dimethylimidazolidin-2,4-dione

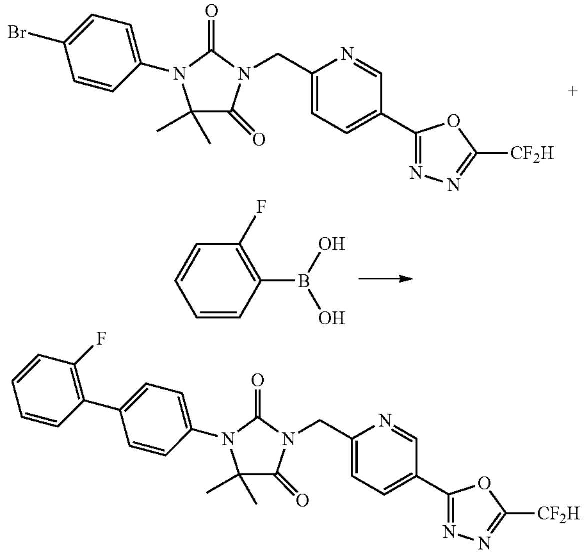

The 1-(4-bromophenyl)-3-((5-(5-(difluoromethyl)-1,3,4-oxadiazol-2-yl)pyridin-2-yl)methyl)-5,5-dimethylimidazolidin-2,4-dione (0.150 g, 0.305 mmol), (2-fluorophenyl)boronic acid (0.064 g, 0.457 mmol) [1,1'-bis(diphenylphosphino)ferrocene]dichloropalladium (II, 0.020 g, 0.030 mmol) and cesium carbonate (0.149 g, 0.457 mmol) were mixed in 1,4-dioxane (6 mL)/water (2 mL), after which the resulting mixture was irradiated with microwave, then heated at 100° C. for 20 minutes, and then a reaction was finished by lowering a temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; methanol/dichloromethane=0 to 10%), and concentrated to obtain a title compound (0.060 g, 38.8%) in a brown oil form.

$^1H$ NMR (400 MHz, $CDCl_3$) δ 9.30~9.29 (m, 1H), 8.40 (dd, J=8.2, 2.2 Hz, 1H), 7.66~7.63 (m, 2H), 7.52~7.33 (m, 5H), 7.26~7.17 (m, 2H), 7.08 (s, 0.25H), 6.95 (s, 0.5H), 6.82 (s, 0.25H), 5.04 (s, 2H), 1.60 (s, 6H); LRMS (ES) m/z 508.2 ($M^+$+1).

Synthesis of Compound 30, tert-butyl 4-(3-((5-(5-(difluoromethyl)-1,3,4-oxadiazol-2-yl)pyridin-2-yl)methyl)-5,5-dimethyl-2,4-dioxoimidazolidin-1-yl)-1H-indol-1-carboxylate

[Step 1] Synthesis of tert-butyl 4-((2-cyanopropan-2-yl)amino)-1H-indol-1-carboxylate

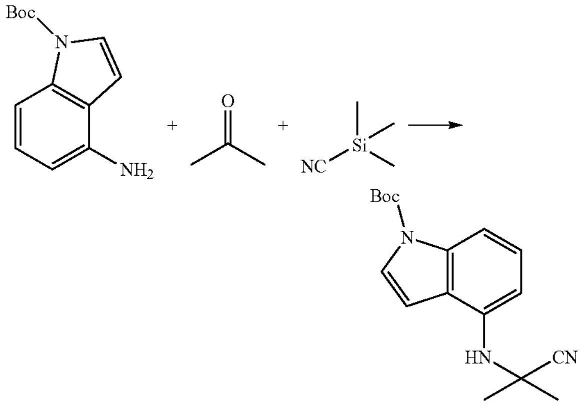

The tert-butyl 4-amino-TH-indol-1-carboxylate (1.680 g, 7.233 mmol), propan-2-one (0.420 g, 7.233 mmol) and trimethylsilacarbonitrile (0.718 g, 7.233 mmol) were dissolved in acetic acid (30 mL) at room temperature, after which the resulting solution was stirred at the same temperature for 18 hours. Solvent was removed from the reaction mixture under reduced pressure, after which ethyl acetate (10 mL) and hexane (20 mL) were added into the resulting concentrate and stirred to filter out a precipitated solid, washed with hexane, and dried to obtain a title compound (1.930 g, 89.1%) in a white solid form.

[Step 2] Synthesis of tert-butyl 4-(5,5-dimethyl-2,4-dioxoimidazolidin-1-yl)-1H-indol-1-carboxylate

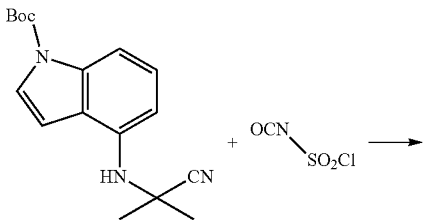

-continued

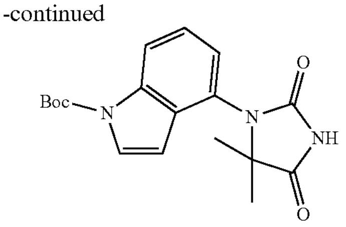

The tert-butyl 4-((2-cyanopropan-2-yl)amino)-1H-indol-1-carboxylate (1.930 g, 6.447 mmol) prepared in step 1 and sulfurisocyanatidic chloride (1.369 g, 9.670 mmol) were dissolved in dichloromethane (30 mL) at room temperature, after which the resulting solution was stirred at the same temperature for 18 hours. 1M HCl (10 mL) was poured into the reaction mixture, and solvent was concentrated under reduced pressure. After that, the resulting concentrate was dissolved in ethanol (20 mL), and then stirred at 80° C. for one hour. A reaction temperature was lowered to room temperature, after which solvent was removed under reduced pressure. Then, the reaction mixture was dissolved in THF (20 mL), after which 10% $K_2CO_3$ solution (10 mL) was added to adjust the pH to 8, and then di-tert-butyl dicarbonate (2.111 g, 9.670 mmol) was added and stirred for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain a title compound (0.250 g, 11.3%) in a white solid form.

[Step 3] Synthesis of Compound 30

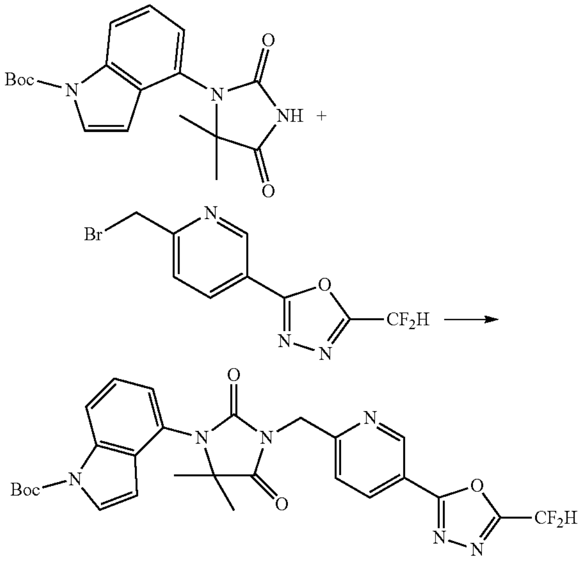

The tert-butyl 4-(5,5-dimethyl-2,4-dioxoimidazolidin-1-yl)-1H-indol-1-carboxylate (0.200 g, 0.582 mmol) prepared in step 2, 2-(6-(bromomethyl)pyridin-3-yl)-5-(difluoromethyl)-1,3,4-oxadiazole (0.169 g, 0.582 mmol) and potassium carbonate (0.161 g, 1.165 mmol) were dissolved in N,N-dimethylformamide (10 mL) at 45° C., after which the resulting solution was stirred at the same temperature for 18 hours, and then a reaction was finished by lowering a temperature to room temperature. Water was poured into the reaction mixture and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain a title compound (0.110 g, 34.2%) in a white solid form.

$^1H$ NMR (400 MHz, $CDCl_3$) 9.33 (d, J=1.6 Hz, 1H), 8.38 (dd, J=8.2, 2.2 Hz, 1H), 8.25~8.23 (m, 1H), 7.66 (d, J=3.8 Hz, 1H), 7.52~7.50 (m, 1H), 7.38 (t, J=8.0 Hz, 1H), 7.16 (dd, J=7.6, 0.6 Hz, 1H), 7.09 (s, 0.25H), 6.96 (s, 0.5H), 6.83 (s, 0.25H), 6.56 (dd, J=3.8, 0.5 Hz, 1H), 5.06 (s, 2H), 1.67 (s, 9H), 1.53 (s, 6H).

Synthesis of Compound 31, tert-butyl 4-(3-((5-(5-(difluoromethyl)-1,3,4-oxadiazol-2-yl)pyridin-2-yl)methyl)-5,5-dimethyl-2,4-dioxoimidazolidin-1-yl)indolin-1-carboxylate

[Step 1] Synthesis of tert-butyl 4-((2-cyanopropan-2-yl)amino)indolin-1-carboxylate

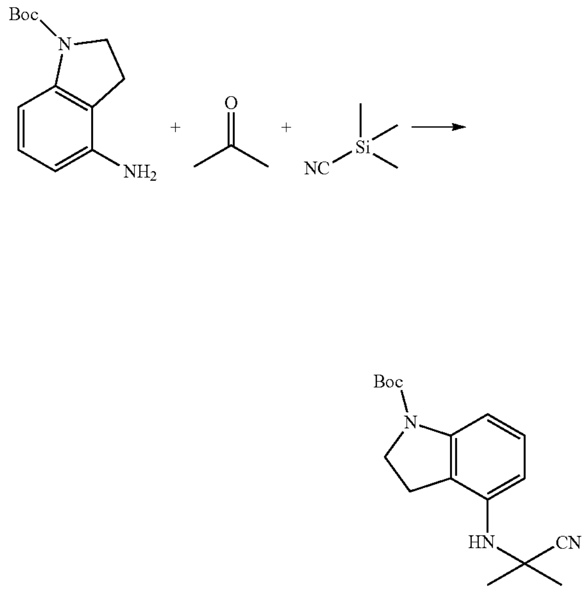

Tert-butyl 4-aminoindolin-1-carboxylate (2.300 g, 9.816 mmol), propan-2-one (0.570 g, 9.816 mmol) and trimethylsilacarbonitrile (0.974 g, 9.816 mmol) were dissolved in acetic acid (30 mL) at room temperature, after which the resulting solution was stirred at the same temperature for 18 hours. Solvent was removed from the reaction mixture under reduced pressure, after which ethyl acetate (10 mL) and hexane (20 mL) were added into the resulting concentrate and stirred to filter out a precipitated solid, washed with hexane, and dried to obtain a title compound (2.800 g, 94.6%) in a white solid form.

[Step 2] Synthesis of tert-butyl 4-(5,5-dimethyl-2,4-dioxoimidazolidin-1-yl)indolin-1-carboxylate

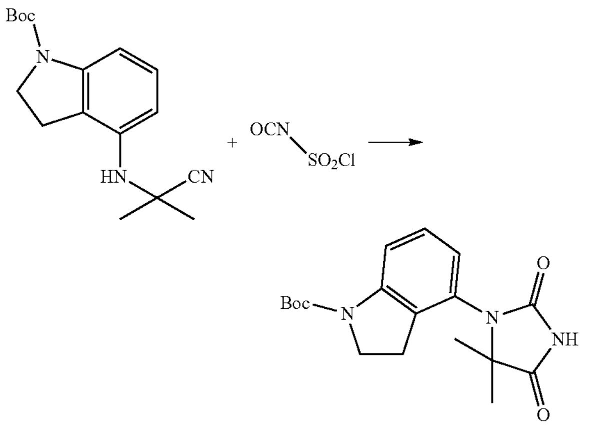

The tert-butyl 4-((2-cyanopropan-2-yl)amino)indolin-1-carboxylate (2.800 g, 9.290 mmol) prepared in step 1 and sulfurisocyanatidic chloride (1.972 g, 13.935 mmol) and di-tert-butyl dicarbonate (3.041 g, 13.935 mmol) were dissolved in dichloromethane (30 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain a title compound (0.490 g, 15.3%) in a white solid form.

[Step 3] Synthesis of Compound 31

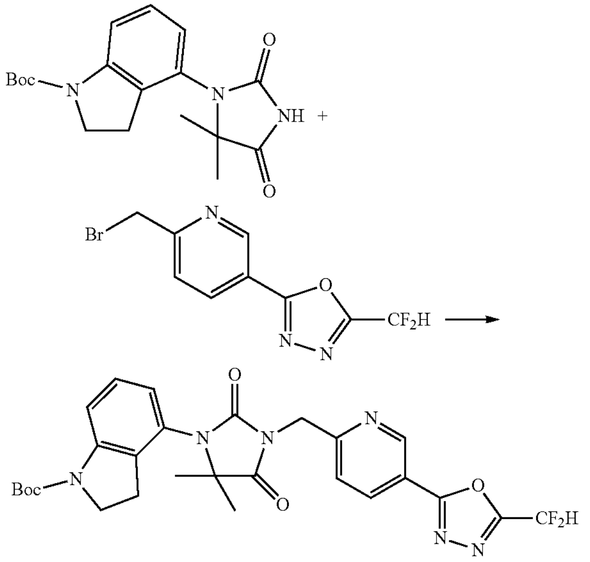

The tert-butyl 4-(5,5-dimethyl-2,4-dioxoimidazolidin-1-yl)indolin-1-carboxylate (0.485 g, 1.404 mmol) prepared in step 2, 2-(6-(bromomethyl)pyridin-3-yl)-5-(difluoromethyl)-1,3,4-oxadiazole (0.407 g, 1.404 mmol) and potassium carbonate (0.388 g, 2.808 mmol) were dissolved in N,N-dimethylformamide (10 mL) at 45° C., after which the resulting solution was stirred at the same temperature for 18 hours, and then a reaction was finished by lowering a temperature to room temperature. Water was poured into the reaction mixture and an extraction was performed with ethyl acetate. An organic layer was washed with saturated sodium chloride aqueous solution, dehydrated with anhydrous sodium sulfate, filtered, and concentrated under reduced pressure. A concentrate was purified via column chromatography ($SiO_2$, 12 g cartridge; ethyl acetate/hexane=0 to 50%), and concentrated to obtain a title compound (0.660 g, 84.8%) in a yellow foamy solid form.

$^1$H NMR (400 MHz, $CDCl_3$) δ 9.28 (dd, J=2.2, 0.7 Hz, 1H), 8.40 (dd, J=8.2, 2.2 Hz, 1H), 7.95 (br s, 1H), 7.50 (dd, J=8.2, 0.7 Hz, 1H), 7.28~7.26 (m, 1H), 7.08 (s, 0.25H), 6.95 (s, 0.5H), 6.82 (s, 0.25H), 6.85~6.83 (m, 1H), 5.02 (s, 2H), 4.04~4.00 (m, 2H), 3.10~3.00 (m, 2H), 1.58~1.54 (m, 15H).

Synthesis of Compound 32, 3-((5-(5-(difluoromethyl)-1,3,4-oxadiazol-2-yl)pyridin-2-yl)methyl)-1-(1H-indol-4-yl)-5,5-dimethylimidazolidin-2,4-dione

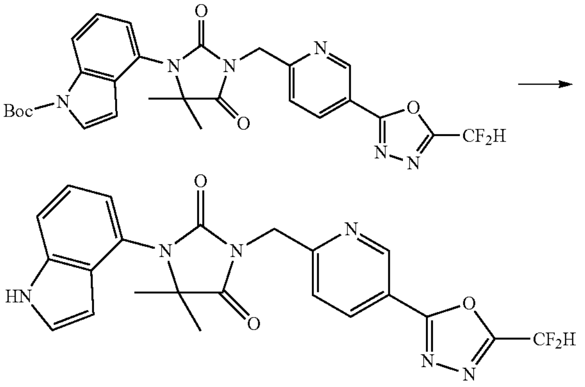

Tert-butyl 4-(3-((5-(5-(difluoromethyl)-1,3,4-oxadiazol-2-yl)pyridin-2-yl)methyl)-5,5-dimethyl-2,4-dioxoimidazolidin-1-yl)-1H-indol-1-carboxylate (0.258 g, 0.467 mmol) and trifluoroacetic acid (0.358 mL, 4.669 mmol) were dissolved in dichloromethane (10 mL) at room temperature, after which the resulting solution was stirred at the same temperature for 18 hours. Solvent was removed from the reaction mixture under reduced pressure, after which saturated sodium hydrogen carbonate aqueous solution was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. An obtained product was used without an additional purification process (0.200 g, 94.7%, gray solid). $^1$H NMR (400 MHz, DMSO-d6) 9.21 (d, J=1.9 Hz, 1H), 8.48 (dd, J=8.2, 2.2 Hz, 1H), 7.72 (s, 0.25H), 7.69 (d, J=8.2 Hz, 1H), 7.59 (s, 0.5H), 7.50 (d, J=8.1 Hz, 1H), 7.46 (s, 0.25H), 7.40 (t, J=2.8 Hz, 1H), 6.99 (d, J=7.0 Hz, 1H), 6.42 (t, J=2.2 Hz, 1H), 5.75 (s, 1H), 4.96 (s, 2H), 1.42 (s, 6H).

Synthesis of Compound 33, 3-((5-(5-(difluoromethyl)-1,3,4-oxadiazol-2-yl)pyridin-2-yl)methyl)-1-(indolin-4-yl)-5,5-dimethylimidazolidin-2,4-dione

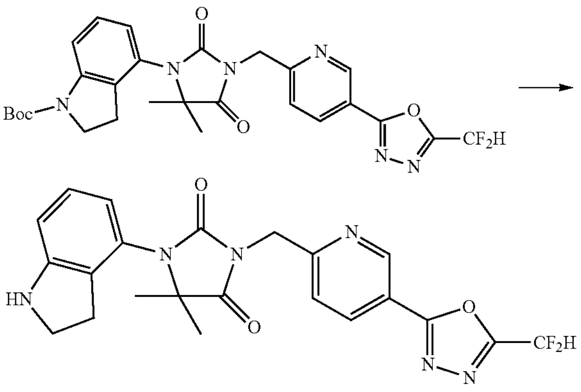

Tert-butyl 4-(3-((5-(5-(difluoromethyl)-1,3,4-oxadiazol-2-yl)pyridin-2-yl)methyl)-5,5-dimethyl-2,4-dioxoimidazolidin-1-yl)indolin-1-carboxylate (0.670 g, 1.208 mmol) and trifluoroacetic acid (0.925 mL, 12.082 mmol) were dissolved in dichloromethane (10 mL) at room temperature, after which the resulting solution was stirred at the same temperature for 18 hours. Solvent was removed from the reaction mixture under reduced pressure, after which saturated sodium hydrogen carbonate aqueous solution was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. An obtained product was used without an additional purification process (title compound, 0.500 g, 91.1%, yellow foamy solid).

$^1$H NMR (400 MHz, $CDCl_3$) δ 9.28 (t, J=1.1 Hz, 1H), 8.39 (dd, J=8.2, 2.2 Hz, 1H), 7.50~7.47 (m, 1H), 7.08 (dd, J=8.1, 7.6 Hz, 1H), 7.08 (s, 0.25H), 6.95 (s, 0.5H), 6.82 (s, 0.25H), 6.67 (d, J=7.8 Hz, 1H), 6.58~6.55 (m, 1H), 5.04 (s, 2H), 3.62~3.56 (m, 2H), 3.01~2.97 (m, 2H), 1.58 (s, 6H).

Synthesis of Compound 34, 3-((5-(5-(difluoromethyl)-1,3,4-oxadiazol-2-yl)pyridin-2-yl)methyl)-5,5-dimethyl-1-(3-nitrophenyl)imidazolidin-2,4-dione

[Step 1] Synthesis of 2-methyl-2-((3-nitrophenyl)amino)propanenitrile

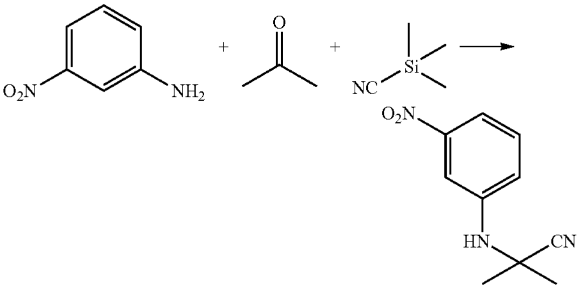

The 3-nitroaniline (3.000 g, 21.719 mmol), propan-2-one (1.261 g, 21.719 mmol) and trimethylsilacarbonitrile (2.155 g, 21.719 mmol) were dissolved in acetic acid (30 mL) at room temperature, after which the resulting solution was stirred at the same temperature for 18 hours. Solvent was removed from the reaction mixture under reduced pressure, after which ethyl acetate (10 mL) and hexane (20 mL) were added into the resulting concentrate and stirred to filter out a precipitated solid, washed with hexane, and dried to obtain a title compound (4.000 g, 89.7%) in a yellow solid form.

[Step 2] Synthesis of 5,5-dimethyl-1-(3-nitrophenyl)imidazolidin-2,4-dione

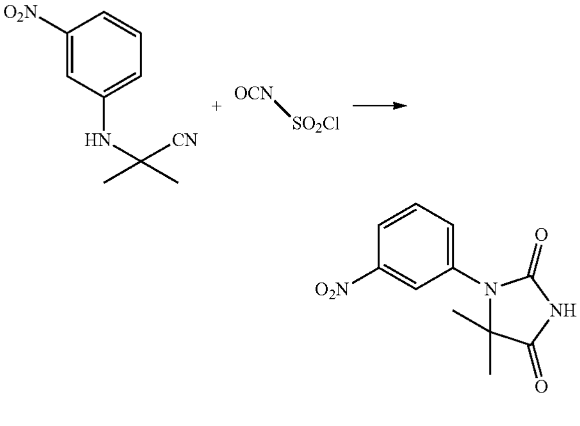

The 2-methyl-2-((3-nitrophenyl)amino)propanenitrile (4.000 g, 19.491 mmol) prepared in step 1 and sulfurisocyanatidic chloride (4.138 g, 29.237 mmol) were dissolved in dichloromethane (5 mL) at room temperature, after which the resulting solution was stirred at the same temperature for 18 hours. 1M HCl (10 mL) was poured into the reaction mixture, and solvent was concentrated under reduced pressure. After that, the resulting concentrate was dissolved in ethanol (20 mL), and then stirred at 80° C. for one hour. A precipitated solid was filtered, washed with hexane, and dried to obtain a title compound (4.300 g, 88.5%) in a yellow solid form.

[Step 3] Synthesis of Compound 34

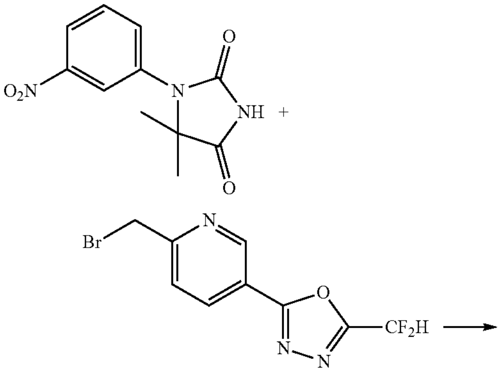

-continued

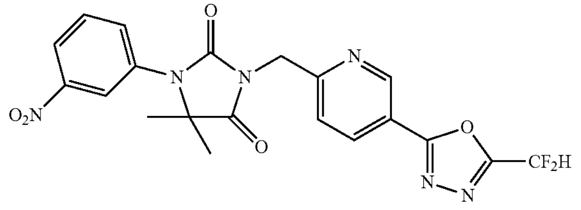

The 5,5-dimethyl-1-(3-nitrophenyl)imidazolidin-2,4-dione (1.000 g, 4.012 mmol) prepared in step 2, 2-(6-(bromomethyl)pyridin-3-yl)-5-(difluoromethyl)-1,3,4-oxadiazole (1.164 g, 4.012 mmol) and potassium carbonate (1.109 g, 8.025 mmol) were dissolved in N,N-dimethylformamide (20 mL) at 45° C., after which the resulting solution was stirred at the same temperature for 18 hours, and then a reaction was finished by lowering a temperature to room temperature. Water was poured into the reaction mixture and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 40 g cartridge; ethyl acetate/hexane=0 to 50%), and concentrated to obtain a title compound (1.400 g, 76.1%) in a foamy white solid form.

$^1H$ NMR (400 MHz, $CDCl_3$) δ 9.30 (d, J=1.6 Hz, 1H), 8.42 (dd, J=8.2, 2.2 Hz, 1H), 8.28~8.25 (m, 2H), 7.76~7.73 (m, 1H), 7.69~7.65 (m, 1H), 7.53~7.51 (m, 1H), 7.08 (s, 0.25H), 6.95 (s, 0.5H), 6.82 (s, 0.25H), 5.05 (s, 2H), 1.63 (s, 6H).

Synthesis of Compound 35, 1-(3-aminophenyl)-3-((5-(5-(difluoromethyl)-1,3,4-oxadiazol-2-yl)pyridin-2-yl)methyl)-5,5-dimethylimidazolidin-2,4-dione

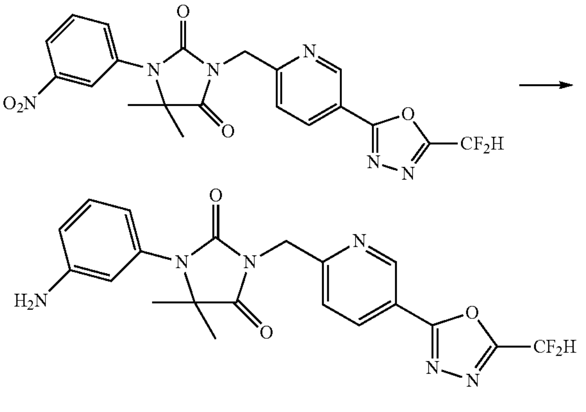

The 3-((5-(5-(difluoromethyl)-1,3,4-oxadiazol-2-yl)pyridin-2-yl)methyl)-5,5-dimethyl-1-(3-nitrophenyl)imidazolidin-2,4-dione (1.400 g, 3.054 mmol) was dissolved in methanol (30 mL) at room temperature, after which Raney nickel was slowly added and stirred for 12 hours in the presence of a hydrogen balloon attached thereto at the same temperature. The reaction mixture was filtered via a celite pad to remove a solid therefrom, after which solvent was removed from a resulting filtrate under reduced pressure, and then an obtained product was used without an additional purification process (1.200 g, 91.7%, white solid).

$^1$H NMR (400 MHz, $CDCl_3$) δ 9.30 (d, J=1.7 Hz, 1H), 8.40 (dd, J=8.2, 2.2 Hz, 1H), 7.50 (d, J=8.2 Hz, 1H), 7.23 (t, J=8.0 Hz, 1H), 7.08 (s, 0.25H), 6.95 (s, 0.5H), 6.82 (s, 0.25H), 6.73~6.68 (m, 2H), 6.62~6.61 (m, 1H), 5.02 (s, 2H), 3.78 (br s, 2H), 1.55 (s, 6H); LRMS (ES) m/z 429.3 ($M^+$+1).

Synthesis of Compound 36, N-(3-(3-((5-(5-(difluoromethyl)-1,3,4-oxadiazol-2-yl)pyridin-2-yl)methyl)-5,5-dimethyl-2,4-dioxoimidazolidin-1-yl)phenyl)acetamide

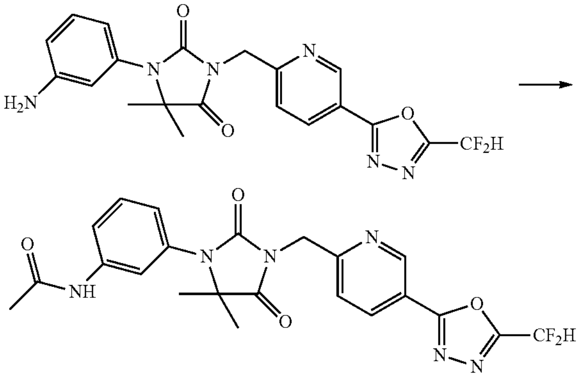

The 1-(3-aminophenyl)-3-((5-(5-(difluoromethyl)-1,3,4-oxadiazol-2-yl)pyridin-2-yl)methyl)-5,5-dimethylimidazolidin-2,4-dione (0.140 g, 0.327 mmol), acetic anhydride (0.031 mL, 0.327 mmol) and N,N-diisopropylethylamine (0.114 mL, 0.654 mmol) were dissolved in dichloromethane (10 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%), and concentrated to obtain a title compound (0.110 g, 71.6%) in a foamy white solid form.

$^1$H NMR (400 MHz, $CDCl_3$) δ 9.26 (dd, J=2.1, 0.7 Hz, 1H), 8.38 (dd, J=8.2, 2.2 Hz, 1H), 8.22 (s, 1H), 7.68 (t, J=1.9 Hz, 1H), 7.50 (dd, J=8.2, 0.5 Hz, 1H), 7.25 (t, J=8.0 Hz, 1H), 7.17~7.14 (m, 1H), 7.08 (s, 0.25H), 6.95 (s, 0.5H), 6.97~6.95 (m, 1H), 6.82 (s, 0.25H), 5.02 (s, 2H), 1.99 (s, 3H), 1.52 (s, 6H).

Synthesis of Compound 37, 1-(1-acetylindolin-4-yl)-3-((5-(5-(difluoromethyl)-1,3,4-oxadiazol-2-yl)pyridin-2-yl)methyl)-5,5-dimethylimidazolidin-2,4-dione

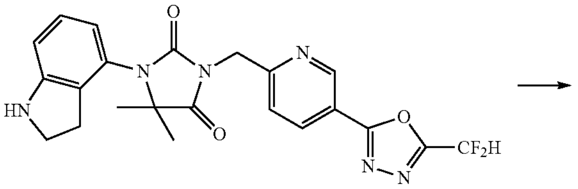

-continued

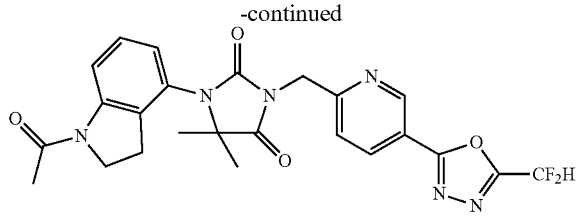

The 3-((5-(5-(difluoromethyl)-1,3,4-oxadiazol-2-yl)pyridin-2-yl)methyl)-1-(indolin-4-yl)-5,5-dimethylimidazolidin-2,4-dione (0.100 g, 0.220 mmol), acetic anhydride (0.021 mL, 0.220 mmol) and N,N-diisopropylethylamine (0.077 mL, 0.440 mmol) were dissolved in dichloromethane (10 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%), and concentrated to obtain a title compound (0.080 g, 73.2%) in a foamy white solid form.

$^1$H NMR (400 MHz, $CDCl_3$) δ 9.24~9.23 (m, 1H), 8.37 (dd, J=8.2, 2.2 Hz, 1H), 8.27 (d, J=8.1 Hz, 1H), 7.49 (dd, J=8.2, 0.6 Hz, 1H), 7.29~7.25 (m, 1H), 7.08 (s, 1H), 6.95 (s, 1H), 6.92 (d, J=7.6 Hz, 1H), 6.82 (s, 1H), 5.00 (s, 2H), 4.14~4.07 (m, 2H), 3.16~3.14 (m, 2H), 2.22 (s, 3H), 1.52 (s, 6H).

Protocol for Measuring and Analyzing the Activity of the Inventive Compound

<Experimental Example 1> Identification of HDAC Enzyme Activity Inhibition (In Vitro)

A selective HDAC6 inhibitor is important for selectivity of HDAC1 inhibition, which is a cause of side effects, and thus HDAC1/6 enzyme selectivity and cell selectivity (HDAC1: histone acetylation/HDAC6: tubulin acetylation) were identified.

1. Experimental Method

A HDAC enzyme inhibitory capacity of a test material was measured by using HDAC1 Fluorimetric Drug Discovery Assay Kit (Enzolifesciences: BML-AK511) and HDAC6 human recombinant (Calbiochem: 382180). For a HDAC1 assay, samples were treated at a concentration of 100, 1000 and 10000 nM. For a HDAC6 assay, samples were treated at a concentration of 0.1, 1, 10, 100 and 1000 nM. After the above sample treatment, a reaction was continued at 37° C. for 60 minutes, treated with a developer, and subjected to reaction at 37° C. for 30 minutes, after which fluorescence intensity (Ex 390, Em 460) was measured by using FlexStatin3 (Molecular device).

2. Experimental Results

The results of searching HDAC enzyme activity inhibition obtained according to the above experimental method are shown in Table 2.

TABLE 2

| Compound | HDAC6 $IC_{50}$ (μM) | HDAC1 $IC_{50}$ (μM) |
|---|---|---|
| 1 | 0.665 | >10 |
| 2 | 0.958 | >10 |
| 3 | 0.219 | >10 |
| 4 | 0.099 | >10 |
| 5 | 0.206 | >10 |
| 6 | 0.104 | >10 |
| 7 | 0.100 | >10 |
| 8 | 0.099 | >10 |
| 9 | 0.147 | >10 |
| 10 | 0.053 | >10 |
| 11 | 0.056 | >10 |
| 12 | 0.060 | >10 |
| 13 | 0.027 | >10 |
| 14 | 0.056 | >10 |
| 15 | 0.043 | >10 |
| 16 | 0.142 | >10 |
| 17 | 0.069 | >10 |
| 18 | 0.079 | >10 |
| 19 | 0.085 | >10 |
| 20 | 0.090 | >10 |
| 21 | 0.241 | >10 |
| 22 | 0.191 | >10 |
| 23 | 0.369 | >10 |
| 24 | 0.056 | >10 |
| 25 | 0.106 | >10 |
| 26 | 0.048 | >10 |
| 27 | 0.055 | >10 |
| 28 | 0.168 | >10 |
| 29 | 0.165 | >10 |
| 30 | 0.578 | >10 |
| 31 | 0.316 | >10 |
| 32 | 0.055 | >10 |
| 33 | 0.058 | >10 |
| 34 | 0.046 | >10 |
| 35 | 0.052 | >10 |
| 36 | 0.035 | >10 |
| 37 | 0.068 | >10 |

Referring to Table 2, it can be confirmed that the 1,3,4-oxadiazole derivative compounds according to the present invention show excellent HDAC1/6 enzyme selectivity.

The invention claimed is:

1. A compound represented by a following chemical formula I, stereoisomers thereof or pharmaceutically acceptable salts thereof:

[Chemical Formula I]

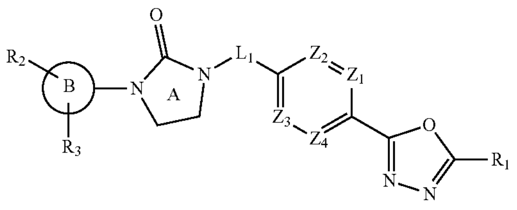

wherein, $Z_1$ to $Z_4$ are each independently N or $CR_0$ wherein $R_0$ is H or halogen;

$R_1$ is $CX_3$ or $CX_2H$ wherein X is halogen;

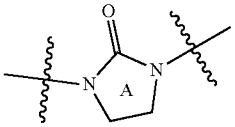

is

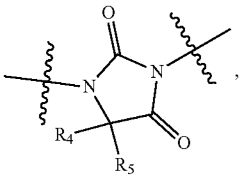

,

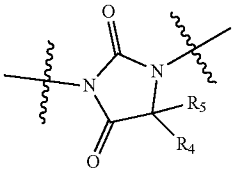

or

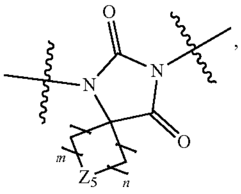

, $R_4$ and $R_5$ are each independently H or C1-C4 alkyl, $Z_5$ is N—$R_6$ or $CH_2$, $R_6$ is H, C1-C4 alkyl, —C(═O)—(C1-C4 alkyl), —C(—O)—O—(C1-C4 alkyl) or 4- to 6-membered heterocycloalkyl having one O;

$L_1$ is —(C1-C2 alkylene)-;

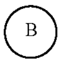

is C6-C12 aryl, 5- to 9-membered heteroaryl having at least one N or

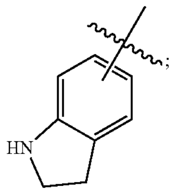

;

$R_2$ and $R_3$ are each independently H, halogen, C1-C4 alkyl, C6-C12 aryl, 5- or 6-membered heteroaryl having N or O, 5- or 6-membered heterocycloalkyl having N, 5- or 6-membered heterocycloalkenyl having N, —C(—O)—O—(C1-C4 alkyl), —C(—O)—(C1-C4 alkyl), —NH—C(═O)—(C1-C4 alkyl), —$NO_2$ or —$NH_2$, at least one H of above $R_2$ and $R_3$ may be each independently substituted with halogen or C1-C4 alkyl; and n and m are each independently 1 or 2.

2. The compound represented by the chemical formula I, stereoisomers thereof or pharmaceutically acceptable salts thereof according to claim 1, wherein $Z_1$ and $Z_2$ are each independently N, CH or CF, and $Z_3$ and $Z_4$ are each CH;

$R_1$ is $CF_3$ or $CF_2H$;

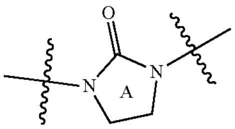

is

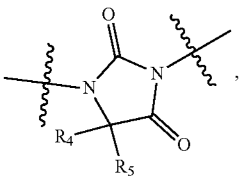

,

-continued

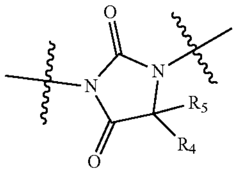

or

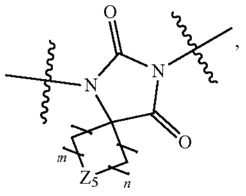

$R_4$ and $R_5$ are each independently H or C1-C4 alkyl, $Z_5$ is N—$R_6$ or $CH_2$, $R_6$ is H, C1-C4 alkyl, —C(═O)—(C1-C4 alkyl), —C(═O)—O—(C1-C4 alkyl) or oxetane;

$L_1$ is —(C1-C2 alkylene)-;

$R_2$ and $R_3$ are each independently H, halogen, C1-C4 alkyl, halogen substituted or unsubstituted phenyl, furanyl, pyridinyl, C1-C4 alkyl substituted or unsubstituted piperidinyl, C1-C4 alkyl substituted or unsubstituted tetrahydropyridinyl, —C(═O)—O—(C1-C4 alkyl), —C(═O)—(C1-C4 alkyl), —NH—C(—O)—(C1-C4 alkyl), —$NO_2$ or —$NH_2$,

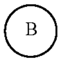

is phenyl, indole or

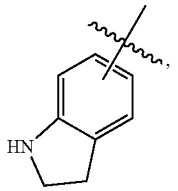

if

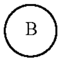

is indole or

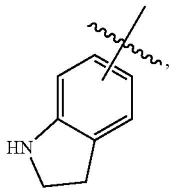

H of NH thereof may be substituted with —C(═O)—O—(C1-C4 alkyl) or —C(═O)—(C1-C4 alkyl), if

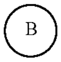

is phenyl, at least one H of phenyl may be each independently substituted with halogen, and n and m are each independently 1 or 2.

3. The compound represented by the chemical formula I, stereoisomers thereof or pharmaceutically acceptable salts thereof according to claim 1, wherein the compound represented by chemical formula I is one selected from the group consisting of following compounds 1 to 37:

| Compound | Structure |
| --- | --- |
| 1 | 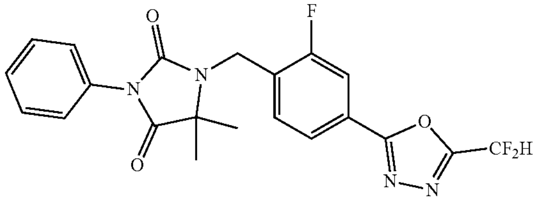 [SMILES: CC1(C)C(=O)N(c2ccccc2)C(=O)N1Cc1ccc(-c2nnc(C(F)F)o2)cc1F] |
| 2 | 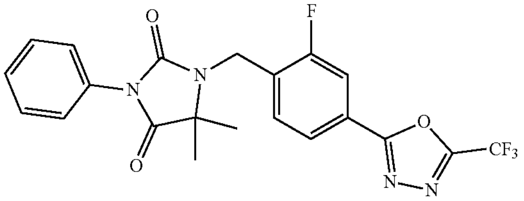 [SMILES: CC1(C)C(=O)N(c2ccccc2)C(=O)N1Cc1ccc(-c2nnc(C(F)(F)F)o2)cc1F] |

-continued
| Compound | Structure |
| --- | --- |
| 3 | 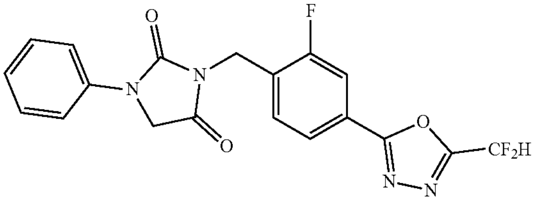 [SMILES: O=C1CN(c2ccccc2)C(=O)N1Cc1ccc(-c2nnc(C(F)F)o2)cc1F] |
| 4 | 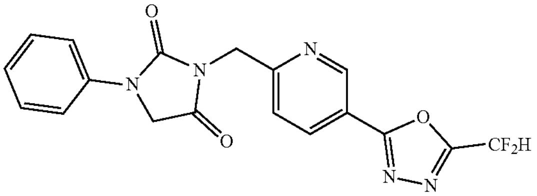 [SMILES: O=C1CN(c2ccccc2)C(=O)N1Cc1ccc(-c2nnc(C(F)F)o2)cn1] |
| 5 | 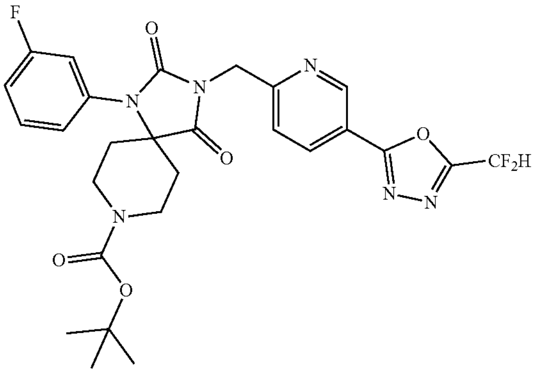 [SMILES: CC(C)(C)OC(=O)N1CCC2(CC1)C(=O)N(Cc1ccc(-c3nnc(C(F)F)o3)cn1)C(=O)N2c1cccc(F)c1] |
| 6 | 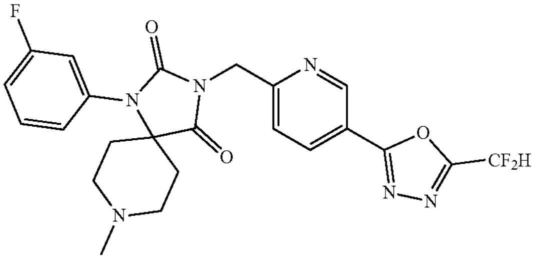 [SMILES: CN1CCC2(CC1)C(=O)N(Cc1ccc(-c3nnc(C(F)F)o3)cn1)C(=O)N2c1cccc(F)c1] |
| 7 | 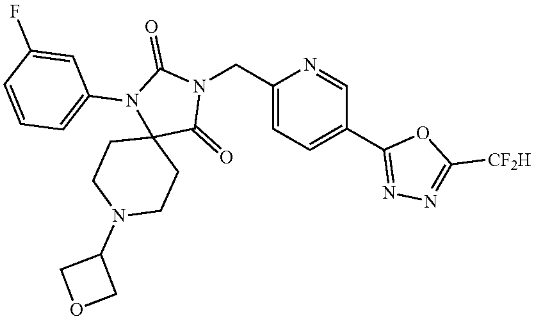 [SMILES: O=C1N(Cc2ccc(-c3nnc(C(F)F)o3)cn2)C(=O)C2(CCN(C3COC3)CC2)N1c1cccc(F)c1] |

-continued
| Compound | Structure |
| --- | --- |
| 8 | 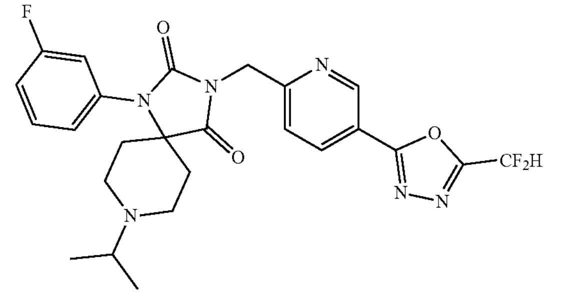 [SMILES: CC(C)N1CCC2(CC1)C(=O)N(Cc1ccc(-c3nnc(C(F)F)o3)cn1)C(=O)N2c1cccc(F)c1] |
| 9 | 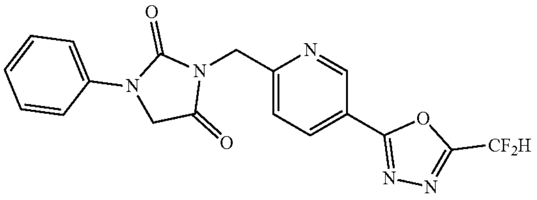 [SMILES: O=C1CN(c2ccccc2)C(=O)N1Cc1ccc(-c2nnc(C(F)F)o2)cn1] |
| 10 | 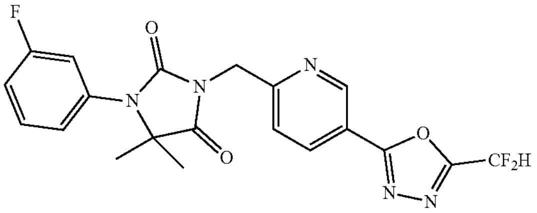 [SMILES: CC1(C)C(=O)N(Cc2ccc(-c3nnc(C(F)F)o3)cn2)C(=O)N1c1cccc(F)c1] |
| 11 | 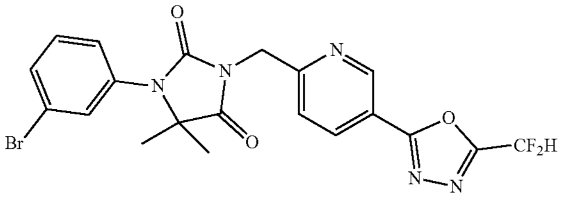 [SMILES: CC1(C)C(=O)N(Cc2ccc(-c3nnc(C(F)F)o3)cn2)C(=O)N1c1cccc(Br)c1] |
| 12 | 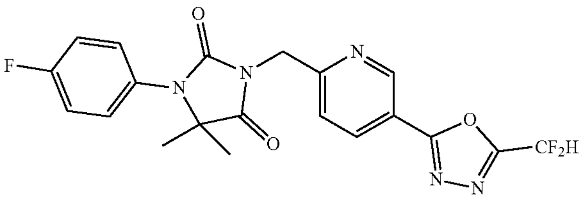 [SMILES: CC1(C)C(=O)N(Cc2ccc(-c3nnc(C(F)F)o3)cn2)C(=O)N1c1ccc(F)cc1] |
| 13 | 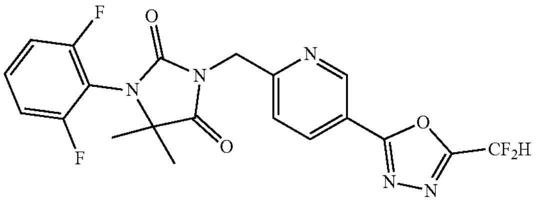 [SMILES: CC1(C)C(=O)N(Cc2ccc(-c3nnc(C(F)F)o3)cn2)C(=O)N1c1c(F)cccc1F] |
| 14 | 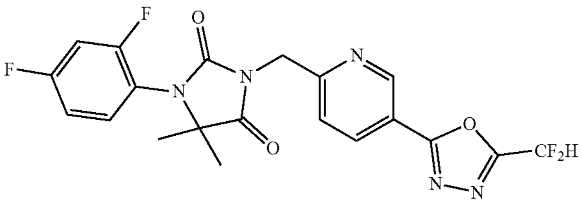 [SMILES: CC1(C)C(=O)N(Cc2ccc(-c3nnc(C(F)F)o3)cn2)C(=O)N1c1ccc(F)cc1F] |

-continued
| Compound | Structure |
|---|---|
| 15 | 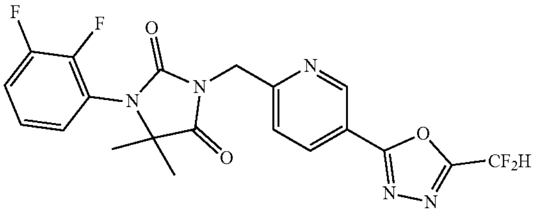 [SMILES: CC1(C)C(=O)N(Cc2ccc(-c3nnc(C(F)F)o3)cn2)C(=O)N1c1cccc(F)c1F] |
| 16 | 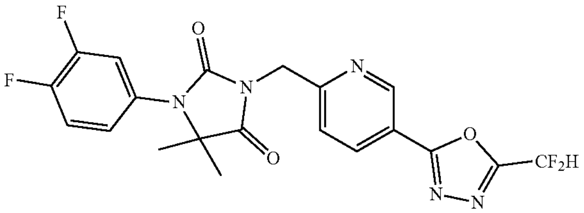 [SMILES: CC1(C)C(=O)N(Cc2ccc(-c3nnc(C(F)F)o3)cn2)C(=O)N1c1ccc(F)c(F)c1] |
| 17 | 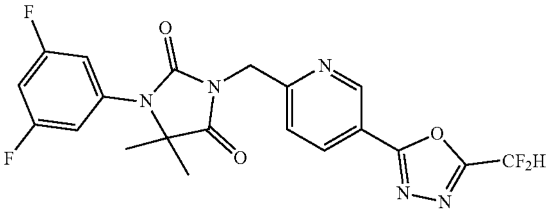 [SMILES: CC1(C)C(=O)N(Cc2ccc(-c3nnc(C(F)F)o3)cn2)C(=O)N1c1cc(F)cc(F)c1] |
| 18 | 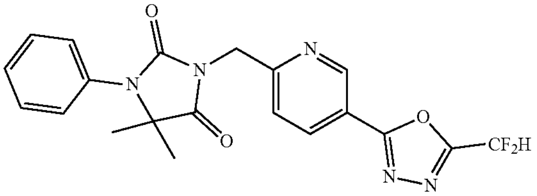 [SMILES: CC1(C)C(=O)N(Cc2ccc(-c3nnc(C(F)F)o3)cn2)C(=O)N1c1ccccc1] |
| 19 | 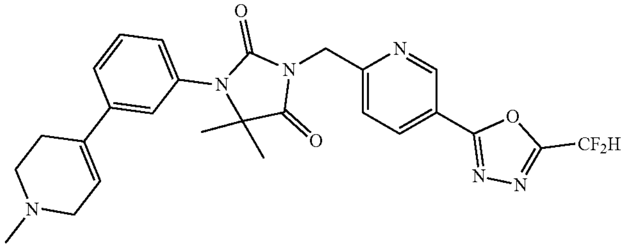 [SMILES: CN1CC=C(c2cccc(N3C(=O)N(Cc4ccc(-c5nnc(C(F)F)o5)cn4)C(=O)C3(C)C)c2)CC1] |
| 20 | 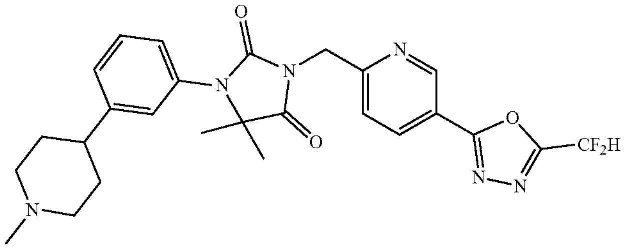 [SMILES: CN1CCC(c2cccc(N3C(=O)N(Cc4ccc(-c5nnc(C(F)F)o5)cn4)C(=O)C3(C)C)c2)CC1] |

-continued
| Compound | Structure |
| --- | --- |
| 21 | 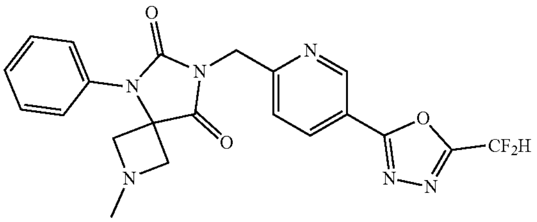 [SMILES: CN1CC2(C1)C(=O)N(Cc1ccc(-c3nnc(C(F)F)o3)cn1)C(=O)N2c1ccccc1] |
| 22 | 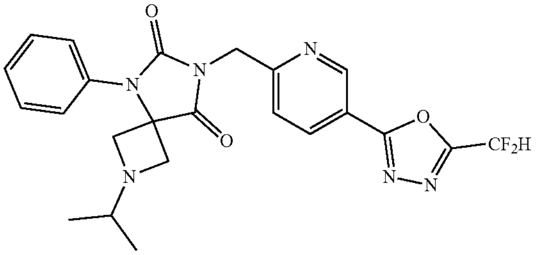 [SMILES: CC(C)N1CC2(C1)C(=O)N(Cc1ccc(-c3nnc(C(F)F)o3)cn1)C(=O)N2c1ccccc1] |
| 23 | 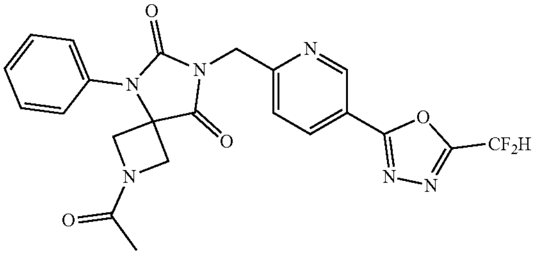 [SMILES: CC(=O)N1CC2(C1)C(=O)N(Cc1ccc(-c3nnc(C(F)F)o3)cn1)C(=O)N2c1ccccc1] |
| 24 | 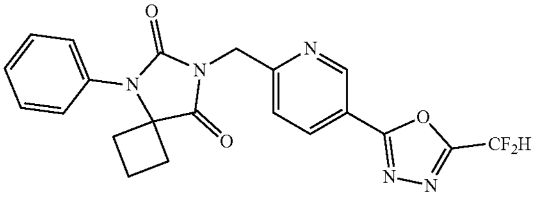 [SMILES: O=C1N(Cc2ccc(-c3nnc(C(F)F)o3)cn2)C(=O)C2(CCC2)N1c1ccccc1] |
| 25 | 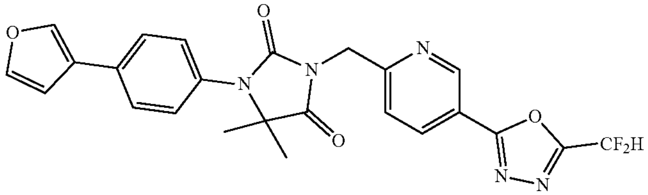 [SMILES: CC1(C)C(=O)N(Cc2ccc(-c3nnc(C(F)F)o3)cn2)C(=O)N1c1ccc(-c2ccoc2)cc1] |
| 26 | 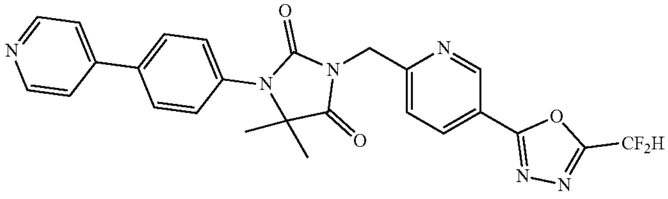 [SMILES: CC1(C)C(=O)N(Cc2ccc(-c3nnc(C(F)F)o3)cn2)C(=O)N1c1ccc(-c2ccncc2)cc1] |
| 27 | 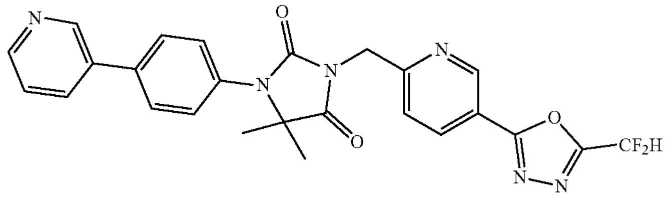 [SMILES: CC1(C)C(=O)N(Cc2ccc(-c3nnc(C(F)F)o3)cn2)C(=O)N1c1ccc(-c2cccnc2)cc1] |

-continued
| Compound | Structure |
|---|---|
| 28 | 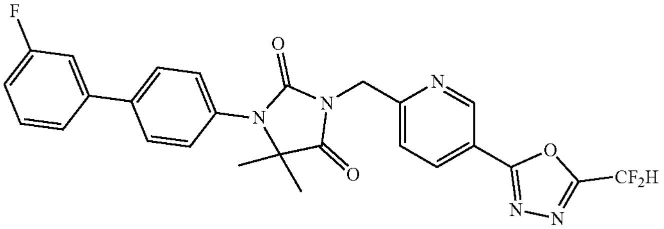 [SMILES: CC1(C)C(=O)N(Cc2ccc(-c3nnc(C(F)F)o3)cn2)C(=O)N1c1ccc(-c2cccc(F)c2)cc1] |
| 29 | 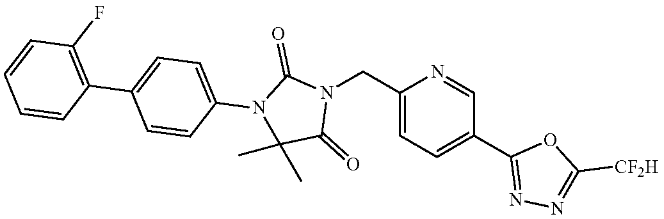 [SMILES: CC1(C)C(=O)N(Cc2ccc(-c3nnc(C(F)F)o3)cn2)C(=O)N1c1ccc(-c2ccccc2F)cc1] |
| 30 | 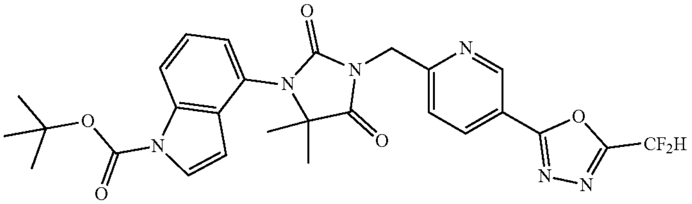 [SMILES: CC(C)(C)OC(=O)n1ccc2c(N3C(=O)N(Cc4ccc(-c5nnc(C(F)F)o5)cn4)C(=O)C3(C)C)cccc21] |
| 31 | 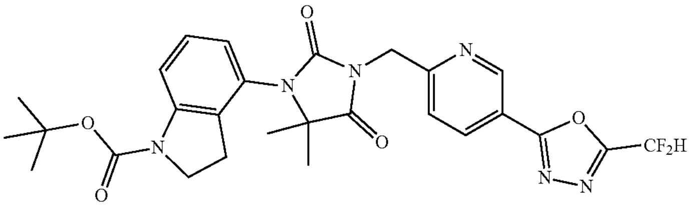 [SMILES: CC(C)(C)OC(=O)N1CCc2c1cccc2N1C(=O)N(Cc2ccc(-c3nnc(C(F)F)o3)cn2)C(=O)C1(C)C] |
| 32 | 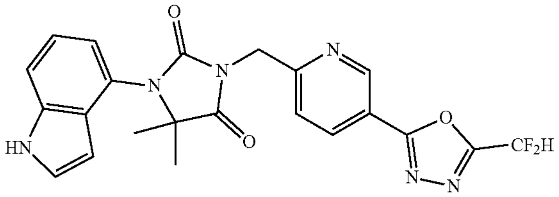 [SMILES: CC1(C)C(=O)N(Cc2ccc(-c3nnc(C(F)F)o3)cn2)C(=O)N1c1cccc2[nH]ccc12] |
| 33 | 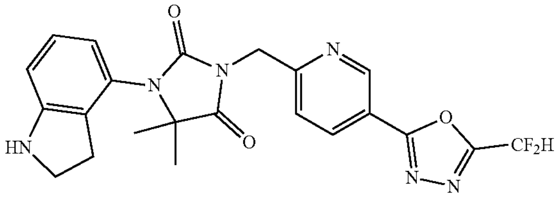 [SMILES: CC1(C)C(=O)N(Cc2ccc(-c3nnc(C(F)F)o3)cn2)C(=O)N1c1cccc2c1CCN2] |
| 34 | 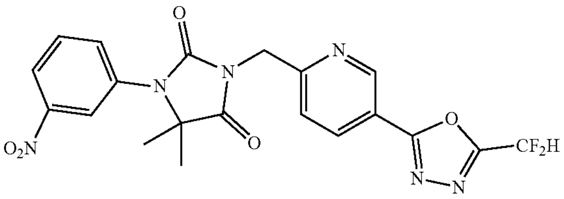 [SMILES: CC1(C)C(=O)N(Cc2ccc(-c3nnc(C(F)F)o3)cn2)C(=O)N1c1cccc([N+](=O)[O-])c1] |

-continued

| Compound | Structure |
| --- | --- |
| 35 | 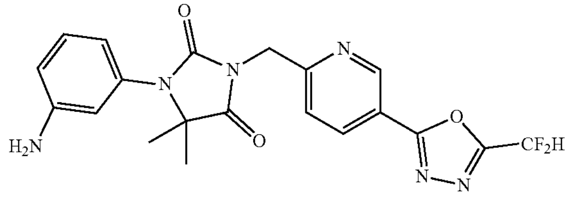 |
| 36 | 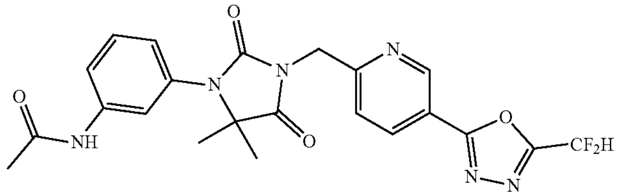 [SMILES: CC(=O)Nc1cccc(N2C(=O)N(Cc3ccc(-c4nnc(C(F)F)o4)cn3)C(=O)C2(C)C)c1] |
| 37 | 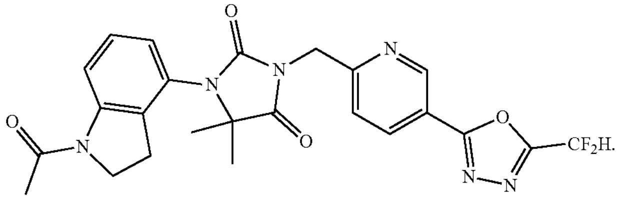 [SMILES: CC(=O)N1CCc2c1cccc2N1C(=O)N(Cc2ccc(-c3nnc(C(F)F)o3)cn2)C(=O)C1(C)C] |

4. A pharmaceutical composition comprising the compound represented by the chemical formula I according to claim 1, stereoisomers thereof or pharmaceutically acceptable salts thereof as an effective ingredient.

5. A method for treating histone deacetylase (HDAC)-mediated diseases, comprising administering a therapeutically effective amount of the compound represented by chemical formula I according to claim 1, stereoisomers thereof or pharmaceutically acceptable salts thereof; or a pharmaceutical composition comprising the same as an effective ingredient into a subject in need thereof, wherein the histone deacetylase-mediated diseases comprise infectious diseases, neoplasm, endocrinopathy, nutritional and metabolic diseases, mental and behavioral disorders, neurological diseases, eye and ocular adnexal diseases, respiratory diseases, digestive diseases, skin and subcutaneous tissue diseases, musculoskeletal system and connective tissue diseases or teratosis, deformities and chromosomal aberration.

6. A pharmaceutical composition comprising the compound represented by the chemical formula I according to claim 1, stereoisomers thereof or pharmaceutically acceptable salts thereof as an effective ingredient; and a pharmaceutically acceptable carrier.

7. The method according to claim 5, wherein the endocrinopathy, nutritional and metabolic diseases are Wilson's disease, amyloidosis or diabetes;

the mental and behavioral disorders are depression or rett syndrome;

the neurological diseases are central nervous system atrophy, neurodegenerative disease, motor disorder, neuropathy, motor neuron disease or central nervous system demyelinating disease;

the eye and ocular adnexal diseases are uveitis;

the skin and subcutaneous tissue diseases are psoriasis;

the musculoskeletal system and connective tissue diseases are rheumatoid arthritis, osteoarthritis or systemic lupus erythematosis;

the teratosis, deformities and chromosomal aberration are autosomal dominant polycystic kidney disease;

the infectious diseases are prion disease;

the neoplasm is benign tumor or malignant tumor;

the respiratory diseases are asthma; and the digestive diseases are alcoholic liver disease, inflammatory bowel disease, Crohn's disease or ulcerative bowel disease.

* * * * *